(12) United States Patent
Buist et al.

(10) Patent No.: US 10,414,732 B2
(45) Date of Patent: Sep. 17, 2019

(54) POLYMORPHIC COMPOUNDS AND USES THEREOF

(71) Applicant: Aldeyra Therapeutics, Inc., Lexington, MA (US)

(72) Inventors: Amanda Buist, Glasgow (GB); Eden Fucci, Arlington, MA (US); Stephen G. Machatha, Burlington, MA (US); Osama Suleiman, Cambridge (GB); Kate Wittering, Hampshire (GB)

(73) Assignee: Aldeyra Therapeutics, Inc., Lexington, MA (US)

( * ) Notice: Subject to any disclaimer, the term of this patent is extended or adjusted under 35 U.S.C. 154(b) by 0 days.

(21) Appl. No.: 15/924,005

(22) Filed: Mar. 16, 2018

(65) Prior Publication Data

US 2018/0265474 A1  Sep. 20, 2018

Related U.S. Application Data

(60) Provisional application No. 62/472,478, filed on Mar. 16, 2017, provisional application No. 62/519,331, filed on Jun. 14, 2017.

(51) Int. Cl.
| | |
|---|---|
| *C07D 215/38* | (2006.01) |
| *A61K 31/47* | (2006.01) |
| *C07C 309/04* | (2006.01) |
| *C07C 55/07* | (2006.01) |
| *C07C 309/25* | (2006.01) |
| *C07C 59/255* | (2006.01) |
| *C07C 309/29* | (2006.01) |
| *C07C 309/20* | (2006.01) |
| *C07C 309/30* | (2006.01) |

(52) U.S. Cl.
CPC ........... *C07D 215/38* (2013.01); *A61K 31/47* (2013.01); *C07C 55/07* (2013.01); *C07C 59/255* (2013.01); *C07C 309/04* (2013.01); *C07C 309/20* (2013.01); *C07C 309/25* (2013.01); *C07C 309/29* (2013.01); *C07C 309/30* (2013.01); *C07B 2200/13* (2013.01); *C07C 2602/42* (2017.05)

(58) Field of Classification Search
CPC .............................. C07D 215/38; A61K 31/47
USPC .......................................... 546/159; 514/313
See application file for complete search history.

(56) References Cited

U.S. PATENT DOCUMENTS

| | | | |
|---|---|---|---|
| 2,086,186 A | 7/1937 | Messer | |
| 3,912,748 A | 10/1975 | Evans et al. | |
| 4,956,351 A | 9/1990 | Mesens et al. | |
| 5,024,998 A | 6/1991 | Bodor | |
| 5,364,637 A | 11/1994 | De et al. | |
| 5,376,645 A | 12/1994 | Stella et al. | |
| 5,419,898 A | 5/1995 | Ikejiri et al. | |
| 5,472,954 A | 12/1995 | Loftsson | |
| 5,493,027 A | 2/1996 | Nichols et al. | |
| 5,576,311 A | 11/1996 | Guy | |
| 5,668,117 A | 9/1997 | Shapiro | |
| 5,767,109 A | 6/1998 | Sanchez et al. | |
| 5,998,488 A | 12/1999 | Shinohara et al. | |
| 6,191,127 B1 | 2/2001 | Holscher et al. | |
| 6,358,948 B1 | 3/2002 | Zhang et al. | |
| 6,444,221 B1 | 9/2002 | Shapiro | |
| 6,498,154 B1 | 12/2002 | Grubb et al. | |
| 6,515,010 B1 | 2/2003 | Franchini et al. | |
| 6,569,879 B2 | 5/2003 | Liu | |
| 7,083,803 B2 | 8/2006 | Peyman | |
| 7,297,709 B2 | 11/2007 | Dai et al. | |
| 7,531,564 B2 | 5/2009 | Malamas et al. | |
| 7,973,025 B2 * | 7/2011 | Jordan ................... | A61K 31/41 514/183 |
| 7,982,071 B2 | 7/2011 | Scott et al. | |
| 8,158,609 B1 | 4/2012 | Marsh et al. | |
| 8,575,221 B2 | 11/2013 | Masse et al. | |
| 8,722,669 B2 | 5/2014 | Palczewski et al. | |
| 8,791,154 B2 | 7/2014 | Gamache et al. | |
| 8,940,721 B2 | 1/2015 | Jordan et al. | |
| 8,940,764 B2 | 1/2015 | Jordan et al. | |
| 9,067,963 B2 | 6/2015 | Thompson et al. | |
| 9,265,759 B2 | 2/2016 | Jordan et al. | |
| 9,364,471 B2 | 6/2016 | Jordan et al. | |
| 9,375,408 B2 | 6/2016 | Singh | |
| 9,604,997 B2 | 3/2017 | Jordan | |
| 9,650,342 B2 | 5/2017 | Jordan et al. | |
| 9,687,481 B2 | 6/2017 | Brady et al. | |
| 9,814,701 B2 | 11/2017 | Jordan et al. | |

(Continued)

FOREIGN PATENT DOCUMENTS

| | | |
|---|---|---|
| EP | 0186367 A2 | 7/1986 |
| EP | 0245054 A1 | 11/1987 |

(Continued)

OTHER PUBLICATIONS

Abelson et al., "Conjunctival allergen challenge. A clinical approach to studying allergic conjunctivitis," Archives of Ophthalmology, 108(1):84-88 (1990).

Abelson et al., "Combined analysis of two studies using the conjunctival allergen challenge model to evaluate olopatadine hydrochloride, a new ophthalmic antiallergic agent with dual activity," American Journal of Ophthalmology, 125(6):797-804 (1998).

Abelson et al., "Conjunctival allergen challenge: models in the investigation of ocular allergy," Current Allergy and Asthma Reports, 3(4):363-368 (2003).

(Continued)

*Primary Examiner* — Charanjit Aulakh
(74) *Attorney, Agent, or Firm* — Andrea L.C. Reid; Dechert LLP

(57) ABSTRACT

The present invention provides freebase and salt forms, and compositions and methods thereof, useful for treating various conditions, in which aldehyde toxicity is implicated in the pathogenesis, by the administration of small molecule therapeutics acting as a scavenger for toxic aldehydes.

15 Claims, 25 Drawing Sheets

(56) References Cited

U.S. PATENT DOCUMENTS

| | | | |
|---|---|---|---|
| 9,896,419 B2 | 2/2018 | Jordan et al. | |
| 10,058,095 B2 | 8/2018 | Czarnik | |
| 10,111,862 B2 | 10/2018 | Chabala et al. | |
| 10,202,348 B2 | 2/2019 | Jordan et al. | |
| 10,213,395 B2 | 2/2019 | Brady et al. | |
| 2004/0132636 A1 | 7/2004 | Dooley et al. | |
| 2004/0198828 A1 | 10/2004 | Abelson et al. | |
| 2004/0235892 A1 | 11/2004 | Dai et al. | |
| 2005/0020603 A1 | 1/2005 | Dai | |
| 2005/0090553 A1 | 4/2005 | Shapiro | |
| 2005/0130906 A1 | 6/2005 | Matier et al. | |
| 2005/0197292 A1 | 9/2005 | Smithson et al. | |
| 2005/0234018 A1 | 10/2005 | Lyons | |
| 2006/0014786 A1 | 1/2006 | Raut | |
| 2006/0111318 A1 | 5/2006 | Okamoto | |
| 2006/0183909 A1 | 8/2006 | Schmitt et al. | |
| 2006/0189608 A1 | 8/2006 | Bingaman | |
| 2007/0129404 A1 | 6/2007 | Hagihara et al. | |
| 2007/0135481 A1 | 6/2007 | Jordan et al. | |
| 2009/0118503 A1 | 5/2009 | Sprott et al. | |
| 2009/0182009 A1 | 7/2009 | Jordan et al. | |
| 2010/0160304 A1 | 6/2010 | Katayama | |
| 2010/0240624 A1 | 9/2010 | Chapin et al. | |
| 2010/0331315 A1 | 12/2010 | Haddach et al. | |
| 2011/0263645 A1 | 10/2011 | Jordan et al. | |
| 2012/0108585 A1 | 5/2012 | Vu | |
| 2012/0295967 A1 | 11/2012 | Gamache et al. | |
| 2012/0302601 A1 | 11/2012 | Jordan et al. | |
| 2013/0165419 A1 | 6/2013 | Lindstrom et al. | |
| 2013/0190500 A1 | 7/2013 | Greiner et al. | |
| 2014/0038918 A1 | 2/2014 | Rodriguez-Boulan et al. | |
| 2014/0235604 A1 | 8/2014 | Palczewski et al. | |
| 2015/0209333 A1 | 7/2015 | Jordan | |
| 2015/0209345 A1 | 7/2015 | Jordan et al. | |
| 2015/0258120 A1 | 9/2015 | Zarnitsyn et al. | |
| 2015/0335632 A1 | 11/2015 | Brady et al. | |
| 2015/0344432 A1 | 12/2015 | Jordan et al. | |
| 2015/0344447 A1 | 12/2015 | Chabala et al. | |
| 2016/0052930 A1 | 2/2016 | Fensome et al. | |
| 2017/0029354 A1 | 2/2017 | Singh | |
| 2017/0239196 A1 | 8/2017 | Brady et al. | |
| 2017/0266220 A1 | 9/2017 | Young et al. | |
| 2018/0050989 A1 | 2/2018 | Machatha et al. | |
| 2018/0092882 A1 | 4/2018 | Jordan et al. | |
| 2018/0194733 A1 | 7/2018 | Jordan et al. | |
| 2018/0250306 A1 | 9/2018 | Brady et al. | |
| 2018/0354905 A1 | 12/2018 | Brady et al. | |

FOREIGN PATENT DOCUMENTS

| | | |
|---|---|---|
| EP | 0483881 A1 | 5/1992 |
| EP | 1621199 A1 | 1/2006 |
| EP | 2301549 A1 | 3/2011 |
| EP | 1888548 B1 | 8/2012 |
| GB | 2327672 A | 2/1999 |
| JP | 2002003364 A | 1/2002 |
| JP | 3736916 B2 | 1/2006 |
| JP | 2007532648 A | 11/2007 |
| JP | 2008542291 A | 11/2008 |
| JP | 4466875 B2 | 5/2010 |
| JP | 5194218 B2 | 5/2013 |
| SU | 509046 A1 | 6/1984 |
| WO | WO 1996022992 A1 | 8/1996 |
| WO | WO 1998005645 | 2/1998 |
| WO | WO 1999046237 A1 | 9/1999 |
| WO | WO 2001041757 A1 | 6/2001 |
| WO | WO 2004082622 A2 | 9/2004 |
| WO | WO 2004091630 A1 | 10/2004 |
| WO | WO 2005035506 A1 | 4/2005 |
| WO | WO 2005040151 A1 | 5/2005 |
| WO | WO 2005051328 A2 | 6/2005 |
| WO | WO 2005079774 A2 | 9/2005 |
| WO | WO 2005105067 A2 | 11/2005 |
| WO | WO 2006002473 A1 | 1/2006 |
| WO | WO 2006049968 A1 | 5/2006 |
| WO | WO 2006077821 A1 | 7/2006 |
| WO | WO 2006127945 A1 | 11/2006 |
| WO | WO 2007118276 A1 | 10/2007 |
| WO | WO 2008014602 A1 | 2/2008 |
| WO | WO 2009045479 A1 | 4/2009 |
| WO | WO 2009102418 A1 | 8/2009 |
| WO | WO 2010133672 A1 | 11/2010 |
| WO | WO 2011008202 A1 | 1/2011 |
| WO | WO 2011071995 A2 | 6/2011 |
| WO | WO 2011072141 A1 | 6/2011 |
| WO | WO 2011078204 A1 | 6/2011 |
| WO | WO 2012097173 A2 | 7/2012 |
| WO | WO 2012105887 A1 | 8/2012 |
| WO | WO 2014100425 A1 | 7/2014 |
| WO | WO 2014116593 A1 | 7/2014 |
| WO | WO 2014116836 A2 | 7/2014 |
| WO | WO 2015187942 A1 | 12/2015 |
| WO | WO 2016085939 A2 | 6/2016 |
| WO | WO 2017035077 A1 | 3/2017 |
| WO | WO 2017035082 A1 | 3/2017 |
| WO | WO 2017147617 A1 | 8/2017 |
| WO | WO 2017196881 A1 | 11/2017 |
| WO | WO 2018039192 A1 | 3/2018 |
| WO | WO 2018039197 A1 | 3/2018 |
| WO | WO 2018170476 A1 | 9/2018 |

OTHER PUBLICATIONS

Abramovitz, M. et al., "The utilization of recombinant prostanoid receptors to determine the affinities and selectivities of prostaglandins and related analogs," Biochem. Biophys. Acta., 1483(2):285-293 (2000).

Acland et al., "Gene Therapy Restores Vision in a Canine Model of Childhood Blindness," Nature Genetics, 28(1):92-95 (2001).

Aharony, D. et al., "Pharmacological characterization of cloned human NK-2 (neurokinin A) receptor expressed in a baculovirus/Sf-21 insect cell system," Molecular Pharmacology, 44(2):356-363 (1993).

Akturk, S. et al., "Nitric oxide and malondialdehyde levels in plasma and tissue of psoriasis patients," Journal of the European Academy of Dermatology and Venereology, 26(7):833-837 (2012).

Albano et al., "Immune response towards lipid peroxidation products as a predictor of progression of non-alcoholic fatty liver disease to advanced fibrosis," Gut 54:987-93 (2005).

Aldini et al., "Lipoxidation-Derived Reactive Carbonyl Species as Potential Drug Targets in Preventing Protein Carbonylation and Related Cellular Dysfunction," ChemMedChem, 1(10):1045-1058 (2006).

Aldini et al., "The carbonyl scavenger carnosine ameliorates dyslipidaemia and renal function in Zucker obese rats," The Journal of Cellular and Molecular Medicine, 15(6):1339-1354 (2011).

Al-Essa et al., "Clinical, fluorine-18 labeled 2-fluoro-2-deoxyglucose positron emission tomography (FDG PET), MRI of the brain and biochemical observations in a patient with 4-hydroxybutyric aciduria; a progressive neurometabolic disease," Brain Dev., 22(2):127-31 (2000).

Al-Hasani, H. et al., "Phosphoryl exchange is involved in the mechanism of the insulin receptor kinase," FEBS Lett., 349:17-22 (1994).

Amara et al., "Autoantibodies to malondialdehyde-modified epitope in connective tissue disease and vasculitides," Clinical and Experimental Immunology, 101(2):233-238 (1995).

Apparsundaram, S. et al., "Molecular cloning of a human, hemicholinium-3-sensitive choline transporter," Biochem. Biophys. Res. Commun., 276(3):862-867 (2000).

Ardati, A. et al., "Interaction of [3H]orphanin FQ and 125I-Tyr14-orphanin FQ with the orphanin FQ receptor: kinetics and modulation by cations and guanine nucleotides," Mol. Pharmacol., 51:816-824 (1997).

Ashton et al., "Location of penetration and metabolic barriers to levobunolol in the corneal epithelium of the pigmented rabbit," The Journal of Pharmacology and Experimental Therapeutics, 259(2):719-724 (1991).

(56) References Cited

OTHER PUBLICATIONS

Atkinson et al., "Triazaphenanthrenes. Part VI.* Further Observations on the Widman-Stoermer and Brosche Reactions," J. Chem. Soc. (C) pp. 2053-2060 (1966).
Augustin et al., "Oxidative reactions in the tear fluid of patients suffering from dry eyes," Graefe's Archive for Clinical and Experimental Ophthalmology, 233(11):694-698 (1995).
Bachman, G.B. et al., "Quinoline derivatives from 3-nitro-4-hydroxyquinoline," Am. Chem. Soc., 69:365-371 (1947).
Ballard, S.A. et al., "Effects of sildenafil on the relaxation of human corpus cavernosum tissue in vitro and on the activities of cyclic nucleotide phosphodiesterase isozymes," J. Urol., 159(6):2164-2171 (1998).
Bardwell, A.J. et al., "Docking sites on mitogen-activated protein kinase (MAPK) kinases, MAPK phosphatases and the Elk-1 transcription factor compete for MAPK binding and are crucial for enzymic activity," Biochem. J., 370:1077-1085 (2003).
Baron, B.M. et al., "[3H]MDL 105,519, a high-affinity radioligand for the N-methyl-D-aspartate receptor-associated glycine recognition site," J. Pharmacol. Exp. Ther., 279:62-68 (1996).
Bartoli et al., "Malondialdehyde in Exhaled Breath Condensate as a Marker of Oxidative Stress in Different Pulmonary Diseases," Mediators of Inflammation, vol. 2011, Article ID 891752 (2011) (7 pages).
Batista et al., "Age-dependent changes in rat lacrimal gland antioxidant and vesicular related protein expression profiles," Molecular Vision, 18:194-202 (2012).
Batista et al., "Short-term treatment with bisphenol-A leads to metabolic abnormalities in adult male mice," PLOS One, vol. 7, No. 3, (2012).
Baum et al, "Omega 3 fatty acid inhibition of inflammatory cytokine-mediated Connexin43 regulation in the heart," Front. Physiol. 3:272 doi: 10.3389/fphys.2012.00272. eCollection 2012 (2012).
Baz et al., "Plasma reactive oxygen species activity and antioxidant potential levels in rosacea patients: correlation with seropositivity to Helicobacter pylori," International Journal of Dermatology, 43(7):494-497 (2004).
Berge et al., "Pharmaceutical salts," The Journal of Pharmaceuticals Sciences, 66(1):1-19 (1977).
Berkhout, T.A. et al., "Cloning, in vitro expression, and functional characterization of a novel human CC chemokine of the monocyte chemotactic protein (MCP) family (MCP-4) that binds and signals through the CC chemokine receptor 2B,", J. Biol. Chem., 272:16404-16413 (1997).
Bernstein et al., "Retinal Toxicity Associated with Occupational Exposure to the Fish Anesthetic MS-222," Am J Ophthalmol, 124(6):843-844 (1997).
Bernstein et al., "Mechanism of Action of Aromatic Amines that Short-Circuit the Visual Cycle," Biochemistry, 25(11):3370-3377 (1986).
Bernstein et al., "Short-Circuiting the Visual Cycle with Retinotoxic Aromatic Amines," Proc Natl Acad Sci USA, 83(6):1632-1635 (1986).
Bernstein et al., The Specific Inhibition of 11-cis-retinyl Palmitate Formation in the Frog Eye by Diaminophenoxypentane, an Inhibitor of Rhodopsin Regeneration, Vision Research, 25(6):741-748 (1985).
Bickett, D.A. et al., "A high throughput fluorogenic substrate for interstitial collagenase (MMP-1) and gelatinase (MMP-9)," Anal. Biochem., 212:58-64 (1993).
Bignon, E. et al., "SR146131: a new potent, orally active, and selective nonpeptide cholecystokinin subtype 1 receptor agonist. I. In vitro studies," J. Pharmacol. Exp. Ther. 289:742-751 (1999).
Bousquet et al., "How to Design and Evaluate Randomized Controlled Trials in Immunotherapy for Allergic Rhinitis: An ARIA-GA2 LEN Statement," Allergy, 66(6):765-774 (2011).
Bozkir et al., "Effect of hydroxypropyl-beta-cyclodextrin on the solubility, stability and in-vitro release of ciprofloxacin for ocular drug delivery," Acta Poloniae Pharmaceutica, 69(4):719-24 (2012).
Bragagni et al., "Cyclodextrin complexation highly enhances efficacy of arylsulfonylureido benzenesulfonamide carbonic anhydrase inhibitors as a topical antiglaucoma agents," Bioorganic & Medicinal Chemistry, 23(18):6223-6227) (2015).
Brenneman et al., "Cannabidiol Provides Protection from Ethanol and Ammonium toxicity in a Hippocampal Model of Hepatic Encephalopathy," 24th Annual Symposium of the International Cannabinoid Research Society, Baveno, Italy, Jun. 28-Jun. 3, 2014 (p. 73).
Brenneman et al., "Small Molecule Anticonvulsant Agents with Potent In Vitro Neuroprotection," Journal of Molecular Neuroscience, 47(2):368-379 (2012).
Brockhaus, M. et al., "Identification of two types of tumor necrosis factor receptors on human cell lines by monoclonal antibodies," Proc. Natl. Acad. Sci. U.S.A., 87:3127-3131 (1990).
Brown, G.B., "3H-batrachotoxinin-A benzoate binding to voltage-sensitive sodium channels: inhibition by the channel blockers tetrodotoxin and saxitoxin," J. Neurosci., 6:2064-2070 (1986).
Brozek et al., "Grading quality of evidence and strength of recommendations in clinical practice guidelines: Part 2 of 3. The GRADE approach to grading quality of evidence about diagonstic tests and strategies," Allergy, 64(8):1109-1116 (2009).
Bryant, H.U. et al., "A novel class of 5-HT2A receptor antagonists: aryl aminoguanidines," Life Sci., 59(15):1259-1268 (1996).
Bucciantini et al., "Inherent Toxicity of Aggregates Implies a Common Mechanism for Protein Misfolding Diseases," Nature, 416(6880):507-511 (2002).
Buchan, K.W. et al., "Characterization of three non-peptide endothelin receptor ligands using human cloned ETA and ETB receptors," Brit. J. Pharmacol., 112:1251-1257 (1994).
Buddi et al., "Evidence of oxidative stress in human corneal diseases," The Journal of Histochemistry and Cytochemistry: official journal of the Histochemistry Society, 50(3):341-351 (2002).
Bundgaard et al., "Glycolamide esters as biolabile prodrugs of carboxylic acid agents: Synthesis, Stability, bioconversion, and physicochemical properties," Journal of Pharmaceutical Sciences, 77(4):285-298 (1988).
Bundgaard, "Mean to enhance penetration: (1) Prodrugs as a means to improve the delivery of peptide drugs," Advanced Drug Delivery Review, 8(1):1-38 (1992).
Burcham et al., "Aldehyde-Sequestering Drugs: Tools for Studying Protein Damage by Lipid Peroxidation Products," Toxicology, 181-182:229-236 (2002).
Burstein, "Preservative cytotoxic threshold for benzalkonium chloride and chlorhexidine digluconate in cat and rabbit corneas," Investigative Ophthalmology and Visual Science, 19(3):308-313 (1980).
Canonica et al., "Recommendations for standardization of clinical trials with Allergen Specific Immunotherapy for respiratory allergy. A statement of a World Allergy Organization (WAO) taskforce," Allergy, 62(3):317-324 (2007).
Canonica et al., "Sub-lingual immunotherapy: World Allergy Organization Position Paper 2009," Allergy, 64(Suppl 91:1-59 (2009).
Casanaro et al., "A convenient solvent system for cellulose dissolution and derivatization: Mechanistic aspects of the acylation of the biopolymer in tetraallylammonium fluoride/dimethyl sulfoxide," Carbohydrate Polymers, 8(3):1395-1402 (2011).
Casanaro et al., "Efficacy of vigabatrin intervention in a mild phenotypic expression of succinic semialdehyde dehydrogenase deficiency," JIMD Rep. 2:119-23 (2011).
Cesura et al., "Characterization of the binding of [3H]Ro 41-1049 to the active site of human monoamine oxidase-A," Mol. Pharmacol., 37:358-366 (1990).
Chapple et al., "Unfolding Retinal Dystrophies: a Role for Molecular Chaperones?" Trends Mol Med, 7(9):414-421 (2001).
Cheng et al., "A synthetic peptide derived from p34cdc2 is a specific and efficient substrate of src-family tyrosine kinases," J. Biol. Chem., 267:9248-9256 (1992).
Chicchi et al., "Alterations in receptor activation and divalent cation activation of agonist binding by deletion of intracellular domains of the glucagon receptor," J. Biol. Chem., 272:7765-7769 (1997).
Choi et al., "The human serotonin 5-HT2B receptor: pharmacological link between 5-HT2 and 5-HT1D receptors," FEBS Lett., 352:393-399 (1994).

(56) References Cited

OTHER PUBLICATIONS

Clark et al., "Inhibition of dexamethasone-induced cytoskeletal changes in cultured human trabecular meshwork cells by tetrahydrocortisol," Invest. Ophtalmol. Vis. Sci., 37:805-813 (1996).
ClinicalTrials.gov identifier NCT02578914, "A Safety and Activity Study of NS2 in Subjects with Allergic Conjunctivitis," https://clinicaltrials.gov/ct2/show/NCT02578914 (6 pages) (2015).
Clinical Trials Results for Outcome Measures of Ocular Itching and Ocular Tearing (1 page) (2016).
ClinicalTrials.gov identifier NCT02406209, "A Safety and Efficacy Study of NS2 in Patients with Anterior Uveitis," https://clinicaltrials.gov/ct2/show/NCT02406209 (4 pages) (2015).
Clinical Trials Results of Treatment with Aldehyde Trapping Compound NS2 (1 page) (2015).
ClinicalTrials.gov identifier NCT02402309, "A Study of Topical NS2 Cream to Treat Ichthyosis in Sjogren-Larsson Syndrome (SLS)," https://clinicaltrials.gov/ct2/show/NCT02402309 (3 pages) (2015).
Clinical Trials Results of Treatment with NS2 Topical Formulation (1 page) (2015).
Conover et al., "Thiazole Analogs of Pyridoxine," Journal of the American Chemical Society, 72(11):5221-5225 (1950).
Couvineau et al., "Molecular identification and structural requirement of vasoactive intestinal peptide (VIP) receptors in the human colon adenocarcinoma cell line, HT-29," Biochem. J., 231:139-143 (1985).
De Jong, "Age-Related Macular Degeneration," N Engl J Med, 355(14):1474-1485 (2006).
Del Valle, "Cyclodextrins and their uses: a review," Process Biochemistry, 39(9):1033-1046 (2004).
Dente et al., "Modified phage peptide libraries as a tool to study specificity of phosphorylation and recognition of tyrosine containing peptides," J. Mol. Biol., 269:694-703 (1997).
Devedjian et al., "Further characterization of human alpha 2-adrenoceptor subtypes: [3H]RX821002 binding and definition of additional selective drugs," Eur. J. Pharmacol., 252:43-49 (1994).
Dolmotova et al, "Cardiomyocyte ATP release through pannexin 1 aids in early fibroblast activation," Am. J. Physiol Heart Circ Physiol 303(10):H1208-1218 (2012).
Dorje et al., "Antagonist binding profiles of five cloned human muscarinic receptor subtypes," J. Pharmacol. Exp. Ther., 256:727-733 (1991).
Dowling, "Neural and Photochemical Mechanisms of Visual Adaptation in the Rat," Journal of General Physiology, 46(6):1287-1291 (1963).
Drysdale et al., "Complex Promoter and Coding Region Beta 2-adrenergic Receptor Haplotypes Alter Receptor Expression and Predict in vivo Responsiveness," Proc Natl Acad Sci USA, 97(19):10483-10488 (2000).
Ellman et al., "A new and rapid colorimetric determination of acetylcholinesterase activity," Biochem. Pharmacol., 7: 88-95 (1961).
Erdos et al, "Neutral endopeptidase 24.11 (enkephalinase) and related regulators of peptide hormones," FASEB J. 3:145 (1989).
Ermolieff et al., "Proteolytic activation of recombinant pro-memapsin 2 (pro-beta-secretase) studied with new fluorogenic substrates," Biochemistry, 39:12450-12456 (2000).
Escalera et al., "Succinic semialdehyde dehydrogenase deficiency: decrease in 4-OH-butyric acid levels with low doses of vigabatrin," An Pediatr (Barc). 72(2):128-32 (2010).
European Supplementary Partial Search Report issued by the European Patent Office for European Patent Application No. 13865015.5 dated Mar. 31, 2016 (9 pages).
European Supplementary Partial Search Report issued by the European Patent Office for European Patent Application No. 14743711.5 dated Jul. 20, 2016 (14 pages).
Everest-Todd, "Topical Application of Cyclodextrin Ethers in the Control of Pain," Proceedings of the Eighth International Symposium on Cyclodextrins, pp. 495-498 (1998).
FDA, "BAM R59: Phosphate-Buffered Saline (PBS), pH 7.4," Jan. 2001, retrieved online at <http://www.fda.gov/Food/FoodScienceR.esearch/LaboratoxyMethods/ucm062268.htm> on Apr. 18, 2015 (1 page).
Feighner et al., "Receptor for motilin identified in the human gastrointestinal system," Science, 284:2184-2188 (1999).
Fernandes et al., "Characterization of angiotensin-converting enzymes 1 and 2 in the soleus and plantaris muscles of rats," Braz J Med Biol Res., 43:837-842 (2010).
Ferry et al., "Binding of prostaglandins to human PPARγ: Tool assessment and new natural ligands," Eur. J. Pharmacol., 417:77-89 (2001).
Feve et al., "Transcriptional down-regulation by insulin of the beta 3-adrenergic receptor expression in 3T3-F442A adipocytes: a mechanism for repressing the cAMP signaling pathway," Proc Natl Acad Sci USA. 91:5677 (1994).
Fiske et al., "The Colormetric Determination of Phosphorus," J. Biol. Chem., 66:375-400 (1925).
Fitzmaurice et al., "Aldehyde dehydrogenase inhibition as a pathogenic mechanism in Parkinson disease," Proc. Natl Acad Sci U.S.A, 110(2):636-641 (2013).
Ford et al., "Pharmacological pleiotropism of the human recombinant alphaA-adrenoceptor: implications for alphal-adrenoceptor classification," Brit. J. Pharmacol., 121:1127-1135 (1997).
Fowler et al., "Coloured Complexes of all-trans-retinal with Benzocaine and Other Local Anesthetics," J Photochem Photobiol B, 8(2):183-188 (1991).
Frantz et al., "The Activation State of p38 Mitogen-Activated Protein Kinase Determines the Efficiency of ATP Competition for Pyridinylimidazole Inhibitor Binding," Biochemistry, 37:13846-13853 (1998).
Fuchs et al., "Functional characterization of three mutations of the endothelin B receptor gene in patients with Hirschsprung's disease: evidence for selective loss of Gi coupling," Mol. Med., 7:115-124 (2001).
Fukunaga et al., "Single nucleotide polymorphism of human platelet-activating factor receptor impairs G-protein activation," J. Biol. Chem., 276:43025-43030 (2001).
Ganapathy et al., "Molecular and ligand-binding characterization of the sigma-receptor in the Jurkat human T lymphocyte cell line," JPET, 289:251-260 (1999).
Gibson et al., "Stable isotope dilution analysis of 4-hydroxybutyric acid: an accurate method for quantification in physiological fluids and the prenatal diagnosis of 4-hydroxybutyric aciduria," Biomed Environ Mass Spectrom., 19(2):89-93 (1990).
Gibson et al., "Stable-isotope dilution analysis of D- and L-2-hydroxyglutaric acid: application to the detection and prenatal diagnosis of D- and L-2-hydroxyglutaric acidemias," Pediatr Res., 34(3):277-80 (1993).
Godard et al., "Sur les orthoamino formyl quinoleines, nouveaux synthons heterocycliques," J Heterocyclic Chem, 17(3):465-473 (1980).
Good, "Measuring field loss in children administered vigabatrin: a problem in search of a solution," J AAPOS. 15(5):411-2 (2011).
Gopalakrishnan et al., "Stable expression, pharmacologic properties and regulation of the human neuronal nicotinic acetylcholine alpha 4 beta 2 receptor," J. Pharmacol. Exp. Ther., 276:289-297 (1996).
Gould et al., "[3H]nitrendipine-labeled calcium channels discriminate inorganic calcium agonists and antagonists," Proc. Natl. Acad. Sci. U.S.A., 79:3656-3660 (1982).
Grandy et al., "Cloning of the cDNA and gene for a human D2 dopamine receptor," Proc. Natl. Acad. Sci. U.S.A., 86:9762-9766 (1989).
Green et al., "Influence of Various Agents on Corneal Permeability," American Journal of Ophthalmology, 72(5):897-905 (1971).
Green et al., "Characterization of [(3)H]-CGP54626A binding to heterodimeric GABA(B) receptors stably expressed in mammalian cells," Brit. J. Pharmacol., 131:1766-1774 (2000).
Hampson et al., "Cannabidiol and (−)Delta9-tetrahydrocannabinol are neuroprotective antioxidants," Proc. Nat. Acad. Sci 95:8268-8273 (1998).

(56) References Cited

OTHER PUBLICATIONS

Hassan et al., "Oxidative stress in systemic lupus erythematosus and rheumatoid arthritis patients: relationship to disease manifestations and activity," International Journal of Rheumatic Diseases, 14(1):325-331 (2011).

Heuillet et al., "Characterization of a Human NK1 Tachykinin Receptor in the Astrocytoma Cell Line U 373 MG," J. Neurochem., 60:868-876 (1993).

Highlights of Prescribing Information, Bridion® (sugammadex) Injection, for intravenous use, Initial U.S. Approval: 2015, Last Revised Dec. 2015 (19 pages).

Hogema et al., "Pharmacologic rescue of lethal seizures in mice deficient in succmate semialdehyde dehydrogenase," Nat Genet. 29:212-16 (2001).

Hope et al., "Characterization of a human 5-hydroxytryptamine3 receptor type A (h5-HT3R-AS) subunit stably expressed in HEK 293 cells," Brit. J. Pharmacol., 118:1237-1245 (1996).

Hoyer et al., "Characterization of the 5-HT1B recognition site in rat brain: binding studies with (−)[125I]iodocyanopindolol," Eur. J. Pharmacol., 118:1-12 (1985).

Huang et al., "Identification of human Ether-à-go-go related gene modulators by three screening platforms in an academic drug-discovery setting," Assay Drug Dev Technol., 8(6):727-42 (2010).

Huang et al., "Novel peptide inhibitors of angiotensin-converting enzyme 2," J. Biol. Chem., 278:15532-15540 (2003).

Hubbard, "Geometrical Isomerization of Vitamin A, Retinene and Retinene Oxime," Journal of the American Chemical Society, 78(18):4662-4667 (1956).

Hugues et al., "Preparation of a pure monoiodo derivative of the bee venom neurotoxin apamin and its binding properties to rat brain synaptosomes," J. Biol. Chem., 257:2762-2769 (1982).

Hurd et al., "Reaction of Propiolactone with Aniline Derivatives," Journal of the American Chemical Society, 74(23):5889-5893 (1952).

Inoue et al., "Filter-binding assay procedure for thyroid hormone receptors," Anal Biochem. 134(1):176 (1983).

International Preliminary Report on Patentability issued in PCT/US2016/048054 dated Feb. 27, 2018 (5 pages).

International Preliminary Report on Patentability issued in PCT/US2016/048064 dated Feb. 27, 2018 (6 pages).

International Preliminary Report on Patentability issued by the Korean Intellectual Property Office as International Searching Authority for International Application No. PCT/US2013/076592 dated Jun. 23, 2015 (6 pages).

International Preliminary Report on Patentability issued by the Korean Intellectual Property Office as International Searching Authority for International Application No. PCT/US2014/012356 dated Jul. 28, 2015 (7 pages).

International Preliminary Report on Patentability issued by the United States Patent and Trademark Office as International Searching Authority for International Application No. PCT/US2014/012762 dated Jul. 28, 2015 (8 pages).

International Preliminary Report on Patentability issued by the European Patent Office as International Searching Authority for International Application PCT/US2006/020320 dated Nov. 30, 2007 (8 pages).

International Search Report and Written Opinion issued in PCT/US2006/020320, dated Sep. 26, 2006 (10 pages).

International Search Report and Written Opinion issued by the United States Patent and Trademark Office as International Searching Authority for International Application No. PCT/US2017/047945 dated Oct. 20, 2017 (9 pages).

International Search Report and Written Opinion issued in PCT/US2016/048054 dated Nov. 4, 2016 (7 pages).

International Search Report and Written Opinion issued in PCT/US2016/048064 dated Nov. 15, 2016 (8 pages).

International Search Report and Written Opinion issued by the United States Patent and Trademark Office as International Searching Authority for International Application No. PCT/US2010/059719 dated Feb. 8, 2011 (7 pages).

International Search Report and Written Opinion issued by the Korean Intellectual Property Office as International Searching Authority for International Application No. PCT/US2013/076592 dated Apr. 30, 2014 (10 pages).

International Search Report and Written Opinion issued by the Korean Intellectual Property Office as International Searching Authority for International Application No. PCT/US2014/012356 dated May 30, 2014 (11 pages).

International Search Report and Written Opinion issued by the United States Patent and Trademark Office as International Searching Authority for International Application No. PCT/US2014/012762 dated Jul. 18, 2014 (11 pages).

International Search Report and Written Opinion issued by the United States Patent and Trademark Office as International Searching Authority for International Patent Application No. PCT/US2017/020020 dated May 24, 2017 (12 pages).

International Search Report and Written Opinion issued in PCT/US2018/023000 dated Jun. 1, 2018 (8 pages).

Iriyama et al., "A2E, a pigment of the lipofuscin of retinal pigment epithelial cells, is an endogenous ligand for retinoic acid receptor," J Biol Chem., 283(18):11947-53 (2008) Epub Mar. 6, 2008.

Ishida et al., "Stabilization of calmodulin-dependent protein kinase II through the autoinhibitory domain," J. Biol. Chem., 270:2163-2170 (1995).

Ito et al., "A Medium-Term Rat Liver Bioassay for Rapid in vivo Detection of Carcinogenic Potential of Chemicals," Cancer Science, 94(1):3-8 (2003).

Itokawa et al., "Antiangiogenic effect by SU5416 is partly attributable to inhibition of Flt-1 receptor signaling," Mol. Cancer Ther., 1:295-302 (2002).

Jafari et al., "Evaluation of plasma, erythrocytes, and bronchoalveolar lavage fluid antioxidant defense system in sulfur mustard-injured patients," Clin Toxicol (Phila)., 48(3):184-92 (2010).

Janowski et al., "Structural requirements of ligands for the oxysterol liver X receptors LXRalpha and LXRbeta," Proc. Natl. Acad. Sci. USA, 96:266-271 (1999).

Jarrett et al., "Mitochondrial DNA damage and impaired base excision repair during epileptogenesis," Neurobiology of Disease, 30(1):130-138 (2008).

Ji et al., "Exploration of diverse hinge-binding scaffolds for selective Aurora kinase inhibitors," Bioorg. & Med. Chem. Let. 22:4528 (2012).

Johannsdottir et al., "Development of a Cyclodextrin-Based Aqueous Cyclosporin a Eye Drop Formulations," International Journal of Pharmaceutics, 493(1-2):86-95 (2015).

Johnson et al., "2-Hydroxypropyl-β-Cyclodextrin Removes All-Trans Retinol from Frog Rod Photoreceptors in a Concentration-Dependent Manner," Journal of Ocular Pharmacology and Therapeutics, 26(3):245-248 (2010).

Joseph et al., "Binding of (−)-[3H]-CGP12177 at two sites in recombinant human beta 1-adrenoceptors and interaction with beta-blockers," Naun.-Sch. Arch. Pharm., 369:525-532 (2004).

Kam et al., "Topical Cyclodextrin Reduces Amyloid Beta and Inflammation Improving Retinal Function in Ageing Mice," Experimental Eye Research, 135:59-66 (2015).

Kamino et al., "Deficiency in mitochondrial aldehyde dehydrogenase increases the risk for late-onset Alzheimer's disease in the Japanese population," Biochemical and Biophysical Research Communications, 273(1):192-196 (2000).

Karahashi et al., "Changes of caspase activities involved in apoptosis of a macrophage-like cell line J774.1/JA-4 treated with lipopolysaccharide (LPS) and cycloheximide," Biol. Pharm. Bull., 23:140-144 (2000).

Karan et al., Lipofuscin Accumulation, Abnormal Electrophysiology, and Photoreceptor Degeneration in Mutant ELOVL4 Transgenic Mice: A Model for Macular Degeneration, Proc Natl Acad Sci USA, 102(11):4164-4169 (2005).

Katugampola et al., "[(125)I]-(Pyr(1))Apelin-13 is a novel radioligand for localizing the APJ orphan receptor in human and rat tissues with evidence for a vasoconstrictor role in man," Brit. J. Pharmacol., 132:1255-1260 (2001).

(56) References Cited

OTHER PUBLICATIONS

Keri, "Rosacea," Merck Manual, Professional Version, https://www.merckmanuals.com/professional/dermatologic-disorders/acne-and-related-disorders/rosacea, 7 pages (2017).
Knapp et al., "Intraocular Availability of Topically Applied Mycophenolate Mofetil in Rabbits," J. Ocul. Pharmacol. Ther., 19(2):181-192 (2003).
La Rosa et al., "Allergic conjunctivitis: a comprehensive review of the literature," Ital J Pediatr, 39:18 (2013).
Landor et al., "Allenes. Part 49, 4-Amino-2-(1-hydroxyalkyl)quinolones from Phenylhydroxylamine and Allenic Nitrites," J Chem Soc Perkin Trans 1, pp. 251-254 (1989).
Langin et al., "[3H]RX821002: a new tool for the identification of alpha 2A-adrenoceptors," Eur. J. Pharmacol., 167: 95-104 (1989).
Lankin et al., "Role of Oxidative Stress in the Genesis of Atherosclerosis and Diabetes Mellitus: A Personal Look Back on 50 Years of Research," Curr. Aging Sci. 10:18 (2017).
Le et al., "Ligand binding and functional properties of human angiotensin AT1 receptors in transiently and stably expressed CHO-K1 cells," Eur. J. Pharmacol., 513:35-45 (2005).
Lee et al., "Human recombinant soluble guanylyl cyclase: expression, purification, and regulation," Proc. Natl. Acad. Sci. USA, 97(20):10763-10768 (2000).
Lee et al., "The human brain cholecystokinin-B/gastrin receptor. Cloning and characterization," J. Biol. Chem., 268 : 8164-8169 (1993).
Leibundgut et al., "Oxidation-specific epitopes and immunological responses: Translational biotheranostic implications for atherosclerosis," Current Opinion in Pharmacology, 13(2):168-179 (2013).
Leonardi et al., "Correlation Between Conjunctival Provocation Test (CPT) and Systemic Allergometric Tests in Allergic Conjunctivitis," Eye, 4:760-764 (1990).
Leurs et al., "Pharmacological characterization of the human histamine H2 receptor stably expressed in Chinese hamster ovary cells," Brit. J. Pharmacol., 112: 847-854 (1994).
Levin et al., "The myocardium-protective Gly-49 variant of the beta 1-adrenergic receptor exhibits constitutive activity and increased desensitization and down-regulation," J. Biol.Chem., 277:30429-30435 (2002).
Lewin et al., "meta- and para-isothiocyanato-t-butylbicycloorthobenzoate: irreversible ligands of the gamma-aminobutyric acid-regulated chloride ionophore," Mol. Pharmacol., 35:189-194 (1989).
Li et al., "Effect of Vitamin A Supplementation on Rhodopsin Mutants Threonine-17 → Methionine and Proline-347 → Serine in Transgenic Mice and in Cell Cultures," Proc Natl Acad Sci USA, 95(20):11933-11938 (1998).
Liu et al., "Comparison of human, mouse, rat, and guinea pig histamine H4 receptors reveals substantial pharmacological species variation," J. Pharmacol. Exp. Ther., 299:121-130 (2001).
Loftsson et al., "Cyclodextrins in Eye Drop Formulations: Enhances Topical Delivery of Corticosteroids to the Eye," Acta Ophthalmologica Scandinavica, 80(2):144-150 (2002).
Loftsson et al., "Cyclodextrin Microparticles for Drug Delivery to the Posterior Segment of the Eye: Aqueous Dexamethasone Eye Drops," Journal of Pharmacy and Pharmacology, 59(5):629-635 (2007).
Lovenberg et al., "Cloning and functional expression of the human histamine H3 receptor," Mol. Pharmacol., 55:1101-1107 (1999).
Lukas, R.J., "Characterization of curaremimetic neurotoxin binding sites on membrane fractions derived from the human medulloblastoma clonal line, TE671," J. Neurochem., 46:1936-1941 (1986).
Luthin et al., "Characterization of two affinity states of adenosine A2a receptors with a new radioligand, 2-[2-(4-amino-3-[125I]iodophenyl)ethylamino]adenosine," Mol. Pharmacol., 47:307-313 (1995).
MacDonald et al., "Molecular characterization of the melanin-concentrating hormone/receptor complex: identification of critical residues involved in binding and activation," Mol. Pharmacol., 58:217-225 (2000).

MacKenzie et al., "Characterization of the human dopamine D3 receptor expressed in transfected cell lines," Eur. J. Pharmacol., 266:79-85 (1994).
Maguire et al., "Orphan-receptor ligand human urotensin II: receptor localization in human tissues and comparison of vasoconstrictor responses with endothelin-1," Brit. J. Pharmacol., 131:441-446 (2000).
Mantey et al., "Discovery of a high affinity radioligand for the human orphan receptor, bombesin receptor subtype 3, which demonstrates that it has a unique pharmacology compared with other mammalian bombesin receptors," J. Biol. Chem., 272:26062-26071 (1997).
Marnett, "Oxy radicals, lipid peroxidation and DNA damage," Toxicology, 181-182:219-222 (2002).
Martin et al., "Molecular cloning and functional characterization of murine cysteinyl-leukotriene 1 (CysLT(1)) receptors.," Biochem. Pharmacol., 62:1193-1200 (2001).
Matern et al.,"Seizures in a boy with succinic semialdehyde dehydrogenase deficiency treated with vigabatrin (gamma-vinyl-GABA)," J Inherit Metab Dis., 19(3):313-8 (1996).
Maurice et al., "Advances in targeting cyclic nucleotide phosphodiesterases," Nat Rev Drug Discov., 13:290-314(2014).
McCord et al., "Superoxide dismutase. An enzymic function for erythrocuprein (hemocuprein).," J. Biol. Chem., 244: 6049-6055 (1969).
McGinnity et al., "Evaluation of fresh and cryopreserved hepatocytes as in vitro drug metabolism tools for the prediction of metabolic clearance." Drug Metab. Dispos., 32(11):1247-1253 (2004).
McLaurin et al., "Phase 3 Randomized Double-Masked Study of Efficacy and Safety of Once-Daily 0.77% Olopatadine Hydrochloride Ophthalmic Solution in Subjects with Allergic Conjunctivitis Using the Conjunctival Allergen Challenge Model," Clinical Science, 34(10):1245-1251 (2015).
Medline Plus. Macular Degeneration—age-related. (6 pages) (2013).
Meijer et al., "Biochemical and cellular effects of roscovitine, a potent and selective inhibitor of the cyclin-dependent kinases cdc2, cdk2 and cdk5," Eur. J. Biochem., 243:527-536 (1997).
Meng et al., "Cloning and pharmacological characterization of a rat kappa opioid receptor," Proc. Natl. Acad. Sci. U.S.A., 90:9954-9958 (1993).
Mialet et al., "Isolation of the serotoninergic 5-HT4(e) receptor from human heart and comparative analysis of its pharmacological profile in C6-glial and CHO cell lines," Brit. J. Pharmacol., 129:771-781 (2000).
Mittl et al., "Structure of recombinant human CPP32 in complex with the tetrapeptide acetyl-Asp-Val-Ala-Asp fluoromethyl ketone," J. Biol. Chem., 272:6539-6547 (1997).
Monaghan et el., "The distribution of [3H]kainic acid binding sites in rat CNS as determined by autoradiography," Brain Res., 252:91-100 (1982).
Monsma et al., "Cloning and expression of a novel serotonin receptor with high affinity for tricyclic psychotropic drugs," Mol. Pharmacol., 43:320-327 (1993).
Mulheron et al., "Human 5-HT1A receptor expressed in insect cells activates endogenous G(o)-like G protein(s)," J. Biol. Chem., 269:12954-12962 (1994).
Muller-Enoch et al., "[6.7-Dihydroxycoumarin (Aesculetin) as a substrate for catechol-o-methyltransferase (author's transl)]," Z. Naturforsch., 31:280-284 (1976).
Munro et al., "Molecular characterization of a peripheral receptor for cannabinoids," Nature, 365:61-65 (1993.
Murphy et al., "Characterization of quisqualate recognition sites in rat brain tissue using DL-[3H]alpha-amino-3-hydroxy-5-methylisoxazole-4-propionic acid (AMPA) and a filtration assay," Neurochem. Res., 12:775-781 (1987).
Nagase et al., "Design and characterization of a fluorogenic substrate selectively hydrolyzed by stromelysin 1 (matrix metalloproteinase-3)," J. Biol. Chem., 269:20952-20957 (1994).
Nakamura et al., "Involvement of Oxidative Stress on Corneal Epithelial Alterations in a Blink-Suppressed Dry Eye," Investigative Ophthalmology and Visual Science, 48(4):1552-1558 (2007).

(56) References Cited

OTHER PUBLICATIONS

Negre-Salvayre et al., "Advanced Lipid Peroxidation End Products in Oxidative Damage to Proteins. Potential Role in Diseases and Therapeutic Prospects for the Inhibitors," Br J Pharmacol, 153(1):6-20 (2008).
Nema et al., "Excipients and Their Use in injectable Products," PDA J Pharm Sci Technol, 51(4):166-171 (1997).
Nerurkar et al., "13-Aryl-Glutaconic Acids. II. Imides of Certain 13-aryl-Glutaconic and Glutaric Acids," J Org Chem, 24(12):2055-2056 (1959).
Niwa et al., "Protein oxidative damage in the stratum corneum: Evidence for a link between environmental oxidants and the changing prevalence and nature of atopic dermatitis in Japan," Br J Dermatol., 149:248 (2003).
Nociari et al., "Beta cyclodextrins bind, stabilize, and remove lipofuscin bisretinoids from retinal pigment epithelium," Proc Natl Acad Sci U.S.A E1402-E1408 (2014).
Noorwez et al., "Pharmacological Chaperone-mediated in Vivo Folding and Stablization of the P23H-Opsin Mutant Associated with Autosomal Dominant Retinitis Pigmentosa," J Biol Chem, 278:14442-14450 (2003).
Obourn et al., "Hormone- and DNA-binding mechanisms of the recombinant human estrogen receptor," Biochemistry 32(24):6229 (1993).
Organisciak et al., "Susceptibility to Retinal Light Damage in Transgenic Rats with Rhodopsin Mutations," Invest Ophthalmol Vis Sci, 44(2):486-492 (2003).
Pacholczyk et al., "Expression cloning of a cocaine- and antidepressant-sensitive human noradrenaline transporter," Nature, 350:350-354 (1991).
Pal et al., "Sulfur mustard analog induces oxidative stress and activates signaling cascades in the skin of SKH-1 hairless mice," Free Radic Biol Med., 47(11):1640-51 (2009).
Palchaudhuri et al., "Corticotropin-releasing factor receptor type 1 from Tupaia belangeri—cloning, functional expression and tissue distribution," Eur. J. Biochem., 258:78-84 (1998).
Parish et al., "Isolation and One-Step Preparation of A2E and iso-A2E, Fluorophores from Human Retinal Pigment Epithelium," Proc Natl Acad Sci USA, 95(25):14609-14613 (1998).
Park et al., "Homogeneous proximity tyrosine kinase assays: scintillation proximity assay versus homogeneous time-resolved fluorescence," Anal. Biochem., 269:94-104 (1999).
Parracho et al., "Differences between the gut microflora of children with autistic spectrum disorders and that of healthy children," Journal of Medical Microbiology, 54:987-991 (2005).
Patel C.Y., "Subtype selectivity of peptide analogs for all five cloned human somatostatin receptors (hsstr 1-5)," Endocrinology, 135:2814-2817 (1994).
Pearl et al., "Inherited disorders of gamma-aminobutyric acid metabolism and advances in ALDH5A1 mutation identification," Dev Med Child Neurol., 57(7):611-617 (2015).
Pellock, "Balancing clinical benefits of vigabatrin with its associated risk of vision loss," Acta Neurologica. Scandinavica. Supplementum., 124(s192):83-91 (2011).
Peralta et al., "Distinct primary structures, ligand-binding properties and tissue-specific expression of four human muscarinic acetylcholine receptors," EMBO. J.,.6:3923-3929 (1987).
Petroski et al., "Selective labeling of embryonic neurons cultured on astrocyte monolayers with 5(6)-carboxyfluorescein diacetate (CFDA)," Journal of Neuroscience Methods, 52(1):23-32 (1994).
Pickering,D.S., "Pharmacological characterization of melatonin binding sites in Syrian hamster hypothalamus," Eur. J. Pharmacol., 175:71-77 (1990).
Pontikis et al., "Cyclodextrin alleviates neuronal storage of cholesterol in Niemann-Pick C disease without evidence of detectable blood-brain barrier permeability," Journal of Inherited Metabolic Disease, 36(3):491-498 (2013).
Pozzi et al., "Modification of Collagen IV by Glucose or Methylglyoxal Alters Distinct Mesangial Cell Function," Journal of the American Society of Nephrology, 20:2119-2125 (2009).

Pristupa et al., "Pharmacological heterogeneity of the cloned and native human dopamine transporter: disassociation of [3H]WIN 35,428 and [3H]GBR 12,935 binding.," Mol. Pharmacol., 45:125-135 (1994).
Pruneau et al., "LF 16.0335, a novel potent and selective nonpeptide antagonist of the human bradykinin B2 receptor," Brit. J. Pharmacol., 125:365-372 (1998).
PubChem, SCHEMBL16316728, CID 117758222, Feb. 23, 2016 (13 pages).
Pufahl et al., "Development of a fluorescence-based enzyme assay of human 5-lipoxygenase," Anal. Biochem., 364:204-212 (2007).
Radu et al., "Treatment with Isotretinoin Inhibits Lipofuscin Accumulation in a Mouse Model of Recessive Stargardt's Macular Degeneration," Proc Natl Acad Sci USA, 100(8):4742-4747(2003).
Radu et al., "Isotretinoin treatment inhibits lipofuscin accumulation in a mouse model of recessive Stargardt's macular degeneration," Novartis Foundation Symposium, 255(51-63):177-178 (2004).
Rapp et al., "The Effects of Local Anaesthetics on Retinal Function," Vision Res, 22(9):1097-1103 (1982).
Reed, "Lipid peroxidation and neurodegenerative disease," Free Radical Biology and Medicine, 51(7):1302-1319 (2011).
Rees et al., "Cloning and characterisation of the human 5-HT5A serotonin receptor," FEBS Lett., 355:242-246 (1994).
Reynolds et al., "(-)-[3H] desmethoxyverapamil labels multiple calcium channel modulator receptors in brain and skeletal muscle membranes: differentiation by temperature and dihydropyridines," J. Pharmacol. Exp. Ther., 237: 731-738 (1986).
Rinaldi-Carmona et al., "Characterization of two cloned human CB1 cannabinoid receptor isoforms," J. Pharmacol. Exp. Ther., 278:871-878 (1996).
Rivkees et al., "Identification of domains of the human A1 adenosine receptor that are important for binding receptor subtype-selective ligands using chimeric A1/A2a adenosine receptors," J. Biol. Chem., 270:20485-20490 (1995).
Rizzo et al., "Ichthyosis in Sjögren-Larsson syndrome reflects defective barrier function due to abnormal lamellar body structure and secretion," Arch Dermatol Res, 302(6):443-451 (2010).
Rizzo et al., "Sjögren-Larsson syndrome: molecular genetics and biochemical pathogenesis of fatty aldehyde dehydrogenase deficiency," Mol Genet Metab. 90(1):1-9 (2007).
Rizzo et al., "Endogenous antioxidants and radical scavengers," Advances in Experimental Medicine and Biology, 698:52-6 (2010).
Roat, "Keratoconjunctivitis Sicca," Merck Manual Professional Version, 5 pages (2016), Available at: https://www.merckmanuals.com/professional/eye-disorders/corneal-disorders/keratoconjunctivitis-sicca.
Roat, "Allergic Conjunctivitis," Merck Manual Professional Version, 3 pages (2016), Available at: https://www.merckmanuals.com/professional/eye-disorders/conjunctival-and-scleral-disorders/allergic-conjunctivitis.
Roat, "Ocular Mucous Membrane Pemphigoid," Merck Manual Professional Version, 3 pages (2016), Available at: https://www.merckmanuals.com/professional/eye-disorders/conjunctival-and-scleral-disorders/ocular-mucous-membrane-pemphigoid.
Roat, "Scleritis," Merck Manual Professional Version, 3 pages (2016), Available at: https://www.merckmanuals.com/professional/eye-disorders/conjunctival-and-scleral-disorders/scleritis.
Rohrer et al., "Cloning and characterization of a fourth human somatostatin receptor," Proc. Natl. Acad. Sci. U.S.A. , 90:4196-4200 (1993).
Sahi et al., "Hepatocytes as a tool in drug metabolism, transport and safety evaluations in drug discovery." Current Drug Discov. Technol., 7(3):188-198 (2010).
Salvatore et al., "Molecular cloning and characterization of the human A3 adenosine receptor," Proc. Natl. Acad. Sci. U.S.A., 90:10365-10369 (1993).
Samsonov et al., "Impact of Atherosclerosis- and Diabetes-Related Dicarbonyls on Vascular Endothelial Permeability: A Comparative Assessment," Oxid. Med. Cell Longev. Article 1625130 (2017).
Sarafian et al., "Synergistic cytotoxicity of Delta(9)-tetrahydrocannabinol and butylated hydroxyanisole," Toxicology Letters, 133(2-3):171-179 (2002).

(56) References Cited

OTHER PUBLICATIONS

Sarup et al., "Resolution of high and low affinity progesterone receptors from human breast carcinoma T47D cells," J. Biol. Chem., 263:5624-5633 (1988).
Sayed et al., "Metabolic Activation of R,S-1-(Tetrahydro-2-turanyl)-5-fluorouracil (Ftorafur) to 5-fluorouracil by Soluble Enzymes," Cancer Research, 43:4039-4044 (1983).
Schioth et al., "Characterization of the binding of MSH-B, HB-228, GHRP-6 and 153N-6 to the human melanocortin receptor subtypes," Neuropeptides, 31:565-571 (1997).
Schwinn et al., "Molecular cloning and expression of the cDNA for a novel alpha 1-adrenergic receptor subtype," J. Biol. Chem., 265:8183-8189 (1990).
Sciuto et al., "Therapeutic Treatments of Phosgene-Induced Lung Injury," Inhal Toxicol, 16(8):565-580 (2004).
Search Report and Written Opinion issued by the Intellectual Property Office of Singapore for Singapore Patent Application No. 11201505587Y dated Jul. 12, 2016 (12 pages).
Search Report and Written Opinion issued by the Intellectual Property Office of Singapore for Singapore Patent Application No. 11201505587Y dated Aug. 1, 2016 (12 pages).
Search Report and Written Opinion issued by the Intellectual Property Office of Singapore for Singapore Patent Application No. 11201505599Y dated Sep. 26, 2016 (11 pages).
Shank et al., "Ion and temperature effects on the binding of gamma-aminobutyrate to its receptors and the high-affinity transport system," J. Neurochem., 54:2007-2015 (1990).
Shen et al., "Molecular cloning and expression of a 5-hydroxytryptamine7 serotonin receptor subtype," J. Biol. Chem., 268:18200-18204 (1993).
Sherman et al., "Cellular Defenses Against Unfolded Proteins: A Cell Biologist Thinks about Neurodegenerative Diseases," Neuron, 29(1):15-32 (2001).
Shipp et al., "Common acute lymphoblastic leukemia antigen (CALLA) is active neutral endopeptidase 24.11 ("enkephalinase"): direct evidence by cDNA transfection analysis," Proc Natl Acad Sci USA. 86:297 (1989).
Shoemaker et al., "[3H]diltiazem binding to calcium channel antagonists recognition sites in rat cerebral cortex," Eur. J. Pharmacol., 111:273-277 (1985).
Siegrist et al., "Radioreceptor assay for alpha-MSH using mouse B16 melanoma cells+.," J. Recep. Res., 8:323-343 (1988).
Sieving et al., "Inhibition of the Visual Cycle in vivo by 13-cis Retinoic Acid Protects from Light Damage and Provides a Mechanism for Night Blindness in Isotretinoin Therapy," Proc Natl Acad Sci USA, 98(4):1835-1840 (2001).
Sills et al., "[3H]CGP 39653: a new N-methyl-D-aspartate antagonist radioligand with low nanomolar affinity in rat brain," Eur. J. Pharmacol., 192:19-24 (1991).
Simonin et al., "The human delta-opioid receptor: genomic organization, cDNA cloning, functional expression, and distribution in human brain," Mol. Pharmacol., 46:1015-1021 (1994).
Smit et al., "Regulation of the human histamine H1 receptor stably expressed in Chinese hamster ovary cells," Brit. J. Pharmacol., 117:1071-1080 (1996).
Snead et al., "Gamma-hydroxybutyric acid," New England Journal of Medicine, 352(26):2721-2732 (2005).
Snell et al., "Novel structure having antagonist actions at both the glycine site of the N-Methyl-D-Aspartate receptor and neuronal voltage-sensitive sodium channels. Biochemical, electrophysiological, and behavioral characterization," J Pharmacol Exp Ther, 292(1):215-227 (2000).
Sparrow et al. "Phospholipid meets all-trans-retinal: the making of RPE bisretmoids," Journal of Lipid Research, 51: 247-261 (2010).
Speth et al., "Benzodiazepine receptors: temperature dependence of [3H]flunitrazepam binding," Life Sci., 24:351-358 (1979).
Stehle et al., "Molecular cloning and expression of the cDNA for a novel A2-adenosine receptor subtype," Mol. Endocrinol., 6:384-393 (1992).

Struys et al., "Determination of the GABA analogue succinic semialdehyde in urine and cerebrospinal fluid by dinitrophenylhydrazine derivatization and liquid chromatography-tandem mass spectrometry: application to SSADH deficiency," J Inherit Metab Dis., 28(6):913-20 (2005).
Struys et al., "Metabolism of gamma-hydroxybutyrate to d-2-hydroxyglutarate in mammals. further evidence for d-2-hydroxyglutarate transhydrogenase," Metabolism, 55(3):353-8 (2006).
Study showing effect of ADX-102 on Fibrotic Changes in Cardiac Fibroblasts Following Cell Stress, American Society for Cell Biology Annual Meeting, Dec. 3-7, 2016 (2 pages).
Sus et al., "Uber die Lichtreaktion der o-Chinondiazide V Mitteilungl) Ubergange heterocyclischer 6-Ringe in heterocyclische 5-Ringe," Liebigs Ann. Chem. 583:150 (1953).
Tahara et al., "Pharmacological characterization of the human vasopressin receptor subtypes stably expressed in Chinese hamster ovary cells," Brit. J. Pharmacol., 125:1463-1470 (1998).
Tang et al., "Effects of four penetration enhancers on corneal permeability of drugs in vitro," Journal of Pharmaceutical Sciences, 83(1):85-90 (1994).
Tatsumi et al., "Pharmacological profile of neuroleptics at human monoamine transporters," Eur. J. Pharmacol., 368 : 277-283 (1999).
Tayeh et al., "Macrophage oxidation of L-arginine to nitric oxide, nitrite, and nitrate. Tetrahydrobiopterin is required as a cofactor," J. Biol. Chem., 264:19654-19658 (1989).
Tewari-Singh et al., "Silibinin attenuates sulfur mustard analog-induced skin injury by targeting multiple pathways connecting oxidative stress and inflammation," PLoS One 7(9):e46149 (2012).
Tian et al., "First total synthesis and determination of the absolute configuration of 1-N-methyl-3-methylamino-[N-butanoicacid-3-(9-methyl-8-propen-7-one)-amide]-benzo[f][1,7]naphthyridine-2-one, a novel benzonaphthyridine alkaloid," Tetrahedron Letters, 53:4892-4895 (2012).
Tikly et al., "Lipid peroxidation and trace elements in systemic sclerosis," Clinical Rheumatology, 25(3):320-324 (2006).
Torkildsen et al., "Efficacy and safety of olopatadine hydrochloride 0.77% in patients with allergic conjunctivitis using a conjunctival allergen-challenge model," Clinical Ophthalmology, 9:1703-1713 (2015).
Toth et al., "A simple, continuous fluorometric assay for HIV protease," Int. J. Pept. Protein Res., 36:544-550 (1990).
Tsugeno et al., "Regions of the molecule responsible for substrate specificity of monoamine oxidase A and B: a chimeric enzyme analysis," J. Biochem., 118 (5) 974-80 (1995).
Tsuzuki et al., "Molecular cloning and expression of the gene encoding human angiotensin II type 2 receptor.," Biochem. Biophys. Res. Commun., 200:1449-1454 (1994).
Tukozkan et al., "Measurement of Total Malondialdehyde in Plasma and tissues by High-Performance Liquid Chromatography and Thiobarbituric Acid Assay," Firat Tip Dergisi, 11(2):88-92 (2006).
Ueda et al., "Evaluation of a Sulfobutyl Ether 13-Cyclodextrin as a Solubilizing/Stabilizing Agent for Several Drugs," Drug Dev Ind Pharm, 24(9):863-867(1998).
Upadhyaya et al., "The sphingolipid degradation product trans-2-hexadecenal forms adducts with DNA," Biochem Biophy Res Comm., 424(1):18-21 (2012).
Vanachayangkul et al., "Inhibition of heme peroxidases by melamine," Enzyme Research, 2012:416062 (2012).
Vignon et al., "[3H]thienyl-phencyclidine ([3H]TCP) binds to two different sites in rat brain. Localization by autoradiographic and biochemical techniques," Brain Res., 378:133-141 (1986).
Vlaskina et al., "Novel Synthesis of Substituted Benzimidazoles by Reduction of Esters of 4-Alkylamino-3,5-dinitrobenzoic Acids by Tin Chloride," Chemistry of Heterocyclic Compounds, vol. 40(4):523-524 (2004).
Vogel et al, "Thirty years beyond discovery—clinical trials in succinic semialdehyde dehydrogenase deficiency, a disorder of GABA metabolism," J Inherit Metab Dis., 36(3):401-10 (2013).
Voziyan et al., "A Post-Amadori Inhibitor Pyridoxamine also Inhibits Chemical Modification of Proteins by Scavenging Carbonyl Intermediates for Carbohydrate and Lipid Degradation," J Biol Chem, 277(5):3397-3403 (2002).

(56) References Cited

OTHER PUBLICATIONS

Wagner et al., "Omega-conotoxin GVIA binding to a high-affinity receptor in brain: characterization, calcium sensitivity, and solubilization," J. Neurosci., 8:3354-3359 (1988).
Wang et al., "Markers of oxidative and nitrosative stress in systemic lupus erythematosus: correlation with disease activity," Arthritis and Rheumatism, 62(7):2064-2072 (2010).
Wang et al., "Human mu opiate receptor. cDNA and genomic clones, pharmacologic characterization and chromosomal assignment," FEBS Lett., 338:217-222 (1994).
Wang, X.K., "Pharmacological study on recombinant human GABA-A receptor complex containing alpha5 (leucine155 to valine) combined with beta3gamma2s subunits," Acta. Pharmacol. Sin., 22:521-523 (2001).
Wang et al., "A facile one-pot synthesis of 2-substituted-3-aminoquinolines: Preparation of benzo[b]naphthyridine-3-carbonitriles," Tetrahedron, 60(13):2937-2942 (2004).
Waslidge et al., "A colorimetric method for the determination of lipoxygenase activity suitable for use in a high throughput assay format," Anal. Biochem., 231:354-358 (1995).
Weishaar et al., "Multiple molecular forms of cyclic nucleotide phosphodiesterase in cardiac and smooth muscle and in platelets. Isolation, characterization, and effects of various reference phosphodiesterase inhibitors and cardiotonic agents," Biochem. Pharmacol., 35:787-800 (1986).
Weng et al., "Insights into the Function of Rim Protein in Photoreceptors and Etiology of Stargardt's Disease from the Phenotype in abcr Knockout Mice," Cell, 98(1):13-23 (1999).
Westphal et al., "Reactions with Plyridinium Pyruvic Acid Esters," Pharmazie, 31(11):770-773 (1976).
Wieland et al., "Subtype selectivity and antagonistic profile of the nonpeptide Y1 receptor antagonist BIBP 3226," J. Pharmacol. Exp. Ther., 275:143-149 (1995).
Witt-Enderby et al., "Characterization and regulation of the human ML1A melatonin receptor stably expressed in Chinese hamster ovary cells," Mol. Pharmacol., 50:166-174 (1996).
Wolkenberg et al., "Design, synthesis, and evaluation of novel 3,6-diaryl-4-aminoalkoxyquinolines as selective agonists of somatostatin receptor subtype 2," J Med Chem, 54(7):2351-2358 (2011).
Wood et al., "The concept of "aldehyde load" in neurodegenerative mechanisms: cytotoxicity of the polyamine degradation products hydrogen peroxide, acrolein, 3-ammopropanal, 3-acetamidiorioanal and 4-aminobutanal in a retinal ganglion cell line," Brain Research, 1145:150-156 (2007).
Wood et al., "Aldehyde Load in Ischemia-Reperfusion Brain Injury: Neuroprotection by Neutralization of reactive Aldehydes with Phenelzine," Brain Res, 1122(1):184-190 (2006).
Wurch et al., "Sequence and functional analysis of cloned guinea pig and rat serotonin 5-HT1D receptors: common pharmacological features within the 5-HT1D receptor subfamily," J. Neurochem., 68:410-418 (1997).
Yarnell, "Light Flips the Lipid Switch: Palmitoylation—the reversible attachment of palmitate to proteins—gets a new role in vision," C&EN, 82(29):22-23 (2004).
Yokomizo et al., "Hydroxyeicosanoids bind to and activate the low affinity leukotriene B4 receptor, BLT2," J. Biol. Chem., 276:12454-12459 (2001).
Zagol-Ikapitte et al., "Characterization of scavengers of y-ketoaldehydes that do not inhibit prostaglandin biosynthesis," Chem Res Toxicol, 23(1):240-250 (2010).
Zarkovic "4-hydroxynonenal and neurodegenerative diseases," Molecular Aspects of Medicine, 24(4-5):293-303 (2003).
Zava et al., "Androgen receptor assay with [3H]methyltrienolone (R1881) in the presence of progesterone receptors," Endocrinology, 104:1007-1012 (1979).
Zhou et al., "Mechanisms for the induction of HNE- MDA- and AGE-adducts, RAGE and VEGF in retinal pigment epithelial cells," Exp Eye Res., 80(4):567-80 (2005).

Zhou et al., "Chemical and biological evidence for base propenals as the major source of the endogenous M1dG adduct in cellular DNA," J Biol Chem., 280(27):25377-82 (2005).
Zhou et al, "Cloning and expression of human and rat D1 dopamine receptors," Nature, 347:76-80 (1990).
U.S. Appl. No. 15/437,699 of Jordan et al., filed Feb. 21, 2017.
U.S. Appl. No. 15/754,065 of Brady et al., filed Feb. 21, 2018.
U.S. Appl. No. 16/157,069 of MacDonald et al., filed Oct. 10, 2018.
U.S. Appl. No. 16/168,309 of Chabala et al., filed Oct. 23, 2018.
Aldeyra Press Release Phase II Allergic Conjunctivitis, Feb. 29, 2016 (3 pages).
Aldeyra Press Release—Positive Results From Phase II Clinical Trial in Subjects With Noninfectious Anterior Uveitis, May 9, 2016 (4 pages).
Ao et al., "Methyl-β-Cyclodextrin Impairs the Monocyte-Adhering Ability of Endothelial Cells by Down-Regulating Adhesion Molecules and Caveolae and Reorganizing the Actin Cytoskeleton," Biol Pharm Bull, 39(6):1029-1034 (2016).
Axelsson et al., "Experimental colitis induced by dextran sulphate sodium in mice: beneficial effects of sulphasalazine and olsalazine," Aliment Pharmacol Ther, 12:925-934 (1998).
Balci et al., "Effects of computer monitor-emitted radiation on oxidant/antioxidant balance in cornea and lens from rats," Molec Vis, 15:2521-2525 (2009).
Balci et al., "Investigation of oxidative stress in pterygium tissue," Molecular Vision, 17:443-447 (Feb. 2011).
Baltatzis et al., "Mycophenolate mofetil as an immunomodulatory agent in the treatment of chronic ocular inflammatory disorders," Ophthalmology, 110(5):1061-5 (May 2003).
Bermudez et al., "Thermosensitive poloxamer-based injectables as controlled drug release platforms for veterinary use: Development and in-vitro evaluation," Intl Res J Pharmacy Pharmacol, 1(6):109-118 (Sep. 2011).
Boyer et al., "Lipofuscin and N-Retinylidene-N-Retinylethanolamine (A2E) Accumulate in Retinal Pigment Epithelium in Absence of Light Exposure," J Biol Chem, 287(26):22276-22286 (Jun. 2012).
Brewitt et al., "Dry Eye Disease—The Scale of the Problem," Survey of Ophthalmol, 45(Suppl 2):S199-S2 (Mar. 2001).
Burstein, "The effects of topical drugs and preservatives on the tears and corneal epithelium in dry eye," Transactions of the Ophthalmological Societies of the United Kingdom, 104:402-409 (1985).
Cejkova et al., "The role of conjunctival epithelial cell xanthine oxidoreductase/xanthine oxidase in oxidative reactions on the ocular surface of dry eye patients with Sjögren's syndrome," Histol Histopathol 22(9):997-1003 (Sep. 2007).
Chen et al., "Methazolamide Calcium Phosphate Nanoparticles in an Ocular Delivery System," Pharm Soc Japan, 130(3):419-24 (2010).
Chiarpotto et al., "Role of 4-hydroxy-2,3-nonenal in the pathogenesis of fibrosis," Biofactors, 24(1-4):229-36 (2005).
Choi et al., "Expression of Lipid Peroxidation Markers in the Tear Film and Ocular Surface of Patients with Non-Sjogren Syndrome: Potential Biomarkers for Dry Eye Disease," Curr Eye Res, 41(9):1143-11 (2016).
Cooper et al., "Clinicopathologic study of dextran sulfate sodium experimental murine colitis," Lab Invest, 69(2):238-49 (Aug. 1993).
Cullen et al, "Administration of the small molecule aldehyde trap NS2 in a hamster model of radiation-induced oral mucositis," ISOO 2015 Annual Meeting Abstract, Support Care Cancer, 23 (Suppl 1):S107 (Jun. 2015).
Cullen et al, "The small molecule aldehyde trap NS2 exhibits potent anti-inflammatory activity in three murine models of inflammation," AAAAI Annual Meeting Abstract, 1 page (Feb. 2015).
Demir et al., "The protective effect of alpha-lipoic acid against oxidative damage in rabbit conjunctiva and cornea exposed to ultraviolet radiation," Ophthalmologica, 219(1):49-53 (Jan.-Feb. 2005).
Demir et al., "Oxidative stress of intracameral lidocaine and levobupivacaine on ocular tissues," Br J Ophthalmol, 94(8):1083-7 (Aug. 2010).
Egger, et al., "Keratinocyte growth factor ameliorates dextran sodium sulfate colitis in mice," Dig Dis Sci, 44(4): 836-44 (Apr. 1999).

(56) References Cited

OTHER PUBLICATIONS

Esterbauer et al., "Chemistry and Biochemistry of 4-Hydroxynonenal, Malonaldehyde and Related Aldehydes," Free Radic Biol Med, 11:81-128 (1991).
Friesen et al., "Optimization of a Tertiary Alcohol Series of Phosphodiesterasete-4 (PDE4) Inhibitors: Structure-Activity Relationship Related to PDE4 Inhibition and Human Ether-a-go-go Related Gene Potassium Channel Binding Affinity," J. Med. Chem., 46(12):2413-2426 (2003).
Full 1H NMR assignment for RAL-NS2 in CDCIJ, submitted to Japanese Patent Office Mar. 1, 2012.
Gasper et al., "2-Hydroxypropyl-beta-cyclodextrin (HPβCD) reduces age-related lipofuscin accumulation through a cholesterol-associated pathway," Scientific Reports, 7(2197):1-7 (2017).
Gibson et al., "The Aldehyde Trap NS2 Mitigates Dense Haze in a Rabbit Model of Photorefractive Keratectomy" ARVO Annual Meeting Abstract, 1 page (Jun. 2015).
Gomez, "Dimethyltin(IV) 2,6-disubstituted pyridine complexes," J. Organometallic Chemistry, 672(2):115-122 (2003).
Grob et al., "Die Synthese von 5-Oxy-benz(cd)indolin and dessen Umpagerung in 5-Keto-1,3,4,5-tetrahydro-benz(cd)indol," Helvetica Chimica Acta, Verlag Helvetica Chimica Acta, CH, 33(6):1796-1808 (1950).
Grob et al., "Die Synthese von 5-Oxy-benz(cd)indolin and dessen Umpagerung in 5-Keto-1,3,4,5-tetrahydro-benz(cd)indol," Helvetica Chimica Acta, Verlag Helvetica Chimica Acta, CH, 33(6):1796-1808 (1950) [Machine Translation].
Gromachevskaya et al., "4H-3,1-benzoxazines. 2. Synthesis of 2,4-substituted 1,2-dihydro-4H-3,1-benzoxazines," Chemistry of Heterocyclic Compounds, 24(6):692-697 (Jun. 1988).
Grotto et al., "Importance of the lipid peroxidation biomarkers and methodological aspects for malondialdehyde quantification," Quim Nova, 32(1):169-174 (2009).
Halilovic et al., "ADX-103, a Novel Small Molecule Aldehyde Sequestering Agent, Decreases Retinal Edema and Inflammation in a Rat Model of Diabetic Macular Edema," ARVO Annual Meeting Abstract, 2 pages (Jul. 2018).
Herbort et al., "Endotoxin-induced uveitis in the rat," Graefe's Arch Clin Exp Ophthalmol, 226:553-8 (1988).
Horner et al., "Analogs of 3-Amino-7-chloro-1,2,4-benzotriazine 1-Oxide as Antimalarial Agents," J. Med. Chem., 11(5):946-949 (1968).
International Search Report and Written Opinion issued by the United States Patent and Trademark Office as International Searching Authority for International Patent Application No. PCT/US2017/047958 dated Oct. 31, 2017.
International Search Report and Written Opinion issued by the United States Patent and Trademark Office as International Searching Authority for International Patent Application No. PCT/US2017/031808 dated Aug. 11, 2017.
International Search Report and Written Opinion issued by the United States Patent and Trademark Office as International Searching Authority for International Patent Application No. PCT/US2018/055310 dated Jan. 29, 2019 (9 pages).
Kenney et al., "The Cascade Hypothesis of Keratoconus," Contact Lens & Ant Eye, 26:139-146 (2003).
MacDonald et al., "ADX-102, a novel aldehyde trap, reduces nociceptive behavior in mouse models of carrageenan and CFA induced pain," Int'l Conference on Pain Research & Management Abstract, J Pain Relief, 5 (5 Suppl):50 (Oct. 2016).
MacDonald et al., "Inhibition of fibroblast activation to the myofibroblast phenotype in neonatal rat cardiac fibroblasts using a small molecule aldehyde trap," ASCB Annual Meeting Abstract, p. 2 (Dec. 2016).
MacDonald et al., "The novel aldehyde trap, ADX-102, reduces inflammation-mediated lung infiltrate in a mouse model of LPS-induced acute lung injury," 13th World Congress on Inflammation Abstract, p. 192 (Jul. 2017).
MacDonald et al., "Novel Small Molecule Aldehyde Sequestering Agents Demonstrate Broad Therapeutic Potential for Ocular Inflammation," ARVO Annual Meeting Abstract, 2 pages (Jul. 2018).

Maeda et al., "Involvement of All-trans-retinal in Acute Light-induced Retinopathy of Mice," J Biol Chem, 284(22):15173-83 (May 2009).
Maeda et al., "Primary amines protect against retinal degeneration in mouse models of retinopathies," Nat Chem Biol, 8(2):170-178 (Dec. 2011).
O'Brien et al., "Aldehyde Sources, Metabolism, Molecular Toxicity Mechanisms, and Possible Effects on Human Health," Crit Rev Toxicol, 35:609-662 (2005).
Pred Forte Prescribing Information, Allergan, 5 pages (2017).
Rauli et al., "Validation of Malondialdehyde and 4-Hydroxy-2-trans-Nonenal Measurement in Plasma by NICI-GC-MS1," J Biochem, 123:918-923 (1998).
Rizzo, "The role of fatty aldehyde dehydrogenase in epidermal structure and function" Dermato-Endocrinol, 3(2):91-99 (2011).
Roberts et al., "Basic Principles of Organic Chemistry," 2nd edition, copyright 1977 W. A. Benjamin, Inc., pp. 580-582.
Roberts et al., "Experimental Organic Chemistry—A Miniscale Approach," copyright 1994 by Saunders College Publishing, pp. 580-581 and 584-586.
Sandikci et al., "Lipid Peroxidation and Antioxidant Defence System in Patients with Active or Inactive Behcet's Disease," Acta Derm Venereol, 83:342-346 (2003).
Sasaki et al., "Retinal drug delivery using eyedrop preparations of poly-L-lysine-modified liposomes," Eur J Pharm Biopharm, 83(3):364-9 (2013).
Schaumberg et al., "Prevalence of Dry Eye Syndrome Among US Women," Am J Ophthalmol, 136(2):318-326 (Aug. 2003).
Schaumberg et al., "Prevalence of Dry Eye Disease among US Men: Estimates from the Physicians' Health Studies," Arch Ophthalmol, 127(6):763-768 (Jun. 2009).
Schramm et al., "The Cross-linked Biopolymer Hyaluronic Acid as an Artificial Vitreous Substitute," Invest Ophthalmol Vis Sci, 53(2):613-621 (Feb. 2012).
Serbecic et al., "Anti-oxidative vitamins prevent lipid-peroxidation and apoptosis in corneal endothelial cells," Cell Tissue Res, 320(3):465-75 (Jun. 2005).
Simeone et al, "Modification of the Pyridine Moiety of Nonpeptidyl Indole GnRH Receptor Antagonists," Bioorganic & Medicinal Chemistry Letters, 12(22):3329-3332 (2002).
Smith et al., "Basic pathogenic mechanisms operating in experimental models of acute anterior uveitis," Immunol Cell Biol, 76:497-512 (1998).
Spagnol et al., "Efficient synthesis of tricyclic benzobisoxazines by silica gel catalysis," J Org Chem, 2;72(5):1867-1869 (Mar. 2007).
Turk et al., "Serum anti-carbonic anhydrase antibodies and oxidant-antioxidant balance in patients with acute anterior uveitis," Ocul Immunol Inflamm, 22(2):127-32 (Apr. 2014).
Wall et al., "Plant Antitumor Agents. 30. Synthesis and Structure Activity of Novel Camptothecin Analogs," J. Med. Chem., 36(18):2689-2700 (1993).
Walter et al., "Novel Complex N-Heterocycles via Intramolecular 1,5-Electrocyclizations: 1,2,3,4,4a,5,5a,10-Octahydropyrido-[4",3":2',3']cyclobuta[1',2':4,5]pyrrolo[2,3-b]pyridines," Heterocycles, 48(8):1581-1591 (1998).
Yadav et al., "Regulation of NF-κB-Induced Inflammatory Signaling by Lipid Peroxidation-Derived Aldehydes," Oxidative Med & Cell Longev, 2013, Art ID 690545, 11 pages (2013).
Yu et al., "Injectable Chemically Crosslinked Hydrogel for the Controlled Release of Bevacizumab in Vitreous: A 6-Month In Vivo Study," Transl Vis Sci Technol, 4(2,5):1-11 (2015).
Zhang et al., "Potent nonsteroidal progesterone receptor agonists: synthesis and SAR study of 6-aryl benzoxazines," Bioorg Med Chem Lett, 12(5):787-90 (Mar. 2002).
U.S. Appl. No. 16/300,020 of Brady et al., filed Nov. 8, 2018.
U.S. Appl. No. 16/241,851 of Jordan et al., filed Jan. 7, 2019.
U.S. Appl. No. 16/262,364 of Brady et al., filed Jan. 30, 2019.
U.S. Appl. No. 16/277,865 of Brady et al., filed Feb. 15, 2019.

* cited by examiner

POLYMORPHIC COMPOUNDS AND USES THEREOF

FIELD OF THE INVENTION

This application relates to various forms and compositions, and methods, useful for treating various conditions, in which aldehyde toxicity is implicated in the pathogenesis, by the administration of small molecule therapeutics acting as a scavenger for toxic aldehydes.

BACKGROUND OF THE INVENTION

Metabolic and inflammatory processes in cells generate toxic aldehydes, such as malondialdehyde (MDA), 4-hydroxyl-2-nonenal (4HNE), glyoxal, and methylglyoxal. These aldehydes are highly reactive with proteins, carbohydrates, lipids and DNA, leading to chemically modified biological molecules, activation of inflammatory mediators such as NF-kappa B, and damage in diverse organs. For example, retinaldehyde can react with phosphatidylethanolamine (PE) to form a highly toxic compound called A2E, which is a component of lipofuscin that is believed to be involved in the development and progression of Age Related Macular Degeneration (AMD). Many bodily defense mechanisms function to remove or lower the levels of toxic aldehydes, including metabolism by aldehyde dehydrogenases, buffering by molecules such as GSH and removal from sites of potential toxicity by transporters such as ABCA4. Novel small molecule therapeutics can be used to scavenge "escaped" retinaldehyde in the retina, thus reducing A2E formation and lessening the risk of AMD (Jordan et al. (2006)).

Aldehydes are implicated in diverse pathological conditions such as dry eye, cataracts, keratoconus, Fuch's endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus), cardiovascular disorders (e.g., atherosclerosis), and conditions associated with the injurious effects of blister agents (Negre-Salvagre et al. (2008), Nakamura et al. (2007), Batista et al. (2012), Kenney et al. (2003), Int J Dermatol 43: 494 (2004), Invest Ophthalmol Vis Sci 48: 1552 (2007), Graefe's Clin Exp Ophthalmol 233: 694 (1994), Molecular Vision 18: 194 (2012)). Decreasing or eliminating aldehydes should thus ameliorate the symptoms and slow the progression of these pathological conditions.

MDA, HNE and other toxic aldehydes are generated by a myriad of metabolic mechanisms involving: fatty alcohols, sphingolipids, glycolipids, phytol, fatty acids, arachadonic acid metabolism (Rizzo (2007)), polyamine metabolism (Wood et al. (2006)), lipid peroxidation, oxidative metabolism (Buddi et al. (2002), Zhou et al. (2005)), and glucose metabolism (Pozzi et al. (2009)). Aldehydes can cross link with primary amino groups and other chemical moieties on proteins, phospholipids, carbohydrates, and DNA, leading in many cases to toxic consequences, such as mutagenesis and carcinogenesis (Marnett (2002)). MDA is associated with diseased corneas in conditions such as, keratoconus, bullous and other keratopathy, and Fuch's endothelial dystrophy (Buddi et al. (2002)). Also, a dysfunctional dermal water barrier in skin disorders, e.g., Sjögren -Larsson Syndrome, are likely connected with the accumulation of fatty aldehydes such as octadecanal and hexadecanal (Rizzo et al. (2010)). Further, increased lipid peroxidation and resultant aldehyde generation are associated with the toxic effects of blister agents (Sciuto et al. (2004) and Pal et al. (2009)).

There has been no suggestion in the art for treating the various conditions associated with toxic aldehydes, by the administration of small molecule therapeutics acting as a scavenger for aldehydes, such as MDA and/or HNE. Thus, there is a need for treating, preventing, and/or reducing a risk of a disease or disorder in which aldehyde toxicity is implicated in the pathogenesis. The present invention addresses such a need.

Accordingly, there remains a need for treating, preventing, and/or reducing a risk of a disease, disorder, or condition in which aldehyde toxicity is implicated in the pathogenesis.

SUMMARY OF THE INVENTION

It has now been found that compounds of the present invention, and compositions thereof, are useful for treating, preventing, and/or reducing a risk of a disease, disorder, or condition in which aldehyde toxicity is implicated in the pathogenesis. In general, salt forms or freebase forms, and pharmaceutically acceptable compositions thereof, are useful for treating or lessening the severity of a variety of diseases or disorders as described in detail herein. Such compounds are represented by the chemical structure below, denoted as compound A:

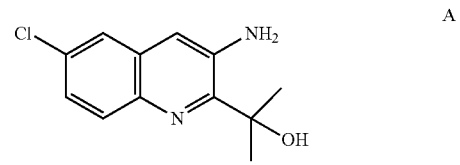 [SMILES: CC(C)(O)c1nc2ccc(Cl)cc2cc1N]

or a pharmaceutically acceptable salt thereof.

Compounds of the present invention, and pharmaceutically acceptable compositions thereof, are useful for treating a variety of diseases, disorders or conditions, associated with toxic aldehydes. Such diseases, disorders, or conditions include those described herein.

Compounds provided by this invention are also useful for the study of certain aldehydes in biology and pathological phenomena.

DETAILED DESCRIPTION OF THE INVENTION

Figure 1:
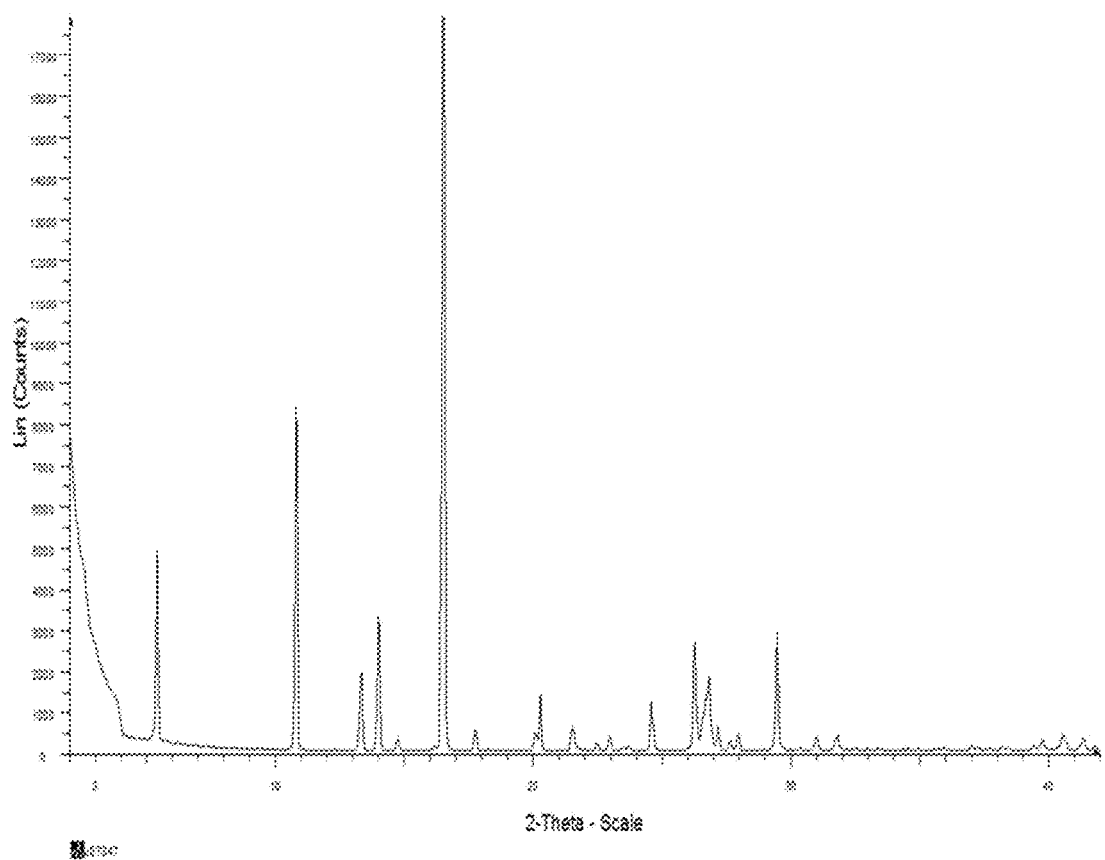
FIG. 1 depicts the XRPD pattern of Compound A, Form A.

General Description of Certain Aspects of the Invention

U.S. patent application Ser. No. 13/709,802, filed Dec. 10, 2012 and published as US 2013/0190500 on Jul. 25, 2013 ("the '500 publication," the entirety of which is hereby incorporated herein by reference), describes certain aldehyde scavenging compounds. Such compounds include compound A:

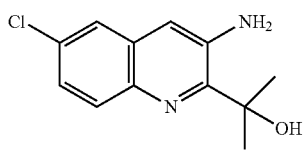

Compound A, (6-chloro-3-amino-2-(2-hydroxypropyl)-1-azanaphthalene), is designated as compound A in the '500 publication and the synthesis of compound A is described in detail at Example 5 of the '500 publication, and is reproduced herein for ease of reference.

It would be desirable to provide a solid form of compound A (e.g., as a freebase thereof or salt thereof) that imparts characteristics such as improved aqueous solubility, stability and ease of formulation. Accordingly, the present invention provides both free base forms and salt forms of compound A.

Free Base Forms of Compound A

It is contemplated that compound A can exist in a variety of physical forms. For example, compound A can be in solution, suspension, or in solid form. In certain embodiments, compound A is in solid form. When compound A is in solid form, said compound may be amorphous, crystalline, or a mixture thereof. Exemplary solid forms are described in more detail below.

In some embodiments, the present invention provides a form of compound A substantially free of impurities. As used herein, the term "substantially free of impurities" means that the compound contains no significant amount of extraneous matter. Such extraneous matter may include different forms of compound A, residual solvents, or any other impurities that may result from the preparation of, and/or isolation of, compound A. In certain embodiments, at least about 95% by weight of a form of compound A is present. In still other embodiments of the invention, at least about 99% by weight of a form of compound A is present.

According to one embodiment, a form of compound A is present in an amount of at least about 97, 97.5, 98.0, 98.5, 99, 99.5, 99.8 weight percent where the percentages are based on the total weight of the composition. According to another embodiment, a form of compound A contains no more than about 3.0 area percent HPLC of total organic impurities and, in certain embodiments, no more than about 1.5 area percent HPLC total organic impurities relative to the total area of the HPLC chromatogram. In other embodiments, a form of compound A contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for a form of compound A is also meant to include all tautomeric forms of compound A. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that compound A can exist in a variety of solid forms. Exemplary such forms include polymorphs such as those described herein.

As used herein, the term "polymorph" refers to the different crystal structures into which a compound, or a salt or solvate thereof, can crystallize.

In certain embodiments, compound A is a crystalline solid. In other embodiments, compound A is a crystalline solid substantially free of amorphous compound A. As used herein, the term "substantially free of amorphous compound A" means that the compound contains no significant amount of amorphous compound A. In certain embodiments, at least about 95% by weight of crystalline compound A is present. In still other embodiments of the invention, at least about 99% by weight of crystalline compound A is present.

It has been found that compound A can exist in at least two distinct polymorphic forms. In certain embodiments, the present invention provides a polymorphic form of compound A referred to herein as Form A. In certain embodiments, the present invention provides a polymorphic form of compound A referred to herein as Form B.

In some embodiments, compound A is amorphous. In some embodiments, compound A is amorphous, and is substantially free of crystalline compound A.

Form A of Compound A

In some embodiments, Form A of compound A has at least 1, 2, 3, 4 or 5 spectral peak(s) selected from the peaks listed in Table 1 below.

TABLE 1

XRPD Peak Positions for Form A of Compound A

| Position (°2θ) | Intensity % |
|---|---|
| 5.4 | 17.0 |
| 10.8 | 29.0 |
| 13.3 | 6.9 |
| 14.0 | 11.7 |
| 14.7 | 1.7 |
| 16.6 | 100.0 |
| 17.8 | 2.2 |
| 20.1 | 2.0 |
| 20.3 | 5.0 |
| 21.5 | 2.5 |
| 24.6 | 4.7 |
| 26.2 | 9.6 |
| 26.9 | 6.6 |
| 29.5 | 10.4 |

[1] In this and all subsequent tables, the position 2θ is within ±0.2.

In some embodiments, Form A of compound A is characterized in that it has one or more peaks in its X-ray powder diffraction (XRPD) pattern selected from those at about 5.4, about 10.8 and about 16.6 degrees 2-theta. In some embodiments, Form A of compound A is characterized in that it has two or more peaks in its X-ray powder diffraction pattern selected from those at about 5.4, about 10.8 and about 16.6 degrees 2-theta. In some embodiments, Form A of compound A is characterized in that it has all three peaks in its X-ray powder diffraction pattern selected from those at about 5.4, about 10.8 and about 16.6 degrees 2-theta. As used herein, the term "about", when used in reference to a degree 2-theta value refers to the stated value ±0.2 degree 2-theta.

In certain embodiments, the X-ray powder diffraction pattern is substantially similar to the XRPD provided in FIG. 1.

Methods for preparing Form A of compound A are described infra.

Form B of Compound A

In some embodiments, Form B of compound A has at least 1, 2, 3, 4 or 5 spectral peak(s) selected from the peaks listed in Table 2 below.

TABLE 2

XRPD Peak Positions for Form B of Compound A

| Position (°2θ) | Intensity % |
|---|---|
| 11.6 | 100.0 |
| 14.5 | 11.2 |
| 16.1 | 7.2 |
| 19.0 | 20.2 |
| 23.0 | 2.0 |
| 23.3 | 42.8 |
| 24.5 | 6.3 |
| 24.7 | 2.5 |
| 24.9 | 2.4 |

TABLE 2-continued

XRPD Peak Positions for Form B of Compound A

| Position (°2θ) | Intensity % |
|---|---|
| 27.2 | 2.2 |
| 28.6 | 2.8 |
| 31.6 | 3.8 |
| 31.8 | 2.2 |
| 35.3 | 34.3 |

[1] In this and all subsequent tables, the position 2θ is within ±0.2.

In some embodiments, Form B of compound A is characterized in that it has one or more peaks in its X-ray powder diffraction pattern selected from those at about 11.6, about 23.3 and about 35.3 degrees 2-theta. In some embodiments, Form B of compound A is characterized in that it has two or more peaks in its X-ray powder diffraction pattern selected from those at about 11.6, about 23.3 and about 35.3. In some embodiments, Form B of compound A is characterized in that it has all three peaks in its X-ray powder diffraction pattern selected from those at about 11.6, about 23.3 and about 35.3.

Figure 3:
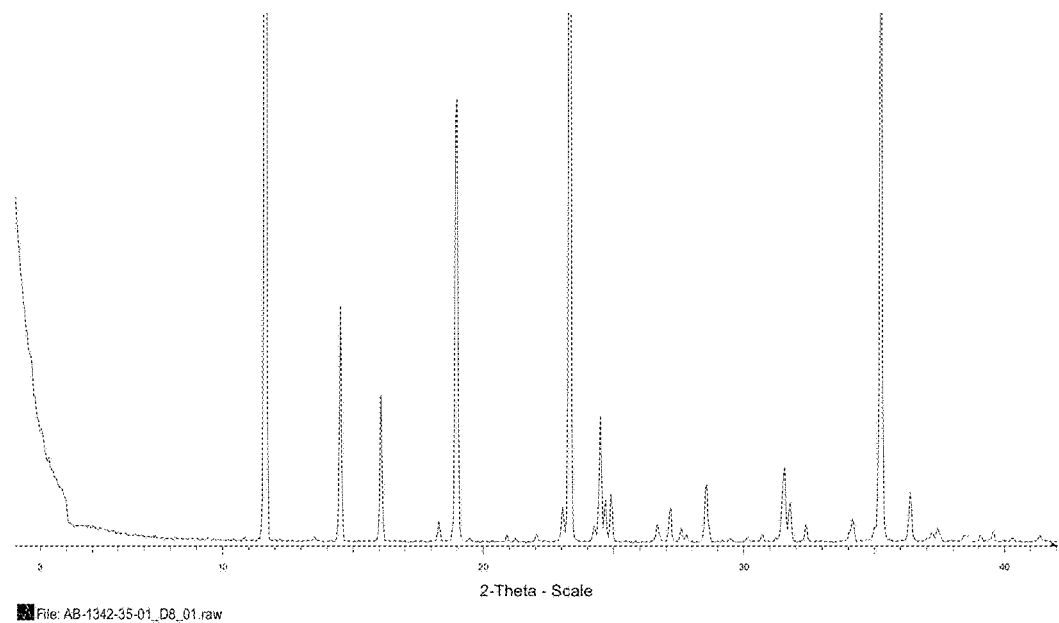
FIG. 3 depicts the XRPD pattern of Compound A, Form B.

In certain embodiments, the X-ray powder diffraction pattern is substantially similar to the XRPD provided in FIG. 3.

Methods for preparing Form B of compound A are described infra.

In some embodiments, the present invention provides compound A:

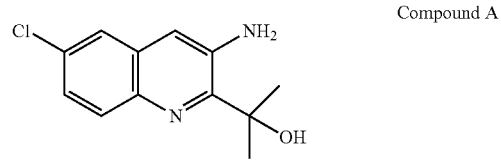 [SMILES: CC(C)(O)c1nc2ccc(Cl)cc2cc1N]

Compound A wherein said compound is crystalline.

In some embodiments, the present invention provides compound A, wherein said compound is substantially free of amorphous compound A.

In some embodiments, the present invention provides compound A, wherein said compound is substantially free of impurities.

In some embodiments, the present invention provides compound A, wherein said compound has one or more peaks in its XRPD selected from those at about 5.4, about 10.8 and about 16.6 degrees 2-theta. In some such embodiments, the present invention provides compound 1, wherein said compound has at least two peaks in its XRPD selected from those at about about 5.4, about 10.8 and about 16.6 degrees 2-theta. In some such embodiments, the present invention provides Compound A, wherein said compound is of Form A.

In some embodiments, the present invention provides compound A, wherein said compound has an XRPD substantially similar to that depicted in FIG. 1.

In some embodiments, the present invention provides compound A, wherein said compound has one or more peaks in its XRPD selected from those at about 5.4, about 10.8 and about 16.6 degrees 2-theta. In some such embodiments, the present invention provides compound A, wherein said compound has at least two peaks in its XRPD selected from those at about 5.4, about 10.8 and about 16.6 degrees 2-theta. In some such embodiments, the present invention provides compound A, wherein said compound is of Form B.

In some embodiments, the present invention provides compound A, wherein said compound has an XRPD substantially similar to that depicted in FIG. 3.

In some embodiments, the present invention provides a composition comprising compound A and a pharmaceutically acceptable carrier or excipient.

In some embodiments, the present invention provides a method of inhibiting or preventing the accumulation of A2E in a patient comprising administering to said patient compound A or composition thereof.

In some embodiments, the present invention provides a method of treating various conditions in a patient in which aldehyde toxicity is implicated in the pathogenesis, comprising administering to said patient compound A or composition thereof. In some embodiments, compound A is of Form B. In some embodiments, the present invention provides a method of treating one or more of the diseases, disorders, or conditions described herein.

Salt Forms of Compound A

In some embodiments, an acid and compound A are ionically bonded to form one of compounds 1 through 9, described below. It is contemplated that compounds 1 through 9 can exist in a variety of physical forms. For example, compounds 1 through 9 can be in solution, suspension, or in solid form. In certain embodiments, compounds 1 through 9 are in solid form. When compounds 1 through 9 are in solid form, said compounds may be amorphous, crystalline, or a mixture thereof. Exemplary such solid forms of compounds 1 through 9 are described in more detail below.

Compound 1 (Mesylate Salts of Compound A)

According to one embodiment, the present invention provides a mesylate salt of compound A, represented by compound 1:

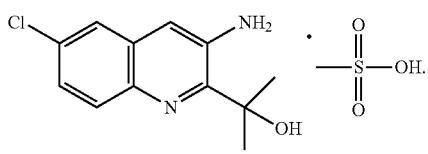

It will be appreciated by one of ordinary skill in the art that the methanesulfonic acid and compound A are ionically bonded to form compound 1. It is contemplated that compound 1 can exist in a variety of physical forms. For example, compound 1 can be in solution, suspension, or in solid form. In certain embodiments, compound 1 is in solid form. When compound 1 is in solid form, said compound may be amorphous, crystalline, or a mixture thereof. Exemplary solid forms are described in more detail below.

In some embodiments, the present invention provides compound 1 substantially free of impurities. As used herein, the term "substantially free of impurities" means that the compound contains no significant amount of extraneous matter. Such extraneous matter may include excess methanesulfonic acid, excess compound A, residual solvents, or any other impurities that may result from the preparation of, and/or isolation of, compound 1. In certain embodiments, at least about 95% by weight of compound 1 is present. In still other embodiments of the invention, at least about 99% by weight of compound 1 is present.

According to one embodiment, compound 1 is present in an amount of at least about 97, 97.5, 98.0, 98.5, 99, 99.5, 99.8 weight percent where the percentages are based on the total weight of the composition. According to another embodiment, compound 1 contains no more than about 3.0 area percent HPLC of total organic impurities and, in certain embodiments, no more than about 1.5 area percent HPLC total organic impurities relative to the total area of the HPLC chromatogram. In other embodiments, compound 1 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 1 is also meant to include all tautomeric forms of compound 1. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 1 can exist in a variety of solid forms. Exemplary such forms include polymorphs such as those described herein.

In certain embodiments, compound 1 is a crystalline solid. In other embodiments, compound 1 is a crystalline solid substantially free of amorphous compound 1. As used herein, the term "substantially free of amorphous compound 1" means that the compound contains no significant amount of amorphous compound 1. In certain embodiments, at least about 95% by weight of crystalline compound 1 is present. In still other embodiments of the invention, at least about 99% by weight of crystalline compound 1 is present.

It has been found that compound 1 can exist in at least two distinct polymorphic forms. In some embodiments, the present invention provides a polymorphic form of Compound 1 referred to herein as Form A. In certain embodiments, the present invention provides a polymorphic form of compound 1 referred to herein as Form B.

In some embodiments, compound 1 is amorphous. In some embodiments, compound 1 is amorphous, and is substantially free of crystalline compound 1.

Form A of Compound 1

In some embodiments, Form A of compound 1 has at least 1, 2, 3, 4 or 5 spectral peak(s) selected from the peaks listed in Table 3 below.

TABLE 3

| XRPD Peak Positions for Form A of Compound 1 | |
|---|---|
| Position (°2θ) | Intensity % |
| 9.3 | 100.0 |
| 10.1 | 2.7 |
| 12.9 | 4.9 |
| 14.0 | 2.6 |
| 15.6 | 6.4 |
| 16.5 | 10.1 |
| 16.9 | 10.9 |
| 17.4 | 3.2 |
| 18.5 | 2.9 |
| 18.7 | 6.2 |
| 19.1 | 6.9 |
| 20.5 | 7.9 |
| 21.0 | 6.4 |
| 21.6 | 8.2 |
| 22.4 | 2.6 |

TABLE 3-continued

XRPD Peak Positions for Form A of Compound 1

| Position (°2θ) | Intensity % |
|---|---|
| 22.7 | 1.7 |
| 23.1 | 7.4 |
| 23.4 | 2.6 |
| 24.0 | 3.9 |
| 24.9 | 6.9 |
| 25.8 | 2.3 |
| 26.4 | 14.6 |
| 26.7 | 1.8 |
| 27.2 | 4.6 |
| 27.8 | 4.1 |
| 28.4 | 2.2 |
| 29.5 | 3.8 |
| 29.8 | 6.7 |

[1] In this and all subsequent tables, the position 2θ is within ±0.2.

In some embodiments, Form A of compound 1 is characterized in that it has one or more peaks in its X-ray powder diffraction pattern selected from those at about 9.3, about 16.9 and about 26.4 degrees 2-theta. In some embodiments, Form A of compound 1 is characterized in that it has two or more peaks in its X-ray powder diffraction pattern selected from those at about 9.3, about 16.9 and about 26.4 degrees 2-theta. In some embodiments, Form A of compound 1 is characterized in that it has all three peaks in its X-ray powder diffraction pattern selected from those at about 9.3, about 16.9 and about 26.4 degrees 2-theta.

Figure 5:
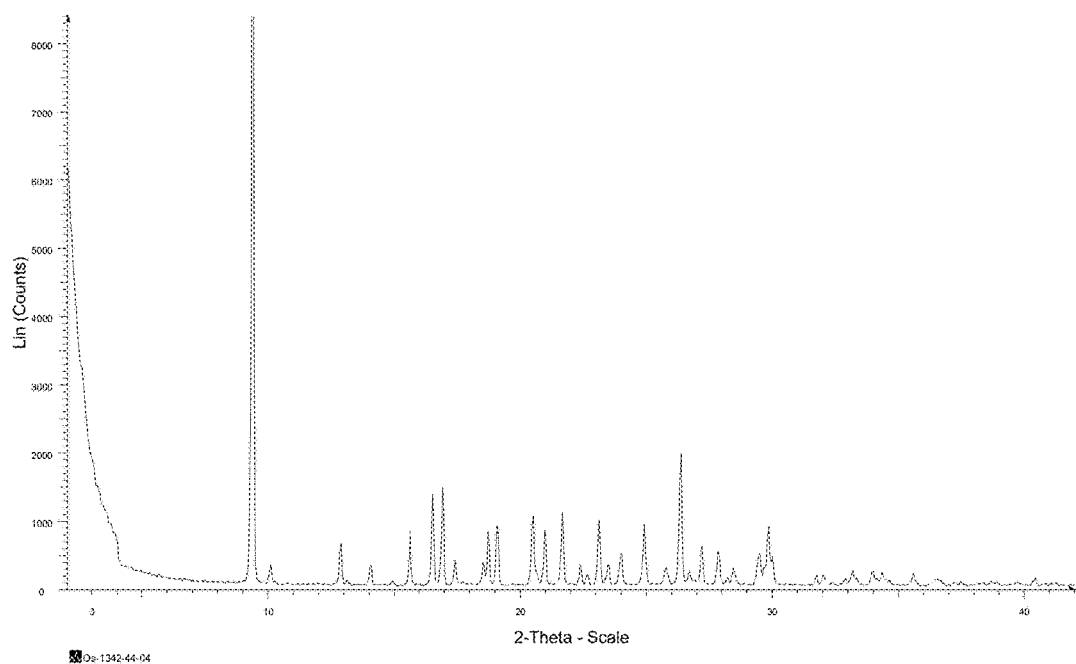
FIG. 5 depicts the XRPD pattern of Compound 1, Form A.

In certain embodiments, the X-ray powder diffraction pattern is substantially similar to the XRPD provided in FIG. 5.

Methods for preparing Form A of compound 1 are described infra.

Form B of Compound 1

In some embodiments, Form B of compound 1 has at least 1, 2, 3, 4 or 5 spectral peak(s) selected from the peaks listed in Table 4 below.

TABLE 4

XRPD Peak Positions for Form B of Compound 1

| Position (°2θ) | Intensity % |
|---|---|
| 6.9 | 1.3 |
| 9.6 | 100.0 |
| 11.8 | 9.9 |
| 13.5 | 3.5 |
| 16.4 | 3.9 |
| 16.9 | 4.3 |
| 19.1 | 18.2 |
| 19.4 | 14.8 |
| 20.3 | 6.2 |
| 20.9 | 5.1 |
| 21.8 | 3.2 |
| 23.7 | 10.3 |
| 26.2 | 11.7 |
| 28.8 | 18.2 |

[1] In this and all subsequent tables, the position 2θ is within ±0.2.

In some embodiments, Form B of compound 1 is characterized in that it has one or more peaks in its X-ray powder diffraction pattern selected from those at about 9.6, about 19.1 and about 28.8 degrees 2-theta. In some embodiments, Form B of compound 1 is characterized in that it has two or more peaks in its X-ray powder diffraction pattern selected from those at about 9.6, about 19.1 and about 28.8 degrees 2-theta. In some embodiments, Form B of compound 1 is characterized in that it has all three peaks in its X-ray powder diffraction pattern selected from those at about 9.6, about 19.1 and about 28.8 degrees 2-theta.

Figure 7:
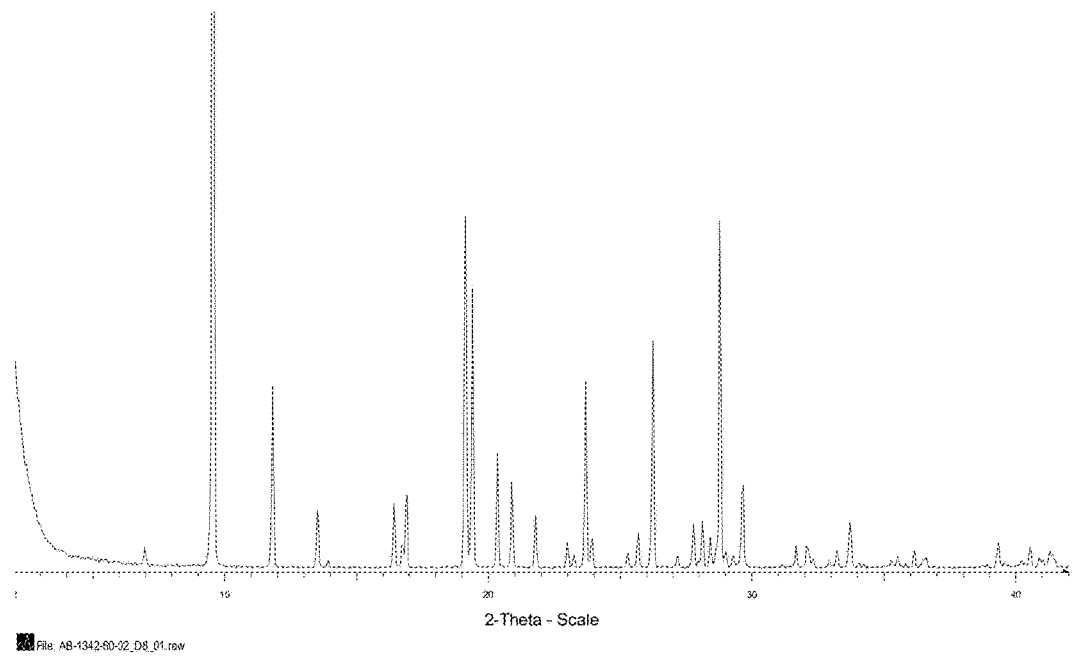
FIG. 7 depicts the XRPD pattern of Compound 1, Form B.

In certain embodiments, the X-ray powder diffraction pattern is substantially similar to the XRPD provided in FIG. 7.

Methods for preparing Form B of compound 1 are described infra.

In some embodiments, the present invention provides compound 1:

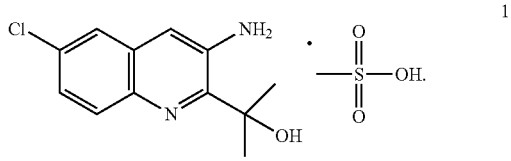

In some embodiments, the present invention provides compound 1, wherein said compound is crystalline.

In some embodiments, the present invention provides compound 1, wherein said compound is a crystalline solid substantially free of amorphous compound 1.

In some embodiments, the present invention provides compound 1, wherein said compound is substantially free of impurities.

In some embodiments, the present invention provides compound 1, wherein said compound has one or more peaks in its XRPD selected from those at about 9.3, about 16.9 and about 26.4 degrees 2-theta. In some such embodiments, the present invention provides compound 1, wherein said compound has at least two peaks in its XRPD selected from those at about 9.3, about 16.9 and about 26.4 degrees 2-theta. In some such embodiments, the present invention provides compound 1, wherein said compound is of Form A.

In some embodiments, the present invention provides compound 1, wherein said compound has an XRPD substantially similar to that depicted in FIG. 5.

In some embodiments, the present invention provides compound 1, wherein said compound has one or more peaks in its XRPD selected from those at about 9.6, about 19.1 and about 28.8 degrees 2-theta. In some such embodiments, the present invention provides compound 1, wherein said compound has at least two peaks in its XRPD selected from those at about 9.6, about 19.1 and about 28.8 degrees 2-theta. In some such embodiments, the present invention provides compound 1, wherein said compound is of Form B.

In some embodiments, the present invention provides compound 1, wherein said compound has an XRPD substantially similar to that depicted in FIG. 7.

In some embodiments, the present invention provides a composition comprising compound 1 and a pharmaceutically acceptable carrier or excipient.

In some embodiments, the present invention provides a method of inhibiting or preventing the accumulation of A2E in a patient comprising administering to said patient compound 1 or composition thereof.

In some embodiments, the present invention provides a method of treating various conditions in a patient in which aldehyde toxicity is implicated in the pathogenesis, comprising administering to said patient compound 1 or composition thereof wherein compound 1 is a crystal form as described herein. In some embodiments, the present invention provides a method of treating one or more of the diseases, disorders, or conditions described herein.

Compound 2 (Besylate Salts of Compound A)

According to one embodiment, the present invention provides a besylate salt of compound A, represented by compound 2:

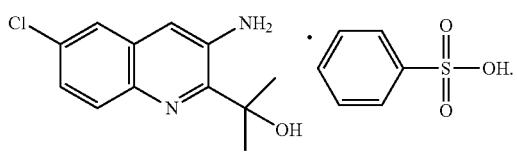

2

It will be appreciated by one of ordinary skill in the art that the benzenesulfonic acid and compound A are ionically bonded to form compound 2. It is contemplated that compound 2 can exist in a variety of physical forms. For example, compound 2 can be in solution, suspension, or in solid form. In certain embodiments, compound 2 is in solid form. When compound 2 is in solid form, said compound may be amorphous, crystalline, or a mixture thereof. Exemplary solid forms are described in more detail below.

In some embodiments, the present invention provides compound 2 substantially free of impurities. As used herein, the term "substantially free of impurities" means that the compound contains no significant amount of extraneous matter. Such extraneous matter may include excess benzenesulfonic acid, excess compound A, residual solvents, or any other impurities that may result from the preparation of, and/or isolation of, compound 2. In certain embodiments, at least about 95% by weight of compound 2 is present. In still other embodiments of the invention, at least about 99% by weight of compound 2 is present.

According to one embodiment, compound 2 is present in an amount of at least about 97, 97.5, 98.0, 98.5, 99, 99.5, 99.8 weight percent where the percentages are based on the total weight of the composition. According to another embodiment, compound 2 contains no more than about 3.0 area percent HPLC of total organic impurities and, in certain embodiments, no more than about 1.5 area percent HPLC total organic impurities relative to the total area of the HPLC chromatogram. In other embodiments, compound 2 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 2 is also meant to include all tautomeric forms of compound 2. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 2 can exist in a variety of solid forms. Exemplary such forms include polymorphs such as those described herein.

In certain embodiments, compound 2 is a crystalline solid. In other embodiments, compound 2 is a crystalline solid substantially free of amorphous compound 2. As used herein, the term "substantially free of amorphous compound 2" means that the compound contains no significant amount of amorphous compound 2. In certain embodiments, at least about 95% by weight of crystalline compound 2 is present. In still other embodiments of the invention, at least about 99% by weight of crystalline compound 2 is present.

It has been found that compound 2 can exist in at least two distinct polymorphic forms. In some embodiments, the present invention provides a polymorphic form of Compound 2 referred to herein as Form A. In certain embodiments, the present invention provides a polymorphic form of compound 2 referred to herein as Form B.

In some embodiments, compound 2 is amorphous. In some embodiments, compound 2 is amorphous, and is substantially free of crystalline compound 2.

Form A of Compound 2

In some embodiments, Form A of compound 2 has at least 1, 2, 3, 4 or 5 spectral peak(s) selected from the peaks listed in Table 5 below.

TABLE 5

XRPD Peak Positions for Form A of Compound 2

| Position (°2θ) | Intensity % |
|---|---|
| 6.3 | 4.4 |
| 6.8 | 7.4 |
| 8.4 | 100.0 |
| 10.1 | 5.0 |
| 11.0 | 3.3 |
| 13.3 | 13.5 |
| 14.0 | 14.3 |
| 16.3 | 7.4 |
| 16.9 | 8.6 |
| 17.5 | 4.1 |
| 18.7 | 7.4 |
| 20.1 | 10.2 |
| 20.5 | 5.2 |
| 21.1 | 5.2 |
| 21.3 | 8.0 |
| 24.8 | 6.9 |
| 25.4 | 18.6 |
| 26.0 | 11.9 |

[1] In this and all subsequent tables, the position 2θ is within ±0.2.

In some embodiments, Form A of compound 2 is characterized in that it has one or more peaks in its X-ray powder diffraction pattern selected from those at about 8.4, about 14.0 and about 25.4 degrees 2-theta. In some embodiments, Form A of compound 2 is characterized in that it has two or more peaks in its X-ray powder diffraction pattern selected from those at about 8.4, about 14.0 and about 25.4 degrees 2-theta. In some embodiments, Form A of compound 2 is characterized in that it has all three peaks in its X-ray powder diffraction pattern selected from those at about 8.4, about 14.0 and about 25.4 degrees 2-theta.

Figure 9:
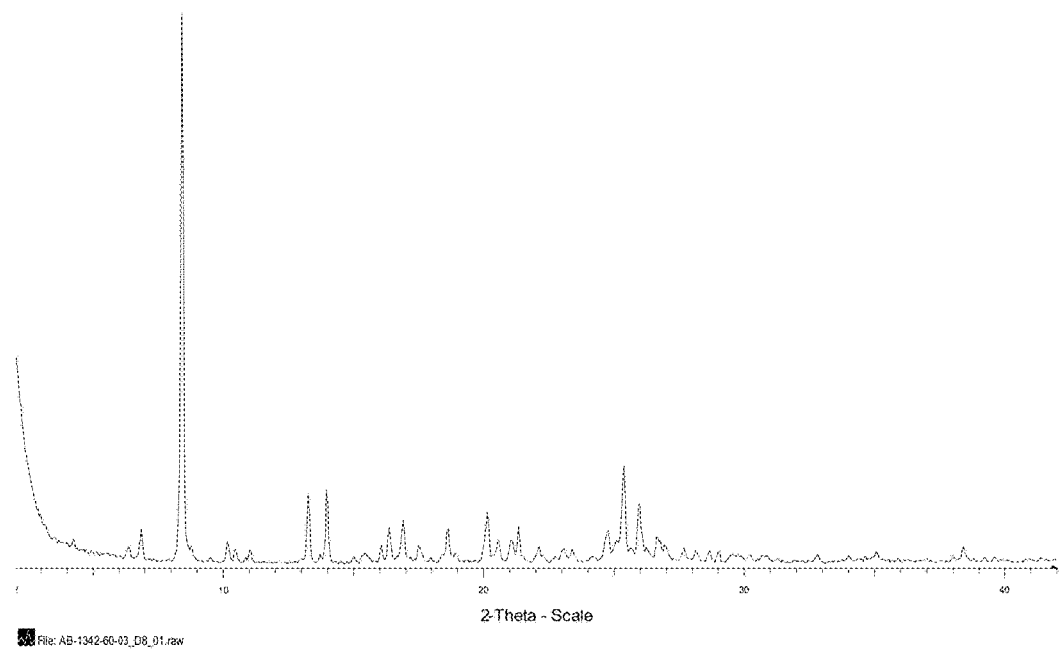
FIG. 9 depicts the XRPD pattern of Compound 2, Form A.

In certain embodiments, the X-ray powder diffraction pattern is substantially similar to the XRPD provided in FIG. 9.

Methods for preparing Form A of compound 2 are described infra.

Form B of Compound 2

In some embodiments, Form B of compound 2 has at least 1, 2, 3, 4 or 5 spectral peak(s) selected from the peaks listed in Table 6 below.

TABLE 6

XRPD Peak Positions for Form B of Compound 2

| Position (°2θ) | Intensity % |
|---|---|
| 5.8 | 19.3 |
| 6.0 | 12.3 |

TABLE 6-continued

XRPD Peak Positions for Form B of Compound 2

| Position (°2θ) | Intensity % |
|---|---|
| 7.1 | 17.3 |
| 8.4 | 51.2 |
| 13.1 | 16.3 |
| 13.9 | 20.6 |
| 14.5 | 46.8 |
| 16.9 | 21.9 |
| 18.2 | 29.0 |
| 20.1 | 46.2 |
| 24.1 | 42.2 |
| 24.9 | 49.0 |
| 25.8 | 34.7 |
| 26.8 | 100.0 |
| 29.3 | 54.7 |

[1] In this and all subsequent tables, the position 2θ is within ±0.2.

In some embodiments, Form B of compound 2 is characterized in that it has one or more peaks in its X-ray powder diffraction pattern selected from those at about 8.4, about 26.8 and about 29.3 degrees 2-theta. In some embodiments, Form B of compound 2 is characterized in that it has two or more peaks in its X-ray powder diffraction pattern selected from those at about 8.4, about 26.8 and about 29.3 degrees 2-theta. In some embodiments, Form B of compound 2 is characterized in that it has all three peaks in its X-ray powder diffraction pattern selected from those at about 8.4, about 26.8 and about 29.3 degrees 2-theta.

Figure 11:
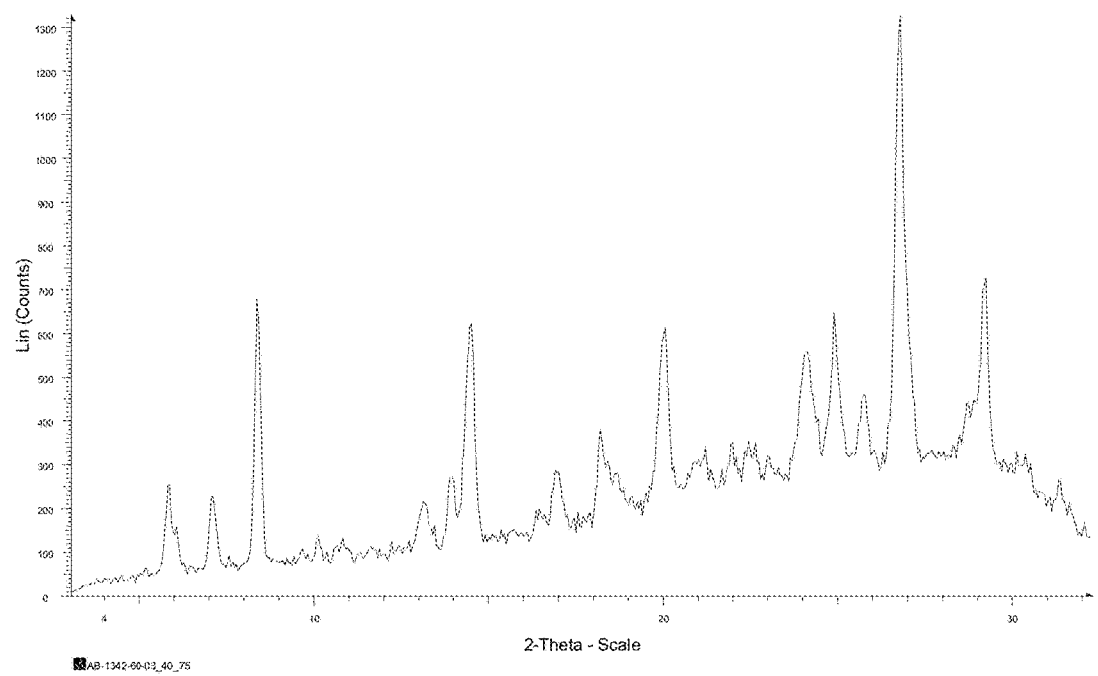
FIG. 11 depicts the XRPD pattern of Compound 2, Form B.

In certain embodiments, the X-ray powder diffraction pattern is substantially similar to the XRPD provided in FIG. 11.

Methods for preparing Form B of compound 2 are described infra.

In some embodiments, the present invention provides compound 2:

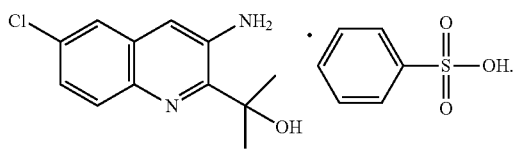

In some embodiments, the present invention provides compound 2, wherein said compound is crystalline.

In some embodiments, the present invention provides compound 2, wherein said compound is a crystalline solid substantially free of amorphous compound 2.

In some embodiments, the present invention provides compound 2, wherein said compound is substantially free of impurities.

In some embodiments, the present invention provides compound 2, wherein said compound has one or more peaks in its XRPD selected from those at about 8.4, about 14.0 and about 25.4 degrees 2-theta. In some such embodiments, the present invention provides compound 2, wherein said compound has at least two peaks in its XRPD selected from those at about 8.4, about 14.0 and about 25.4 degrees 2-theta. In some such embodiments, the present invention provides compound 2, wherein said compound is of Form A.

In some embodiments, the present invention provides compound 2, wherein said compound has an XRPD substantially similar to that depicted in FIG. 9.

In some embodiments, the present invention provides compound 2, wherein said compound has one or more peaks in its XRPD selected from those at about 8.4, about 26.8 and about 29.3 degrees 2-theta. In some such embodiments, the present invention provides compound 2, wherein said compound has at least two peaks in its XRPD selected from those at about 8.4, about 26.8 and about 29.3 degrees 2-theta. In some such embodiments, the present invention provides compound 2, wherein said compound is of Form B.

In some embodiments, the present invention provides compound 2, wherein said compound has an XRPD substantially similar to that depicted in FIG. 11.

In some embodiments, the present invention provides a composition comprising compound 2 and a pharmaceutically acceptable carrier or excipient.

In some embodiments, the present invention provides a method of inhibiting or preventing the accumulation of A2E in a patient comprising administering to said patient compound 2 or composition thereof.

In some embodiments, the present invention provides a method of treating various conditions in a patient in which aldehyde toxicity is implicated in the pathogenesis, comprising administering to said patient compound 2 or a crystal form as described herein. In some embodiments, the present invention provides a method of treating one or more of the diseases, disorders, or conditions described herein.

Compound 3 (Sulfate Salts of Compound A)

According to one embodiment, the present invention provides a sulfate salt of compound A, represented by compound 3:

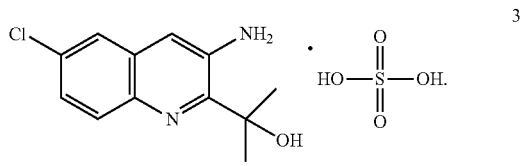 [SMILES: CC(C)(O)c1nc2ccc(Cl)cc2cc1N ; O=S(=O)(O)O]

It will be appreciated by one of ordinary skill in the art that the sulfuric acid and compound A are ionically bonded to form compound 3. It is contemplated that compound 3 can exist in a variety of physical forms. For example, compound 3 can be in solution, suspension, or in solid form. In certain embodiments, compound 3 is in solid form. When compound 3 is in solid form, said compound may be amorphous, crystalline, or a mixture thereof. Exemplary solid forms are described in more detail below.

In some embodiments, the present invention provides compound 3 substantially free of impurities. As used herein, the term "substantially free of impurities" means that the compound contains no significant amount of extraneous matter. Such extraneous matter may include excess sulfuric acid, excess compound A, residual solvents, or any other impurities that may result from the preparation of, and/or isolation of, compound 3. In certain embodiments, at least about 95% by weight of compound 3 is present. In still other embodiments of the invention, at least about 99% by weight of compound 3 is present.

According to one embodiment, compound 3 is present in an amount of at least about 97, 97.5, 98.0, 98.5, 99, 99.5, 99.8 weight percent where the percentages are based on the total weight of the composition. According to another embodiment, compound 3 contains no more than about 3.0 area percent HPLC of total organic impurities and, in certain embodiments, no more than about 1.5 area percent HPLC total organic impurities relative to the total area of the HPLC chromatogram. In other embodiments, compound 3 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 3 is also meant to include all tautomeric forms of compound 3. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 3 can exist in a variety of solid forms. Exemplary such forms include polymorphs such as those described herein.

In certain embodiments, compound 3 is a crystalline solid. In other embodiments, compound 3 is a crystalline solid substantially free of amorphous compound 3. As used herein, the term "substantially free of amorphous compound 3" means that the compound contains no significant amount of amorphous compound 3. In certain embodiments, at least about 95% by weight of crystalline compound 3 is present. In still other embodiments of the invention, at least about 99% by weight of crystalline compound 3 is present.

In some embodiments, compound 3 is amorphous. In some embodiments, compound 3 is amorphous, and is substantially free of crystalline compound 3.

Form A of Compound 3

In some embodiments, Form A of compound 3 has at least 1, 2, 3, 4 or 5 spectral peak(s) selected from the peaks listed in Table 7 below.

TABLE 7

XRPD Peak Positions for Form A of Compound 3

| Position (°2θ) | Intensity % |
|---|---|
| 10.0 | 23.9 |
| 12.5 | 7.6 |
| 12.7 | 17.9 |
| 14.8 | 5.2 |
| 17.2 | 46.5 |
| 18.5 | 9.3 |
| 19.1 | 23.5 |
| 20.0 | 5.8 |
| 20.4 | 4.2 |
| 20.8 | 9.0 |
| 22.0 | 11.5 |
| 22.8 | 25.8 |
| 23.4 | 7.0 |
| 23.8 | 37.9 |
| 24.9 | 9.0 |
| 25.5 | 100.0 |
| 25.7 | 14.9 |
| 27.3 | 10.4 |
| 27.7 | 12.2 |

[1] In this and all subsequent tables, the position 2θ is within ±0.2.

In some embodiments, Form A of compound 3 is characterized in that it has one or more peaks in its X-ray powder diffraction pattern selected from those at about 17.2, about 23.8 and about 25.5 degrees 2-theta. In some embodiments, Form A of compound 3 is characterized in that it has two or more peaks in its X-ray powder diffraction pattern selected from those at about 17.2, about 23.8 and about 25.5 degrees 2-theta. In some embodiments, Form A of compound 3 is characterized in that it has all three peaks in its X-ray powder diffraction pattern selected from those at about 17.2, about 23.8 and about 25.5 degrees 2-theta.

Figure 12:
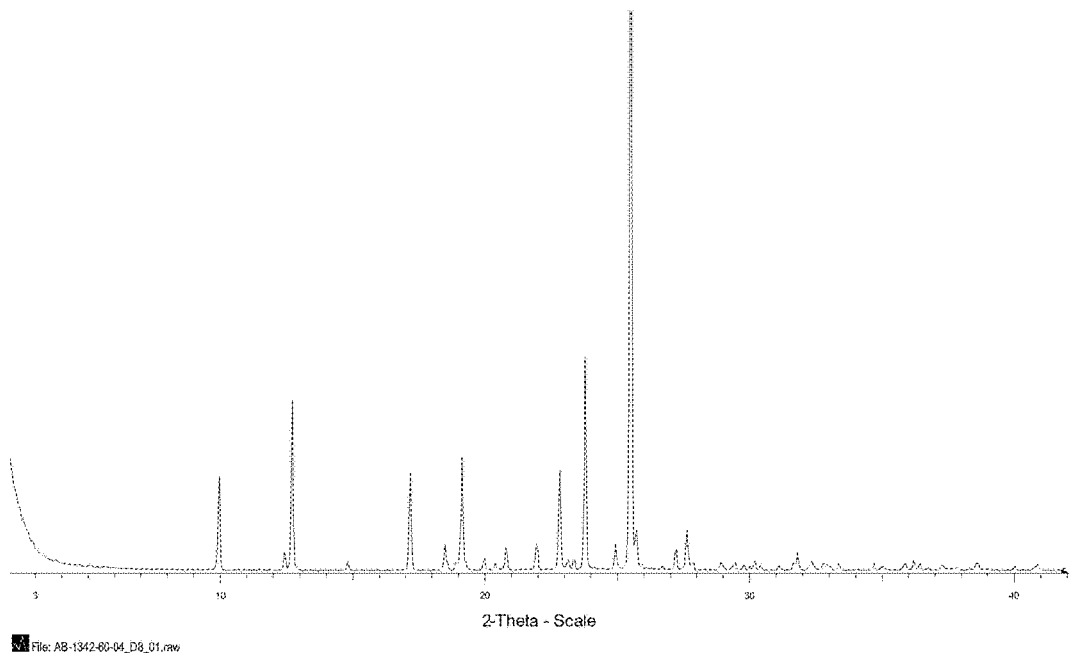
FIG. 12 depicts the XRPD pattern of Compound 3, Form A.

In certain embodiments, the X-ray powder diffraction pattern is substantially similar to the XRPD provided in FIG. 12.

Methods for preparing Form A of compound 3 are described infra.

In some embodiments, the present invention provides compound 3:

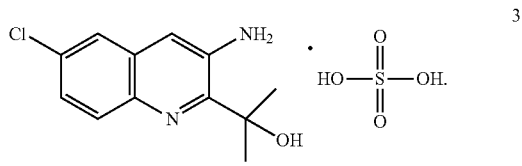 [SMILES: CC(C)(O)c1nc2ccc(Cl)cc2cc1N ; O=S(=O)(O)O]

In some embodiments, the present invention provides compound 3, wherein said compound is crystalline.

In some embodiments, the present invention provides compound 3, wherein said compound is a crystalline solid substantially free of amorphous compound 3.

In some embodiments, the present invention provides compound 3, wherein said compound is substantially free of impurities.

In some embodiments, the present invention provides compound 3, wherein said compound has one or more peaks in its XRPD selected from those at about 17.2, about 23.8 and about 25.5 degrees 2-theta. In some such embodiments, the present invention provides compound 3, wherein said compound has at least two peaks in its XRPD selected from those at about 17.2, about 23.8 and about 25.5 degrees 2-theta. In some such embodiments, the present invention provides compound 3, wherein said compound is of Form A.

In some embodiments, the present invention provides compound 3, wherein said compound has an XRPD substantially similar to that depicted in FIG. 12.

In some embodiments, the present invention provides a composition comprising compound 3 and a pharmaceutically acceptable carrier or excipient.

In some embodiments, the present invention provides a method of inhibiting or preventing the accumulation of A2E in a patient comprising administering to said patient compound 3 or composition thereof.

In some embodiments, the present invention provides a method of treating various conditions in a patient in which aldehyde toxicity is implicated in the pathogenesis, comprising administering to said patient compound 3 or a crystal form as described herein. In some embodiments, the present invention provides a method of treating one or more of the diseases, disorders, or conditions described herein.

Compound 4 (Tosylate Salts of Compound A)

According to one embodiment, the present invention provides a tosylate salt of compound A, represented by compound 4:

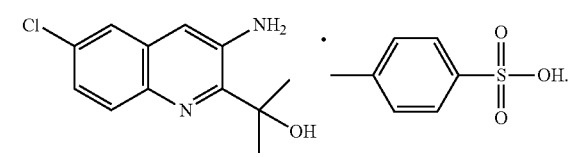

By "tosylate" is meant p-toluene sulfonate, i.e., the ionic form of p-toluenesulfonic acid. It will be appreciated by one of ordinary skill in the art that the p-toluenesulfonic acid and compound A are ionically bonded to form compound 4. It is contemplated that compound 4 can exist in a variety of physical forms. For example, compound 4 can be in solution, suspension, or in solid form. In certain embodiments, compound 4 is in solid form. When compound 4 is in solid form, said compound may be amorphous, crystalline, or a mixture thereof. Exemplary solid forms are described in more detail below.

In some embodiments, the present invention provides compound 4 substantially free of impurities. As used herein, the term "substantially free of impurities" means that the compound contains no significant amount of extraneous matter. Such extraneous matter may include excess p-toluenesulfonic acid, excess compound A, residual solvents, or any other impurities that may result from the preparation of, and/or isolation of, compound 4. In certain embodiments, at least about 95% by weight of compound 4 is present. In still other embodiments of the invention, at least about 99% by weight of compound 4 is present.

According to one embodiment, compound 4 is present in an amount of at least about 97, 97.5, 98.0, 98.5, 99, 99.5, 99.8 weight percent where the percentages are based on the total weight of the composition. According to another embodiment, compound 4 contains no more than about 3.0 area percent HPLC of total organic impurities and, in certain embodiments, no more than about 1.5 area percent HPLC total organic impurities relative to the total area of the HPLC chromatogram. In other embodiments, compound 4 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 4 is also meant to include all tautomeric forms of compound 4. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 4 can exist in a variety of solid forms. Exemplary such forms include polymorphs such as those described herein.

In certain embodiments, compound 4 is a crystalline solid. In other embodiments, compound 4 is a crystalline solid substantially free of amorphous compound 4. As used herein, the term "substantially free of amorphous compound 4" means that the compound contains no significant amount of amorphous compound 4. In certain embodiments, at least about 95% by weight of crystalline compound 4 is present. In still other embodiments of the invention, at least about 99% by weight of crystalline compound 4 is present.

In some embodiments, compound 4 is amorphous. In some embodiments, compound 4 is amorphous, and is substantially free of crystalline compound 4.

Form A of Compound 4

In some embodiments, Form A of compound 4 has at least 1, 2, 3, 4 or 5 spectral peak(s) selected from the peaks listed in Table 8 below.

TABLE 8

XRPD Peak Positions for Form A of Compound 4

| Position (°2θ) | Intensity % |
|---|---|
| 8.2 | 8.3 |
| 11.1 | 6.0 |
| 13.4 | 60.5 |
| 14.2 | 9.9 |
| 15.3 | 16.1 |
| 16.5 | 18.2 |
| 17.0 | 73.8 |
| 17.7 | 18.6 |
| 18.0 | 20.7 |
| 18.6 | 6.7 |
| 20.7 | 51.7 |
| 21.5 | 9.9 |
| 22.0 | 29.9 |
| 22.1 | 6.9 |
| 22.4 | 42.5 |
| 23.2 | 22.1 |
| 24.5 | 6.7 |
| 25.3 | 12.6 |
| 25.9 | 100.0 |
| 26.5 | 33.3 |
| 27.0 | 9.9 |
| 27.3 | 29.0 |
| 29.3 | 32.4 |

[1] In this and all subsequent tables, the position 2θ is within ±0.2.

In some embodiments, Form A of compound 4 is characterized in that it has one or more peaks in its X-ray powder diffraction pattern selected from those at about 13.4, about 17.0 and about 25.9 degrees 2-theta. In some embodiments, Form A of compound 4 is characterized in that it has two or more peaks in its X-ray powder diffraction pattern selected from those at about 13.4, about 17.0 and about 25.9 degrees 2-theta. In some embodiments, Form A of compound 4 is characterized in that it has all three peaks in its X-ray powder diffraction pattern selected from those at about 13.4, about 17.0 and about 25.9 degrees 2-theta.

Figure 14:
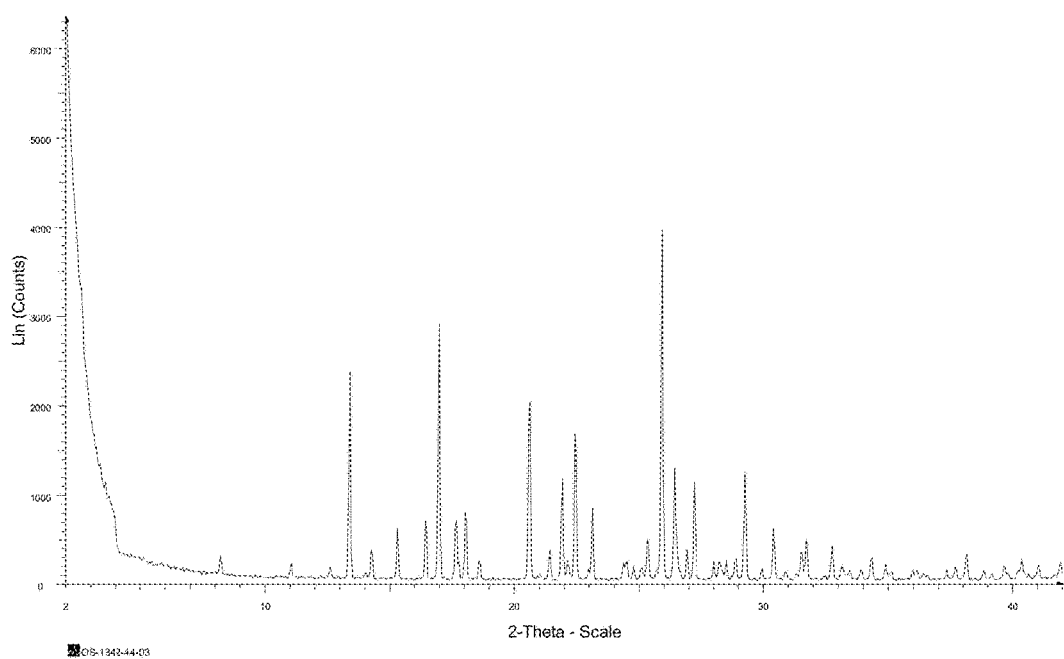
FIG. 14 depicts the XRPD pattern of Compound 4, Form A.

In certain embodiments, the X-ray powder diffraction pattern is substantially similar to the XRPD provided in FIG. 14.

Methods for preparing Form A of compound 4 are described infra.

In some embodiments, the present invention provides compound 4:

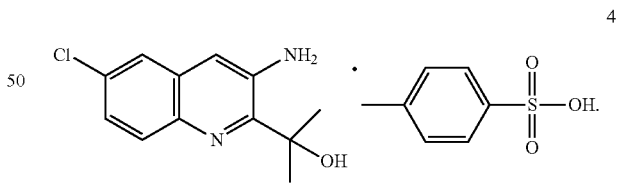

In some embodiments, the present invention provides compound 4, wherein said compound is crystalline.

In some embodiments, the present invention provides compound 4, wherein said compound is a crystalline solid substantially free of amorphous compound 4.

In some embodiments, the present invention provides compound 4, wherein said compound is substantially free of impurities.

In some embodiments, the present invention provides compound 4, wherein said compound has one or more peaks in its XRPD selected from those at about 13.4, about 17.0 and about 25.9 degrees 2-theta. In some such embodiments, the present invention provides compound 4, wherein said compound has at least two peaks in its XRPD selected from those at about 13.4, about 17.0 and about 25.9 degrees 2-theta. In some such embodiments, the present invention provides compound 4, wherein said compound is of Form A.

In some embodiments, the present invention provides compound 4, wherein said compound has an XRPD substantially similar to that depicted in FIG. 14.

In some embodiments, the present invention provides a composition comprising compound 4 and a pharmaceutically acceptable carrier or excipient.

In some embodiments, the present invention provides a method of inhibiting or preventing the accumulation of A2E in a patient comprising administering to said patient compound 4 or composition thereof.

In some embodiments, the present invention provides a method of treating various conditions in a patient in which aldehyde toxicity is implicated in the pathogenesis, comprising administering to said patient compound 4 or a crystal form as described herein. In some embodiments, the present invention provides a method of treating one or more of the diseases, disorders, or conditions described herein.

Compound 5 (Hydrochloride Salts of Compound A)

According to one embodiment, the present invention provides a hydrochloride salt of compound A, represented by compound 5:

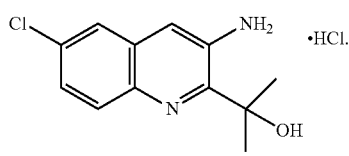

It will be appreciated by one of ordinary skill in the art that the hydrochloric acid and compound A are ionically bonded to form compound 5. It is contemplated that compound 5 can exist in a variety of physical forms. For example, compound 5 can be in solution, suspension, or in solid form. In certain embodiments, compound 5 is in solid form. When compound 5 is in solid form, said compound may be amorphous, crystalline, or a mixture thereof. Exemplary solid forms are described in more detail below.

In some embodiments, the present invention provides compound 5 substantially free of impurities. As used herein, the term "substantially free of impurities" means that the compound contains no significant amount of extraneous matter. Such extraneous matter may include excess hydrochloric acid, excess compound A, residual solvents, or any other impurities that may result from the preparation of, and/or isolation of, compound 5. In certain embodiments, at least about 95% by weight of compound 5 is present. In still other embodiments of the invention, at least about 99% by weight of compound 5 is present.

According to one embodiment, compound 5 is present in an amount of at least about 97, 97.5, 98.0, 98.5, 99, 99.5, 99.8 weight percent where the percentages are based on the total weight of the composition. According to another embodiment, compound 5 contains no more than about 3.0 area percent HPLC of total organic impurities and, in certain embodiments, no more than about 1.5 area percent HPLC total organic impurities relative to the total area of the HPLC chromatogram. In other embodiments, compound 5 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 5 is also meant to include all tautomeric forms of compound 5. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that compound 5 can exist in a variety of solid forms. Exemplary such forms include polymorphs such as those described herein.

In certain embodiments, compound 5 is a crystalline solid. In other embodiments, compound 5 is a crystalline solid substantially free of amorphous compound 5. As used herein, the term "substantially free of amorphous compound 5" means that the compound contains no significant amount of amorphous compound 5. In certain embodiments, at least about 95% by weight of crystalline compound 5 is present. In still other embodiments of the invention, at least about 99% by weight of crystalline compound 5 is present.

In some embodiments, compound 5 is amorphous. In some embodiments, compound 5 is amorphous, and is substantially free of crystalline compound 5.

Form A of Compound 5

In some embodiments, Form A of compound 5 has at least 1, 2, 3, 4 or 5 spectral peak(s) selected from the peaks listed in Table 9 below.

TABLE 9

XRPD Peak Positions for Form A of Compound 5

| Position (°2θ) | Intensity % |
|---|---|
| 8.7 | 17.6 |
| 9.7 | 11.3 |
| 10.7 | 21.6 |
| 16.2 | 9.9 |
| 17.0 | 100.0 |
| 17.3 | 9.6 |
| 19.9 | 5.6 |
| 22.6 | 25.7 |
| 24.7 | 8.2 |
| 25.2 | 11.9 |
| 26.1 | 25.7 |
| 29.3 | 17.6 |
| 29.9 | 10.5 |
| 32.0 | 10.6 |

[1] In this and all subsequent tables, the position 2θ is within ±0.2.

In some embodiments, Form A of compound 5 is characterized in that it has one or more peaks in its X-ray powder diffraction pattern selected from those at about 17.0, about 22.6 and about 26.1 degrees 2-theta. In some embodiments, Form A of compound 5 is characterized in that it has two or more peaks in its X-ray powder diffraction pattern selected from those at about 17.0, about 22.6 and about 26.1 degrees 2-theta. In some embodiments, Form A of compound 5 is characterized in that it has all three peaks in its X-ray powder diffraction pattern selected from those at about 17.0, about 22.6 and about 26.1 degrees 2-theta.

Figure 16:
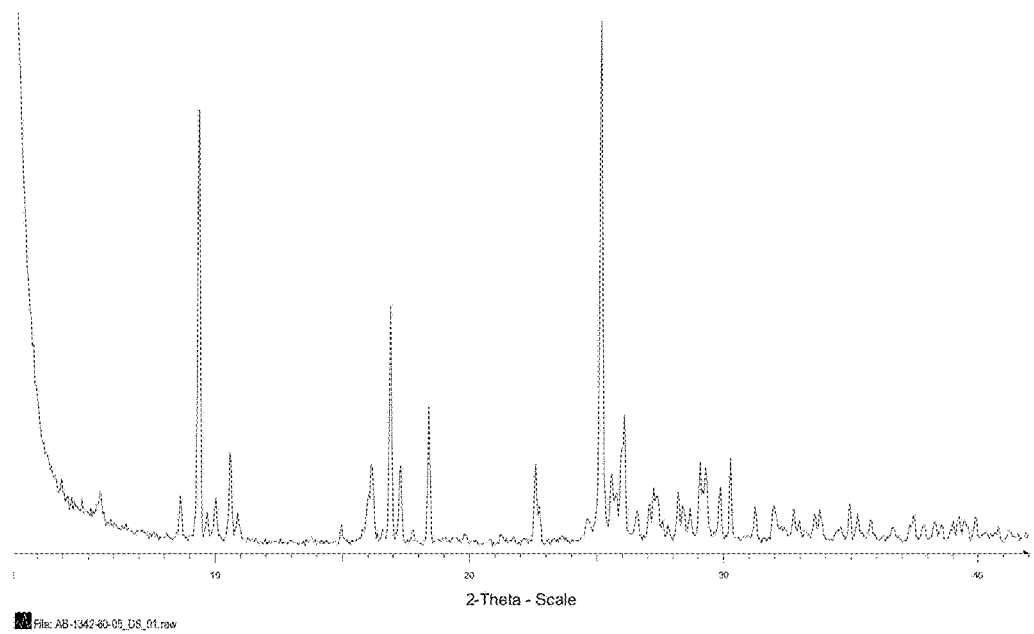
FIG. 16 depicts the XRPD pattern of Compound 5, Form A.

In certain embodiments, the X-ray powder diffraction pattern is substantially similar to the XRPD provided in FIG. 16.

Methods for preparing Form A of compound 5 are described infra.

In some embodiments, the present invention provides compound 5:

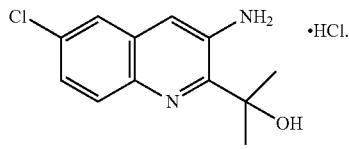

In some embodiments, the present invention provides compound 5, wherein said compound is crystalline.

In some embodiments, the present invention provides compound 5, wherein said compound is a crystalline solid substantially free of amorphous compound 5.

In some embodiments, the present invention provides compound 5, wherein said compound is substantially free of impurities.

In some embodiments, the present invention provides compound 5, wherein said compound has one or more peaks in its XRPD selected from those at about 17.0, about 22.6 and about 26.1 degrees 2-theta. In some such embodiments, the present invention provides compound 5, wherein said compound has at least two peaks in its XRPD selected from those at about 17.0, about 22.6 and about 26.1 degrees 2-theta. In some such embodiments, the present invention provides compound 5, wherein said compound is of Form A.

In some embodiments, the present invention provides compound 5, wherein said compound has an XRPD substantially similar to that depicted in FIG. 16.

In some embodiments, the present invention provides a composition comprising compound 5 and a pharmaceutically acceptable carrier or excipient.

In some embodiments, the present invention provides a method of inhibiting or preventing the accumulation of A2E in a patient comprising administering to said patient compound 5 or composition thereof.

In some embodiments, the present invention provides a method of treating various conditions in a patient in which aldehyde toxicity is implicated in the pathogenesis, comprising administering to said patient compound 5 or a crystal form as described herein. In some embodiments, the present invention provides a method of treating one or more of the diseases, disorders, or conditions described herein.

Compound 6 (Oxalate Salts of Compound A)

According to one embodiment, the present invention provides an oxalate salt of compound A, represented by compound 6:

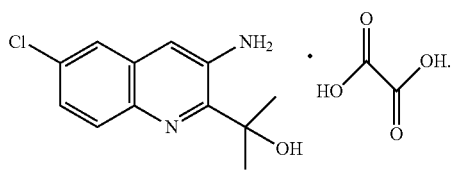

It will be appreciated by one of ordinary skill in the art that the oxalic acid and compound A are ionically bonded to form compound 6. It is contemplated that compound 6 can exist in a variety of physical forms. For example, compound 6 can be in solution, suspension, or in solid form. In certain embodiments, compound 6 is in solid form. When compound 6 is in solid form, said compound may be amorphous, crystalline, or a mixture thereof. Exemplary solid forms are described in more detail below.

In some embodiments, the present invention provides compound 6 substantially free of impurities. As used herein, the term "substantially free of impurities" means that the compound contains no significant amount of extraneous matter. Such extraneous matter may include excess oxalic acid, excess compound A, residual solvents, or any other impurities that may result from the preparation of, and/or isolation of, compound 6. In certain embodiments, at least about 95% by weight of compound 6 is present. In still other embodiments of the invention, at least about 99% by weight of compound 6 is present.

According to one embodiment, compound 6 is present in an amount of at least about 97, 97.5, 98.0, 98.5, 99, 99.5, 99.8 weight percent where the percentages are based on the total weight of the composition. According to another embodiment, compound 6 contains no more than about 3.0 area percent HPLC of total organic impurities and, in certain embodiments, no more than about 1.5 area percent HPLC total organic impurities relative to the total area of the HPLC chromatogram. In other embodiments, compound 6 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 6 is also meant to include all tautomeric forms of compound 6. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 6 can exist in a variety of solid forms. Exemplary such forms include polymorphs such as those described herein.

In certain embodiments, compound 6 is a crystalline solid. In other embodiments, compound 6 is a crystalline solid substantially free of amorphous compound 6. As used herein, the term "substantially free of amorphous compound 6" means that the compound contains no significant amount of amorphous compound 6. In certain embodiments, at least about 95% by weight of crystalline compound 6 is present. In still other embodiments of the invention, at least about 99% by weight of crystalline compound 6 is present.

In some embodiments, compound 6 is amorphous. In some embodiments, compound 6 is amorphous, and is substantially free of crystalline compound 6.

Form A of Compound 6

In some embodiments, Form A of compound 6 has at least 1, 2, 3, 4 or 5 spectral peak(s) selected from the peaks listed in Table 10 below.

TABLE 10

XRPD Peak Positions for Form A of Compound 6

| Position (°2θ) | Intensity % |
|---|---|
| 8.4 | 16.1 |
| 11.1 | 48.0 |
| 12.5 | 50.0 |
| 13.3 | 13.9 |
| 13.9 | 11.8 |

TABLE 10-continued

XRPD Peak Positions for Form A of Compound 6

| Position (°2θ) | Intensity % |
|---|---|
| 14.6 | 10.2 |
| 15.5 | 11.0 |
| 16.0 | 10.8 |
| 16.9 | 100.0 |
| 17.3 | 23.3 |
| 19.1 | 22.3 |
| 19.8 | 60.4 |
| 22.4 | 28.5 |
| 23.6 | 27.7 |
| 24.0 | 28.7 |
| 24.3 | 25.3 |
| 24.4 | 23.3 |
| 25.3 | 64.9 |
| 25.6 | 27.5 |
| 26.1 | 14.9 |
| 26.3 | 15.7 |
| 27.3 | 16.5 |
| 27.8 | 23.7 |

1 In this and all subsequent tables, the position 2θ is within ±0.2.

In some embodiments, Form A of compound 6 is characterized in that it has one or more peaks in its X-ray powder diffraction pattern selected from those at about 16.9, about 19.8 and about 25.3 degrees 2-theta. In some embodiments, Form A of compound 6 is characterized in that it has two or more peaks in its X-ray powder diffraction pattern selected from those at about 16.9, about 19.8 and about 25.3 degrees 2-theta. In some embodiments, Form A of compound 6 is characterized in that it has all three peaks in its X-ray powder diffraction pattern selected from those at about 16.9, about 19.8 and about 25.3 degrees 2-theta.

Figure 18:
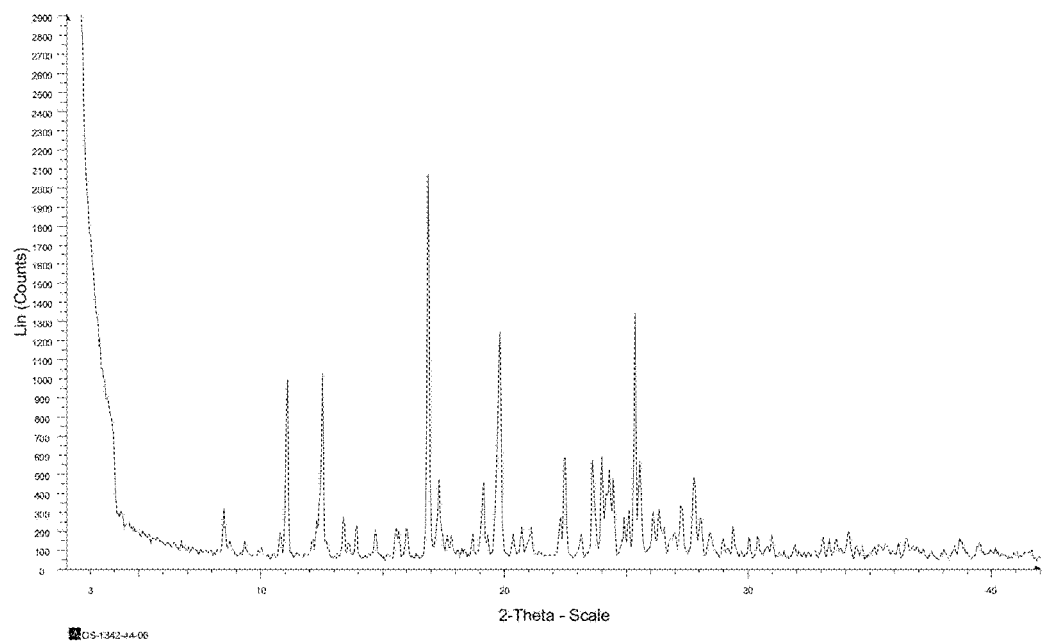
FIG. 18 depicts the XRPD pattern of Compound 6, Form A.

In certain embodiments, the X-ray powder diffraction pattern is substantially similar to the XRPD provided in FIG. 18.

Methods for preparing Form A of compound 6 are described infra.

In some embodiments, the present invention provides compound 6:

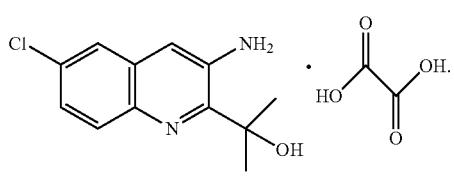

In some embodiments, the present invention provides compound 6, wherein said compound is crystalline.

In some embodiments, the present invention provides compound 6, wherein said compound is a crystalline solid substantially free of amorphous compound 6.

In some embodiments, the present invention provides compound 6, wherein said compound is substantially free of impurities.

In some embodiments, the present invention provides compound 6, wherein said compound has one or more peaks in its XRPD selected from those at about 16.9, about 19.8 and about 25.3 degrees 2-theta. In some such embodiments, the present invention provides compound 6, wherein said compound has at least two peaks in its XRPD selected from those at about 16.9, about 19.8 and about 25.3 degrees 2-theta. In some such embodiments, the present invention provides compound 6, wherein said compound is of Form A.

In some embodiments, the present invention provides compound 6, wherein said compound has an XRPD substantially similar to that depicted in FIG. 18.

In some embodiments, the present invention provides a composition comprising compound 6 and a pharmaceutically acceptable carrier or excipient.

In some embodiments, the present invention provides a method of inhibiting or preventing the accumulation of A2E in a patient comprising administering to said patient compound 6 or composition thereof.

In some embodiments, the present invention provides a method of treating various conditions in a patient in which aldehyde toxicity is implicated in the pathogenesis, comprising administering to said patient compound 6 or a crystal form as described herein. In some embodiments, the present invention provides a method of treating one or more of the diseases, disorders, or conditions described herein.

Compound 7 (Phosphate Salts of Compound A)

According to one embodiment, the present invention provides a phosphate salt of compound A, represented by compound 7:

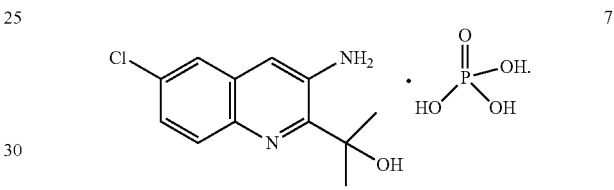

It will be appreciated by one of ordinary skill in the art that the phosphoric acid and compound A are ionically bonded to form compound 7. It is contemplated that compound 7 can exist in a variety of physical forms. For example, compound 7 can be in solution, suspension, or in solid form. In certain embodiments, compound 7 is in solid form. When compound 7 is in solid form, said compound may be amorphous, crystalline, or a mixture thereof. Exemplary solid forms are described in more detail below.

In some embodiments, the present invention provides compound 7 substantially free of impurities. As used herein, the term "substantially free of impurities" means that the compound contains no significant amount of extraneous matter. Such extraneous matter may include excess phosphoric acid, excess compound A, residual solvents, or any other impurities that may result from the preparation of, and/or isolation of, compound 7. In certain embodiments, at least about 95% by weight of compound 7 is present. In still other embodiments of the invention, at least about 99% by weight of compound 7 is present.

According to one embodiment, compound 7 is present in an amount of at least about 97, 97.5, 98.0, 98.5, 99, 99.5, 99.8 weight percent where the percentages are based on the total weight of the composition. According to another embodiment, compound 7 contains no more than about 3.0 area percent HPLC of total organic impurities and, in certain embodiments, no more than about 1.5 area percent HPLC total organic impurities relative to the total area of the HPLC chromatogram. In other embodiments, compound 7 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 7 is also meant to include all tautomeric forms of compound 7. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 7 can exist in a variety of solid forms. Exemplary such forms include polymorphs such as those described herein.

In certain embodiments, compound 7 is a crystalline solid. In other embodiments, compound 7 is a crystalline solid substantially free of amorphous compound 7. As used herein, the term "substantially free of amorphous compound 7" means that the compound contains no significant amount of amorphous compound 7. In certain embodiments, at least about 95% by weight of crystalline compound 7 is present. In still other embodiments of the invention, at least about 99% by weight of crystalline compound 7 is present.

In some embodiments, compound 7 is amorphous. In some embodiments, compound 7 is amorphous, and is substantially free of crystalline compound 7.

Form A of Compound 7

In some embodiments, Form A of compound 7 has at least 1, 2, 3, 4 or 5 spectral peak(s) selected from the peaks listed in Table 11 below.

TABLE 11

XRPD Peak Positions for Form A of Compound 7

| Position (°2θ) | Intensity % |
| --- | --- |
| 8.1 | 10.6 |
| 8.9 | 7.1 |
| 9.7 | 9.4 |
| 15.9 | 6.6 |
| 16.1 | 33.2 |
| 16.8 | 48.7 |
| 17.7 | 42.1 |
| 18.1 | 12.8 |
| 18.2 | 12.6 |
| 18.7 | 5.0 |
| 19.3 | 22.5 |
| 19.5 | 16.5 |
| 20.3 | 6.1 |
| 20.9 | 34.6 |
| 21.2 | 10.0 |
| 24.0 | 25.6 |
| 24.3 | 72.5 |
| 24.7 | 6.7 |
| 26.1 | 10.3 |
| 26.3 | 22.0 |
| 27.8 | 100.0 |
| 30.5 | 12.5 |
| 31.5 | 31.2 |
| 31.8 | 11.4 |
| 32.3 | 11.0 |
| 33.7 | 17.5 |

[1] In this and all subsequent tables, the position 2θ is within ±0.2.

In some embodiments, Form A of compound 7 is characterized in that it has one or more peaks in its X-ray powder diffraction pattern selected from those at about 16.8, about 24.3 and about 27.8 degrees 2-theta. In some embodiments, Form A of compound 7 is characterized in that it has two or more peaks in its X-ray powder diffraction pattern selected from those at about 16.8, about 24.3 and about 27.8 degrees 2-theta. In some embodiments, Form A of compound 7 is characterized in that it has all three peaks in its X-ray powder diffraction pattern selected from those at about 16.8, about 24.3 and about 27.8 degrees 2-theta.

Figure 20:
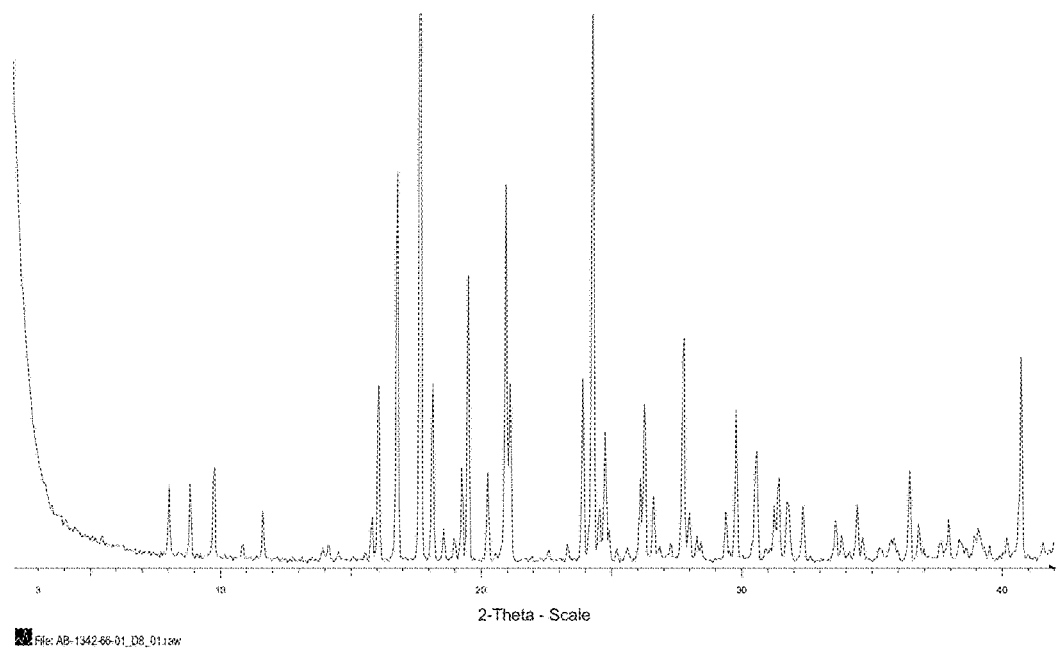
FIG. 20 depicts the XRPD pattern of Compound 7, Form A.

In certain embodiments, the X-ray powder diffraction pattern is substantially similar to the XRPD provided in FIG. 20.

Methods for preparing Form A of compound 7 are described infra.

In some embodiments, the present invention provides compound 7:

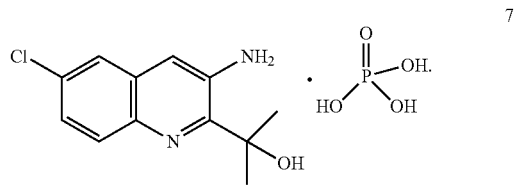

In some embodiments, the present invention provides compound 7, wherein said compound is crystalline.

In some embodiments, the present invention provides compound 7, wherein said compound is a crystalline solid substantially free of amorphous compound 7.

In some embodiments, the present invention provides compound 7, wherein said compound is substantially free of impurities.

In some embodiments, the present invention provides compound 7, wherein said compound has one or more peaks in its XRPD selected from those at about 16.8, about 24.3 and about 27.8 degrees 2-theta. In some such embodiments, the present invention provides compound 7, wherein said compound has at least two peaks in its XRPD selected from those at about 16.8, about 24.3 and about 27.8 degrees 2-theta. In some such embodiments, the present invention provides compound 7, wherein said compound is of Form A.

In some embodiments, the present invention provides compound 7, wherein said compound has an XRPD substantially similar to that depicted in FIG. 20.

In some embodiments, the present invention provides a composition comprising compound 7 and a pharmaceutically acceptable carrier or excipient.

In some embodiments, the present invention provides a method of inhibiting or preventing the accumulation of A2E in a patient comprising administering to said patient compound 7 or composition thereof.

In some embodiments, the present invention provides a method of treating various conditions in a patient in which aldehyde toxicity is implicated in the pathogenesis, comprising administering to said patient compound 7 or a crystal form as described herein. In some embodiments, the present invention provides a method of treating one or more of the diseases, disorders, or conditions described herein.

Compound 8 (Camsylate Salts of Compound A)

According to one embodiment, the present invention provides a camsylate salt of compound A, represented by compound 8:

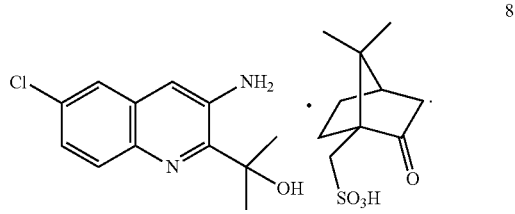

It will be appreciated by one of ordinary skill in the art that the camphorsulfonic acid and compound A are ionically bonded to form compound 8. It is contemplated that compound 8 can exist in a variety of physical forms. For example, compound 8 can be in solution, suspension, or in solid form. In certain embodiments, compound 8 is in solid form. When compound 8 is in solid form, said compound may be amorphous, crystalline, or a mixture thereof. Exemplary solid forms are described in more detail below.

In some embodiments, the present invention provides compound 8 substantially free of impurities. As used herein, the term "substantially free of impurities" means that the compound contains no significant amount of extraneous matter. Such extraneous matter may include excess camphorsulfonic acid, excess compound A, residual solvents, or any other impurities that may result from the preparation of, and/or isolation of, compound 8. In certain embodiments, at least about 95% by weight of compound 8 is present. In still other embodiments of the invention, at least about 99% by weight of compound 8 is present.

According to one embodiment, compound 8 is present in an amount of at least about 97, 97.5, 98.0, 98.5, 99, 99.5, 99.8 weight percent where the percentages are based on the total weight of the composition. According to another embodiment, compound 8 contains no more than about 3.0 area percent HPLC of total organic impurities and, in certain embodiments, no more than about 1.5 area percent HPLC total organic impurities relative to the total area of the HPLC chromatogram. In other embodiments, compound 8 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 8 is also meant to include all tautomeric forms of compound 8. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 8 can exist in a variety of solid forms. Exemplary such forms include polymorphs such as those described herein.

In certain embodiments, compound 8 is a crystalline solid. In other embodiments, compound 8 is a crystalline solid substantially free of amorphous compound 8. As used herein, the term "substantially free of amorphous compound 8" means that the compound contains no significant amount of amorphous compound 8. In certain embodiments, at least about 95% by weight of crystalline compound 8 is present. In still other embodiments of the invention, at least about 99% by weight of crystalline compound 8 is present.

In some embodiments, compound 8 is amorphous. In some embodiments, compound 8 is amorphous, and is substantially free of crystalline compound 8.

Form A of Compound 8

In some embodiments, Form A of compound 8 has at least 1, 2, 3, 4 or 5 spectral peak(s) selected from the peaks listed in Table 12 below.

TABLE 12

XRPD Peak Positions for Form A of Compound 8

| Position (°2θ) | Intensity % |
|---|---|
| 5.6 | 8.8 |
| 7.1 | 100.0 |
| 8.8 | 5.2 |
| 10.3 | 14.3 |
| 11.9 | 5.4 |
| 14.1 | 14.4 |
| 14.3 | 5.2 |
| 15.2 | 4.9 |
| 15.3 | 6.9 |
| 15.5 | 4.1 |
| 17.2 | 25.7 |
| 17.6 | 5.1 |
| 18.1 | 6.9 |
| 18.2 | 6.3 |
| 18.4 | 20.6 |
| 18.7 | 6.9 |
| 18.8 | 8.0 |
| 19.2 | 3.2 |
| 20.2 | 7.7 |
| 22.2 | 9.7 |
| 24.2 | 11.1 |
| 24.7 | 8.9 |

[1] In this and all subsequent tables, the position 2θ is within ±0.2.

In some embodiments, Form A of compound 8 is characterized in that it has one or more peaks in its X-ray powder diffraction pattern selected from those at about 7.1, about 17.2 and about 18.4 degrees 2-theta. In some embodiments, Form A of compound 8 is characterized in that it has two or more peaks in its X-ray powder diffraction pattern selected from those at about 7.1, about 17.2 and about 18.4 degrees 2-theta. In some embodiments, Form A of compound 8 is characterized in that it has all three peaks in its X-ray powder diffraction pattern selected from those at about 7.1, about 17.2 and about 18.4 degrees 2-theta.

Figure 22:
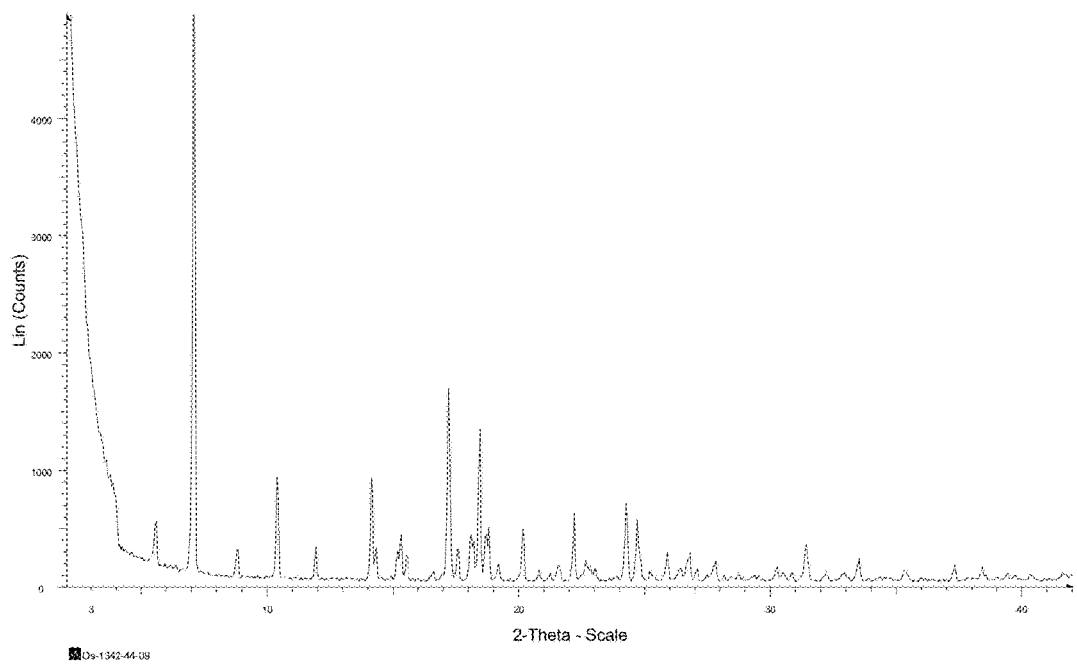
FIG. 22 depicts the XRPD pattern of Compound 8, Form A.

In certain embodiments, the X-ray powder diffraction pattern is substantially similar to the XRPD provided in FIG. 22.

Methods for preparing Form A of compound 8 are described infra.

In some embodiments, the present invention provides compound 8:

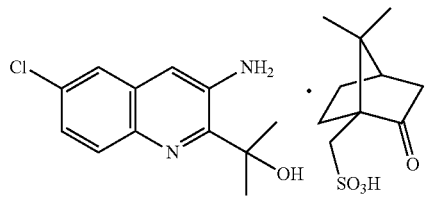

8

In some embodiments, the present invention provides compound 8, wherein said compound is crystalline.

In some embodiments, the present invention provides compound 8, wherein said compound is a crystalline solid substantially free of amorphous compound 8.

In some embodiments, the present invention provides compound 8, wherein said compound is substantially free of impurities.

In some embodiments, the present invention provides compound 8, wherein said compound has one or more peaks in its XRPD selected from those at about 7.1, about 17.2 and about 18.4 degrees 2-theta. In some such embodiments, the present invention provides compound 8, wherein said compound has at least two peaks in its XRPD selected from those at about 7.1, about 17.2 and about 18.4 degrees 2-theta. In some such embodiments, the present invention provides compound 8, wherein said compound is of Form A.

In some embodiments, the present invention provides compound 8, wherein said compound has an XRPD substantially similar to that depicted in FIG. 22.

In some embodiments, the present invention provides a composition comprising compound 8 and a pharmaceutically acceptable carrier or excipient.

In some embodiments, the present invention provides a method of inhibiting or preventing the accumulation of A2E in a patient comprising administering to said patient compound 8 or composition thereof.

In some embodiments, the present invention provides a method of treating various conditions in a patient in which aldehyde toxicity is implicated in the pathogenesis, comprising administering to said patient compound 8 or a crystal form as described herein. In some embodiments, the present invention provides a method of treating one or more of the diseases, disorders, or conditions described herein.

Compound 9 (Tartrate Salts of Compound A)

According to one embodiment, the present invention provides a tartrate salt of compound A, represented by compound 9:

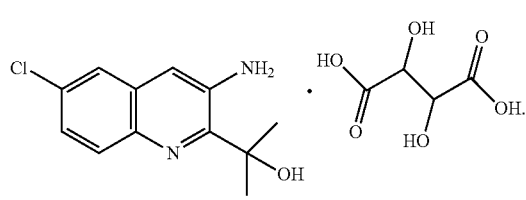

It will be appreciated by one of ordinary skill in the art that the tartaric acid and compound A are ionically bonded to form compound 9. It is contemplated that compound 9 can exist in a variety of physical forms. For example, compound 9 can be in solution, suspension, or in solid form. In certain embodiments, compound 9 is in solid form. When compound 9 is in solid form, said compound may be amorphous, crystalline, or a mixture thereof. Exemplary solid forms are described in more detail below.

In some embodiments, the present invention provides compound 9 substantially free of impurities. As used herein, the term "substantially free of impurities" means that the compound contains no significant amount of extraneous matter. Such extraneous matter may include excess tartaric acid, excess compound A, residual solvents, or any other impurities that may result from the preparation of, and/or isolation of, compound 9. In certain embodiments, at least about 95% by weight of compound 9 is present. In still other embodiments of the invention, at least about 99% by weight of compound 9 is present.

According to one embodiment, compound 9 is present in an amount of at least about 97, 97.5, 98.0, 98.5, 99, 99.5, 99.8 weight percent where the percentages are based on the total weight of the composition. According to another embodiment, compound 9 contains no more than about 3.0 area percent HPLC of total organic impurities and, in certain embodiments, no more than about 1.5 area percent HPLC total organic impurities relative to the total area of the HPLC chromatogram. In other embodiments, compound 9 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 9 is also meant to include all tautomeric forms of compound 9. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 9 can exist in a variety of solid forms. Exemplary such forms include polymorphs such as those described herein.

In certain embodiments, compound 9 is a crystalline solid. In other embodiments, compound 9 is a crystalline solid substantially free of amorphous compound 9. As used herein, the term "substantially free of amorphous compound 9" means that the compound contains no significant amount of amorphous compound 9. In certain embodiments, at least about 95% by weight of crystalline compound 9 is present. In still other embodiments of the invention, at least about 99% by weight of crystalline compound 9 is present.

In some embodiments, compound 9 is amorphous. In some embodiments, compound 9 is amorphous, and is substantially free of crystalline compound 9.

Form A of Compound 9

In some embodiments, Form A of compound 9 has at least 1, 2, 3, 4 or 5 spectral peak(s) selected from the peaks listed in Table 13 below.

TABLE 13

| XRPD Peak Positions for Form A of Compound 9 | |
|---|---|
| Position (°2θ) | Intensity % |
| 7.2 | 69.6 |
| 8.1 | 83.8 |
| 13.8 | 23.6 |
| 14.6 | 37.8 |
| 15.4 | 66.2 |
| 15.6 | 34.5 |
| 16.1 | 84.5 |
| 16.6 | 36.5 |
| 17.1 | 31.1 |
| 17.3 | 52.0 |
| 18.4 | 45.3 |
| 19.0 | 62.2 |
| 19.2 | 31.1 |
| 19.6 | 51.4 |
| 19.9 | 45.3 |

[1] In this and all subsequent tables, the position 2θ is within ±0.2.

In some embodiments, Form A of compound 9 is characterized in that it has one or more peaks in its X-ray powder diffraction pattern selected from those at about 7.2, about 8.1 and about 16.1 degrees 2-theta. In some embodiments, Form A of compound 9 is characterized in that it has two or more peaks in its X-ray powder diffraction pattern selected from those at about 7.2, about 8.1 and about 16.1 degrees 2-theta. In some embodiments, Form A of compound 9 is characterized in that it has all three peaks in its X-ray powder diffraction pattern selected from those at about 7.2, about 8.1 and about 16.1 degrees 2-theta.

Figure 24:
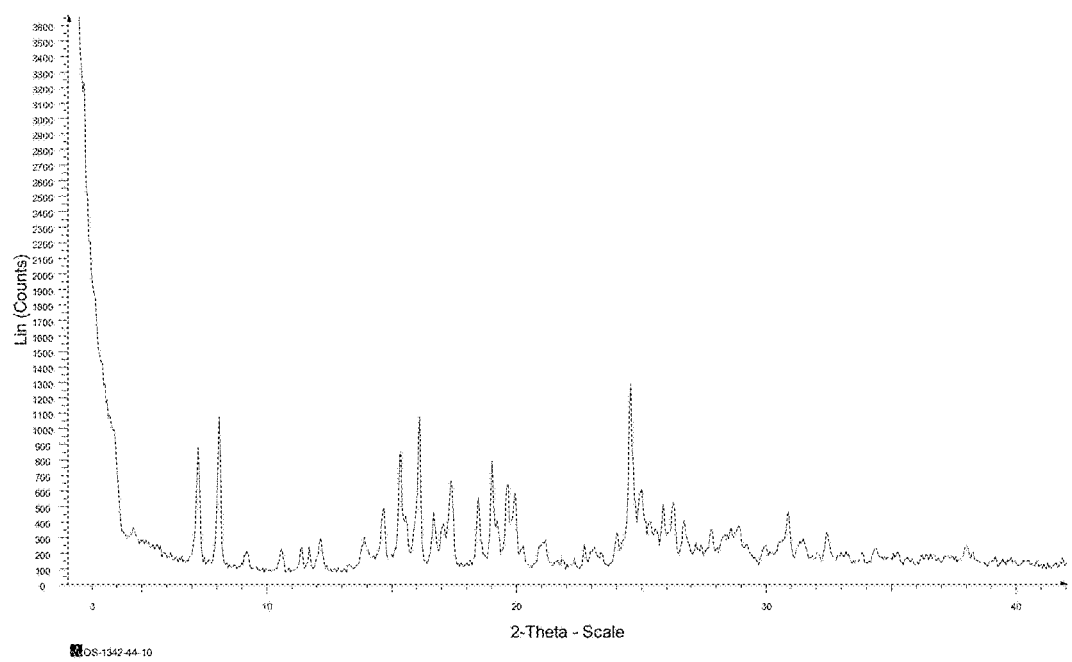
FIG. 24 depicts the XRPD pattern of Compound 9, Form A.

In certain embodiments, the X-ray powder diffraction pattern is substantially similar to the XRPD provided in FIG. 24.

Methods for preparing Form A of compound 9 are described infra.

In some embodiments, the present invention provides compound 9:

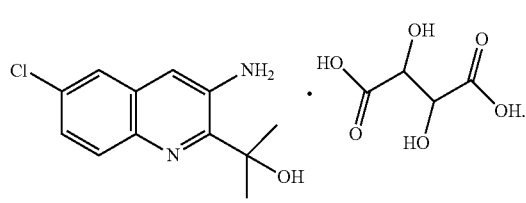

In some embodiments, the present invention provides compound 9, wherein said compound is crystalline.

In some embodiments, the present invention provides compound 9, wherein said compound is a crystalline solid substantially free of amorphous compound 9.

In some embodiments, the present invention provides compound 9, wherein said compound is substantially free of impurities.

In some embodiments, the present invention provides compound 9, wherein said compound has one or more peaks in its XRPD selected from those at about 7.2, about 8.1 and about 16.1 degrees 2-theta. In some such embodiments, the present invention provides compound 9, wherein said compound has at least two peaks in its XRPD selected from those at about 7.2, about 8.1 and about 16.1 degrees 2-theta. In some such embodiments, the present invention provides compound 9, wherein said compound is of Form A.

In some embodiments, the present invention provides compound 9, wherein said compound has an XRPD substantially similar to that depicted in FIG. 24.

In some embodiments, the present invention provides a composition comprising compound 9 and a pharmaceutically acceptable carrier or excipient.

In some embodiments, the present invention provides a method of inhibiting or preventing the accumulation of A2E in a patient comprising administering to said patient compound 9 or composition thereof.

In some embodiments, the present invention provides a method of treating various conditions in a patient in which aldehyde toxicity is implicated in the pathogenesis, comprising administering of compound 9 or composition thereof to said patient. In some such embodiments, the various conditions, in a patient, in which aldehyde toxicity is implicated in the pathogenesis may include dry eye, cataracts, keratoconus, Fuch's endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus), cardiovascular disorders (e.g., atherosclerosis), and conditions associated with the injurious effects of blister agents.

In some embodiments, the present invention provides a compound selected from: compound A, Form A; compound A, Form B; compound 1, Form A; compound 1, Form B; compound 2, Form A; compound 2, Form B; compound 3, Form A; compound 4, Form A; compound 5, Form A; compound 6, Form A; compound 7, Form A; compound 8, Form A and compound 9, Form A. In some such embodiments, the present invention provides a composition comprising one of the above compound forms and a pharmaceutically acceptable carrier or excipient. In some such embodiments, the present invention provides a method of treating one or more of the diseases, disorders, or conditions described herein.

General Methods of Providing a Salt Compound

Compound A is prepared according to the methods described in detail in the '500 publication, the entirety of which is hereby incorporated herein by reference. Salt compounds of general formula X, which formula encompasses, inter alia, salt compounds 1 through 9, and/or particular forms thereof, are prepared from compound A, according to the general Scheme below.

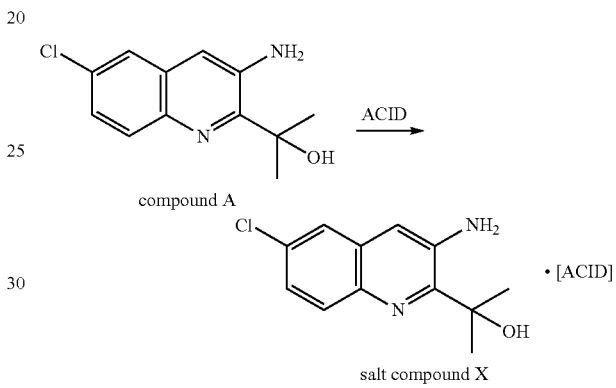

For instance, each of compounds 1 through 9, and forms thereof, are prepared from compound A by combining compound A with an appropriate acid to form a salt of that acid. Thus, another aspect of the present invention provides a method for preparing compounds 1 through 9, and forms thereof.

As described generally above, in some embodiments, the present invention provides a method for preparing a salt compound of the general formula X:

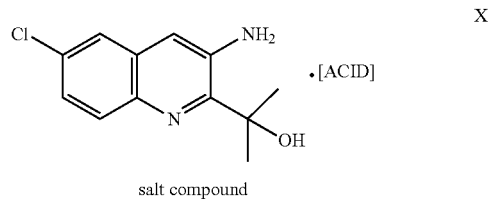

comprising steps of:
  combining compound A:

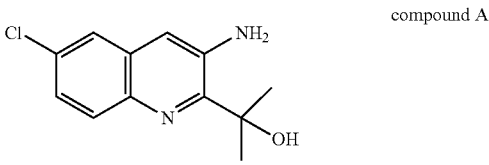 [SMILES: CC(C)(O)c1nc2ccc(Cl)cc2cc1N]

with a suitable acid and optionally a suitable solvent under conditions suitable for forming a salt compound of general formula X.

In some embodiments, a suitable acid is methanesulfonic acid. In some embodiments, the present invention provides a method of making a mesylate salt of compound A. In certain embodiments, the mesylate salt of compound A is compound 1. In certain embodiments, the mesylate salt of compound A is Form A of compound 1. In certain embodiments, the mesylate salt of compound A is Form B of compound 1.

In some embodiments, a suitable acid is benzenesulfonic acid. In some embodiments, the present invention provides a method of making a besylate salt of compound A. In certain embodiments, the besylate salt of compound A is compound 2. In certain embodiments, the besylate salt of compound A is Form A of compound 2. In certain embodiments, the besylate salt of compound A is Form B of compound 2.

In some embodiments, a suitable acid is sulfuric acid. In some embodiments, the present invention provides a method of making a sulfate salt of compound A. In certain embodiments, the sulfate salt of compound A is compound 3. In certain embodiments, the sulfate salt of compound A is Form A of compound 3.

In some embodiments, a suitable acid is p-toluenesulfonic acid. In some embodiments, the present invention provides a method of making a tosylate salt of compound A. In certain embodiments, the tosylate salt of compound A is compound 4. In certain embodiments, the tosylate salt of compound A is Form A of compound 4.

In some embodiments, a suitable acid is hydrochloric acid. In some embodiments, the present invention provides a method of making a hydrochloride salt of compound A. In certain embodiments, the hydrochloric salt of compound A is compound 5. In certain embodiments, the hydrochloride salt of compound A is Form A of compound 5.

In some embodiments, a suitable acid is oxalic acid. In some embodiments, the present invention provides a method of making an oxalate salt of compound A. In certain embodiments, the oxalate salt of compound A is compound 6. In certain embodiments, the oxalate salt of compound A is Form A of compound 6.

In some embodiments, a suitable acid is phosphoric acid. In some embodiments, the present invention provides a method of making a phosphate salt of compound A. In certain embodiments, the phosphate salt of compound A is compound 7. In certain embodiments, the phosphate salt of compound A is Form A of compound 7.

In some embodiments, a suitable acid is camphorsulfonic acid. In some embodiments, the present invention provides a method of making a camsylate salt of compound A. In certain embodiments, the camsylate salt of compound A is compound 8. In certain embodiments, the camsylate salt of compound A is Form A of compound 8.

In some embodiments, a suitable acid is tartaric acid. In some embodiments, the present invention provides a method of making a tartrate salt of compound A. In certain embodiments, the tartrate salt of compound A is compound 9. In certain embodiments, the tartrate salt of compound A is Form A of compound 9.

A suitable solvent may be any solvent system (e.g., one solvent or a mixture of solvents) in which compound A and/or an acid are soluble, or are at least partially soluble.

Examples of suitable solvents useful in the present invention include, but are not limited to protic solvents, aprotic solvents, polar aprotic solvent, or mixtures thereof. In certain embodiments, suitable solvents include an ether, an ester, an alcohol, a ketone, or a mixture thereof. In some embodiments, the solvent is one or more organic alcohols. In some embodiments, the solvent is chlorinated. In some embodiments, the solvent is an aromatic solvent.

In certain embodiments, a suitable solvent is methanol, ethanol, isopropanol, or acetone wherein said solvent is anhydrous or in combination with water or heptane. In some embodiments, suitable solvents include tetrahydrofuran, dimethylformamide, dimethylsulfoxide, glyme, diglyme, methyl t-butyl ether, t-butanol, n-butanol, and acetonitrile. In some embodiments, a suitable solvent is ethanol. In some embodiments, a suitable solvent is anhydrous ethanol. In some embodiments, the suitable solvent is MTBE.

In some embodiments, a suitable solvent is ethyl acetate. In some embodiments, a suitable solvent is a mixture of methanol and methylene chloride. In some embodiments, a suitable solvent is a mixture of acetonitrile and water. In certain embodiments, a suitable solvent is methyl acetate, isopropyl acetate, acetone, or tetrahydrofuran. In certain embodiments, a suitable solvent is diethylether. In certain embodiments, a suitable solvent is water. In certain embodiments, a suitable solvent is methyl ethyl ketone. In certain embodiments, a suitable solvent is toluene.

In some embodiments, the present invention provides a method for preparing a salt compound of the general formula X, comprising one or more steps of removing a solvent and adding a solvent. In some embodiments, an added solvent is the same as the solvent removed. In some embodiments, an added solvent is different from the solvent removed. Means of solvent removal are known in the synthetic and chemical arts and include, but are not limited to, any of those described herein and in the Exemplification.

In some embodiments, a method for preparing a salt compound of the general formula X comprises one or more steps of heating or cooling a preparation.

In some embodiments, a method for preparing a salt compound of the general formula X comprises one or more steps of agitating or stirring a preparation.

In some embodiments, a method for preparing a salt compound of the general formula X comprises a step of adding a suitable acid to a solution or slurry of compound A.

In some embodiments, a method for preparing a salt compound of the general formula X comprises a step of heating.

In certain embodiments, a salt compound of formula X precipitates from the mixture. In another embodiment, a salt compound of formula X crystallizes from the mixture. In other embodiments, a salt compound of formula X crystallizes from solution following seeding of the solution (i.e., adding crystals of a salt compound of formula X to the solution).

A salt compound of formula X can precipitate out of the reaction mixture, or be generated by removal of part or all of the solvent through methods such as evaporation, distillation, filtration (ex. nanofiltration, ultrafiltration), reverse osmosis, absorption and reaction, by adding an anti-solvent such as heptane, by cooling or by different combinations of these methods.

As described generally above, a salt compound of formula X is optionally isolated. It will be appreciated that a salt compound of formula X may be isolated by any suitable physical means known to one of ordinary skill in the art. In certain embodiments, precipitated solid salt compound of formula X is separated from the supernatant by filtration. In other embodiments, precipitated solid salt compound of formula X is separated from the supernatant by decanting the supernatant.

In certain embodiments, a salt compound of formula X is separated from the supernatant by filtration.

In certain embodiments, an isolated salt compound of formula X is dried in air. In other embodiments, isolated salt compound of formula X is dried under reduced pressure, optionally at elevated temperature.

Uses of Compounds and Pharmaceutically Acceptable Compositions Thereof

Certain compounds described herein are found to be useful in scavenging toxic aldehydes, such as MDA and HNE. The compounds described herein undergo a Schiff base condensation with MDA, HNE, or other toxic aldehydes, and form a complex with the aldehydes in an energetically favorable reaction, thus decreasing or eliminating aldehydes available for reaction with a protein, lipid, carbohydrate, or DNA. Importantly, compounds described herein can react with aldehydes to form a compound having a closed-ring structure that contains the aldehydes, thus trapping the aldehydes and preventing the aldehydes from being released back into the cellular milieu.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent, delay or lessen the severity of their recurrence.

The invention relates to compounds described herein for the treatment, prevention, and/or reduction of a risk of diseases, disorders, or conditions in which aldehyde toxicity is implicated in the pathogenesis.

Examples of the diseases, disorders, or conditions in which aldehyde toxicity is implicated include an ocular disease, disorder, or condition, including, but not limited to, a corneal disease (e.g., dry eye syndrome, cataracts, keratoconus, bullous and other keratopathy, and Fuch's endothelial dystrophy), other ocular disorders or conditions (e.g., allergic conjunctivitis, ocular cicatricial pemphigoid, conditions associated with PRK healing and other corneal healing, and conditions associated with tear lipid degradation or lacrimal gland dysfunction), and other ocular conditions associated with high aldehyde levels as a result of inflammation (e.g., uveitis, scleritis, ocular Stevens-Johnson Syndrome, ocular rosacea (with or without meibomian gland dysfunction)). In one example, the ocular disease, disorder, or condition is not macular degeneration, such as age-related macular degeneration ("AMD"), or Stargardt's disease. In a further example, the ocular disease, disorder, or condition is dry eye syndrome, ocular rosacea, or uveitis.

Examples of the diseases, disorders, conditions, or indications in which aldehyde toxicity is implicated also include non-ocular disorders, including psoriasis, topical (discoid) lupus, contact dermatitis, atopic dermatitis, allergic dermatitis, radiation dermatitis, acne vulgaris, Sjögren-Larsson Syndrome and other ichthyoses, solar elastosis/wrinkles, skin tone firmness, puffiness, eczema, smoke or irritant induced skin changes, dermal incision, a skin condition associated burn and/or wound, lupus, scleroderma, asthma, chronic obstructive pulmonary disease (COPD), rheumatoid arthritis, inflammatory bowel disease, sepsis, atherosclerosis, ischemic-reperfusion injury, Parkinson's disease, Alzheimer's disease, succinic semialdehyde dehydrogenase deficiency, multiple sclerosis, amyotrophic lateral sclerosis, diabetes, metabolic syndrome, age-related disorders, and fibrotic diseases. In a further example, the non-ocular disorder is a skin disease, disorder, or condition selected from contact dermatitis, atopic dermatitis, allergic dermatitis, and. radiation dermatitis. In another example, the non-ocular disorder is a skin disease, disorder, or condition selected from Sjögren-Larsson Syndrome and a cosmetic indication associated burn and/or wound.

In a further example, the diseases, disorders, or conditions in which aldehyde toxicity is implicated are an age-related disorder. Examples of age-related diseases, disorders, or conditions include wrinkles, dryness, and pigmentation of the skin.

Examples of the diseases, disorders, or conditions in which aldehyde toxicity is implicated further include conditions associated with the toxic effects of blister agents or burns from alkali agents. The compounds described herein decrease or eliminate toxic aldehydes and thus treat, prevent, and/or reduce a risk of these diseases or disorders.

In one embodiment, the invention relates to the treatment, prevention, and/or reduction of a risk of an ocular disease, disorder, or condition in which aldehyde toxicity is implicated in the pathogenesis, comprising administering to a subject in need thereof a compound described herein. The ocular disease, disorder, or condition includes, but is not limited to, a corneal disease (e.g., dry eye syndrome, cataracts, keratoconus, bullous and other keratopathy, and Fuch's endothelial dystrophy in the cornea), other ocular disorders or conditions (e.g., allergic conjunctivitis, ocular cicatricial pemphigoid, conditions associated with PRK healing and other corneal healing, and conditions associated with tear lipid degradation or lacrimal gland dysfunction), and other ocular conditions where inflammation leads to high aldehyde levels (e.g., uveitis, scleritis, ocular Stevens-Johnson Syndrome, ocular rosacea (with or without meibomian gland dysfunction)). The ocular disease, disorder, or condition does not include macular degeneration, such as AMD, or Stargardt's disease. In one illustration, in the ocular disease, disorder, or condition, the amount or concentration of MDA or HNE is increased in the ocular tissues or cells. For example, the amount or concentration of aldehydes (e.g., MDA or HNE) is increased at least 1.1-fold, 1.2-fold, 1.3-fold, 1.4-fold, 1.5-fold, 2-fold, 2.5-fold, 5-fold, 10-fold as compared to that in normal ocular tissues or cells. Compounds described herein, such as Compound 1, decrease aldehyde (e.g., MDA and HNE) concentration in a time-dependent manner. The amount or concentration of aldehydes (e.g., MDA or HNE) can be measured by methods or techniques known in the art, such as those described in Tukozkan et al., Furat Tip Dergisi 11: 88-92 (2006).

In one class, the ocular disease, disorder, or condition is dry eye syndrome. In a second class, the ocular disease, disorder, or condition is a condition associated with PRK healing and other corneal healing. For example, the invention is directed to advancing PRK healing or other corneal healing, comprising administering to a subject in need thereof a compound described herein. In a third class, the ocular disease, disorder, or condition is an ocular condition associated with high aldehyde levels resulting from inflammation (e.g., uveitis, scleritis, ocular Stevens-Johnson Syndrome, and ocular rosacea (with or without meibomian gland dysfunction). In a fourth class, the ocular disease, disorder, or condition is keratoconus, cataracts, bullous and other keratopathy, Fuchs' endothelial dystrophy, ocular cicatricial pemphigoid, or allergic conjunctivitis. The compound described herein may be administered topically or systemically, as described herein below.

In a second embodiment, the invention relates to the treatment, prevention, and/or reduction of a risk of a skin disorder or condition or a cosmetic indication, in which aldehyde toxicity is implicated in the pathogenesis, comprising administering to a subject in need thereof a compound described herein. The skin disorder or condition includes, but is not limited to, psoriasis, scleroderma, topical (discoid) lupus, contact dermatitis, atopic dermatitis, allergic dermatitis, radiation dermatitis, acne vulgaris, and Sjögren-Larsson Syndrome and other ichthyosis, and the cosmetic indication is solar elastosis/wrinkles, skin tone firmness, puffiness, eczema, smoke or irritant induced skin changes, dermal incision, or a skin condition associated burn and/or wound. In some embodiments, the invention relates to age-related diseases, disorders, or conditions of the skin, as described herein.

Various skin disorders or conditions, such as atopic dermatitis, topical (discoid) lupus, psoriasis and scleroderma, are characterized by high MDA and HNE levels (Br J Dermatol 149: 248 (2003); JEADV 26: 833 (2012); Clin Rheumatol 25: 320 (2006)). In addition, ichthyosis characteristic of the Sjögren-Larsson Syndrome (SLS) originates from accumulation of fatty aldehydes, which disrupts the normal function and secretion of lamellar bodies (LB), leading to intercellular lipid deposits in the strateum corneum (SC) and a defective water barrier in the skin layer (W. B. Rizzo et al. (2010)). The enzyme, fatty aldehyde dehydrogenase, that metabolizes aldehydes is dysfunctional in SLS patients. Thus, compounds that decrease or eliminate aldehydes, such as the compounds described herein, can be used to treat, prevent, and/or reduce a risk of skin disorders or conditions in which aldehyde toxicity is implicated in the pathogenesis, such as those described herein. Furthermore, with an improvement to the water barrier and prevention of aldehyde-mediated inflammation (including fibrosis and elastosis (Chairpotto et al. (2005)), many cosmetic indications, such as solar elastosis/wrinkles, skin tone, firmness (puffiness), eczema, smoke or irritant induced skin changes and dermal incision cosmesis, and skin conditions associated with burn and/or wound can be treated using the method of the invention.

In one class, the skin disease, disorder, or condition is psoriasis, scleroderma, topical (discoid) lupus, contact dermatitis, atopic dermatitis, allergic dermatitis, radiation dermatitis, acne vulgaris, or Sjögren-Larsson Syndrome and other ichthyoses. In one exemplification, the skin disease, disorder, or condition is contact dermatitis, atopic dermatitis, allergic dermatitis, radiation dermatitis, or Sjögren-Larsson Syndrome and other ichthyoses. In a second class, the cosmetic indication is solar elastosis/wrinkles, skin tone firmness, puffiness, eczema, smoke or irritant induced skin changes, dermal incision, or a skin condition associated with burn and/or wound.

In a third embodiment, the invention relates to the treatment, prevention, and/or reduction of a risk of a condition associated with the toxic effects of blister agents or burns from alkali agents in which aldehyde toxicity is implicated in the pathogenesis, comprising administering to a subject in need thereof a compound described herein.

Blister agents include, but are not limited to, sulfur mustard, nitrogen mustard, and phosgene oxime. Toxic or injurious effects of blister agents include pain, irritation, and/or tearing in the skin, eye, and/or mucous, and conjunctivitis and/or corneal damage to the eye. Sulfur mustard is the compound bis(2-chloroethyl) sulfide. Nitrogen mustard includes the compounds bis(2-chloroethyl)ethylamine, bis(2-chloroethyl)methylamine, and tris(2-chloroethyl)amine. Sulfur mustard or its analogs can cause an increase in oxidative stress, and in particular HNE levels, and by depleting the antioxidant defense system and thereby increasing lipid peroxidation, may induce an oxidative stress response and thus increase aldehyde levels (Jafari et al. (2010); Pal et al. (2009)). Increased activities of antioxidant enzymes may be a compensatory response to reactive oxygen species generated by the sulfur mustard. Antioxidants, such as silibinin, when applied topically, attenuate skin injury induced from exposure to sulfur mustard or its analogs (Jafari et al. (2010); Tewari-Singh et al. (2012)). Further, intervention to reduce free radical species was an effective treatment, post-exposure, for phosgene-induced lung injury (Sciuto et al. (2004)). Thus, compounds that decrease or eliminate aldehydes, such as compounds described herein, can be used to treat, prevent, and/or reduce the risk of a condition associated with the toxic effects of blister agents, such as sulfur mustard, nitrogen mustard, and phosgene oxime.

Alkali agents include, but are not limited to, lime, lye, ammonia, and drain cleaners. Compounds that reduce or eliminate aldehydes, such as compounds described herein, can be used to treat, prevent, and/or reduce a risk of a condition associated with burns from an alkali agent.

In a fourth embodiment, the invention relates to the treatment, prevention, and/or reduction of a risk of an autoimmune, immune-mediated, inflammatory, cardiovascular, or neurological disease, disorder, or condition, or metabolic syndrome, or diabetes, in which aldehyde toxicity is implicated in the pathogenesis, comprising administering to a subject in need thereof a compound described herein. The autoimmune or immune-mediated disease, disorder, or condition includes, but is not limited to, lupus, scleroderma, asthma, chronic obstructive pulmonary disease (COPD), and rheumatoid arthritis. The inflammatory disease, disorder, or condition includes, but is not limited to, rheumatoid arthritis, inflammatory bowel disease (e.g., Crohn's disease and ulcerative colitis), sepsis, and fibrosis (e.g., renal, hepatic, pulmonary, and cardiac fibrosis). The cardiovascular disease, disorder, or condition includes, but is not limited to, atherosclerosis and ischemic-reperfusion injury. The neurological disease, disorder, or condition includes, but is not limited to, Parkinson's disease, Alzheimer's disease, succinic semialdehyde dehydrogenase, deficiency, multiple sclerosis, amyotrophic lateral sclerosis, and the neurological aspects of Sjögren-Larsson Syndrome (cognitive delay and spasticity).

A skilled person would understand that the disease, disorder, or condition listed herein may involve more than one pathological mechanism. For example, a disease, disorder, or condition listed herein may involve dysregulation in the immunological response and inflammatory response. Thus, the above categorization of a disease, disorder, or condition is not absolute, and the disease, disorder, or condition may be considered an immunological, an inflammatory, a cardiovascular, a neurological, and/or metabolic disease, disorder, or condition.

Individuals with deficiencies in aldehyde dehydrogenase are found to have high aldehyde levels and increased risk of Parkinson's disease (PNAS 110:636 (2013)) and Alzheimer's disease (BioChem Biophys Res Commun. 273:192 (2000)). In Parkinson's disease, aldehydes specifically interfere with dopamine physiology (Free Radic Biol Med, 51:

1302 (2011); Mol Aspects Med, 24: 293 (2003); Brain Res, 1145: 150 (2007)). In addition, aldehydes levels are elevated in multiple sclerosis, amyotrophic lateral sclerosis, autoimmune diseases such as lupus, rheumatoid arthritis, lupus, psoriasis, scleroderma, and fibrotic diseases, and increased levels of HNE, MDA, glyoxal, and methylglyoxal are implicated in the progression of atherosclerosis and diabetes (J. Cell. Mol. Med., 15: 1339 (2011); Arthritis Rheum 62: 2064 (2010); Clin Exp Immunol, 101: 233 (1995); Int J Rheum Dis, 14: 325 (2011); JEADV 26: 833 (2012); Clin Rheumatol 25: 320 (2006); Gut 54: 987 (2005); J Am Soc Nephrol 20: 2119 (2009); Curr. Aging Sci. 10:18 (2017); Oxid. Med. Cell Longev. Article 1625130 (2017)). MDA is further implicated in the increased formation of foam cells leading to atherosclerosis (Leibundgut et al., Current Opinion in Pharmacology 13: 168 (2013)). Also, aldehyde-related toxicity plays an important role in the pathogenesis of many inflammatory lung diseases, such as asthma and chronic obstructive pulmonary disease (COPD) (Bartoli et al., Mediators of Inflammation 2011, Article 891752). Thus, compounds that decrease or eliminate aldehydes, such as compounds described herein, can be used to treat, prevent, and/or reduce a risk of an autoimmune, immune-mediated, inflammatory, cardiovascular, or neurological disease, disorder, or condition, or metabolic syndrome, or diabetes. For example, compounds described herein prevent aldehyde-mediated cell death in neurons. Further, compounds described herein downregulate a broad spectrum of pro-inflammatory cytokines and/or upregulate anti-inflammatory cytokines, which indicates that compounds described herein are useful in treating inflammatory diseases, such as multiple sclerosis and amyotrophic lateral sclerosis.

As discussed above, a disclosed composition may be administered to a subject in order to treat or prevent macular degeneration and other forms of retinal disease whose etiology involves the accumulation of A2E and/or lipofuscin. Other diseases, disorders, or conditions characterized by the accumulation A2E may be similarly treated.

In one embodiment, a compound that reduces the formation of A2E is administered to a subject. For example, the compound may compete with PE for reaction with trans-RAL, thereby reducing the amount of A2E formed. In another embodiment, a compound that prevents the accumulation of A2E is administered to a subject. For example, the compound competes so successfully with PE for reaction with trans-RAL, no A2E is formed.

Individuals to be treated fall into three groups: (1) those who are clinically diagnosed with macular degeneration or other forms of retinal disease, whose etiology involves the accumulation of A2E and/or lipofuscin on the basis of visual deficits (including but not limited to dark adaptation, contrast sensitivity and acuity) as determined by visual examination and/or electroretinography, and/or retinal health as indicated by fundoscopic examination of retinal and RPE tissue for drusen accumulations, tissue atrophy and/or lipofuscin fluorescence; (2) those who are pre-symptomatic for macular degenerative disease but thought to be at risk based on abnormal results in any or all of the same measures; and (3) those who are pre-symptomatic but thought to be at risk genetically based on family history of macular degenerative disease and/or genotyping results showing one or more alleles or polymorphisms associated with the disease. The compositions are administered topically or systemically at one or more times per month, week or day. Dosages may be selected to avoid side effects, if any, on visual performance in dark adaptation. Treatment is continued for a period of at least one, three, six, or twelve or more months. Patients may be tested at one, three, six, or twelve months or longer intervals to assess safety and efficacy. Efficacy is measured by examination of visual performance and retinal health as described above.

In one embodiment, a subject is diagnosed as having symptoms of macular degeneration, and then a disclosed compound is administered. In another embodiment, a subject may be identified as being at risk for developing macular degeneration (risk factors include a history of smoking, age, female gender, and family history), and then a disclosed compound is administered. In another embodiment, a subject may have dry AMD in both eyes, and then a disclosed compound is administered. In another embodiment, a subject may have wet AMD in one eye but dry AMD in the other eye, and then a disclosed compound is administered. In yet another embodiment, a subject may be diagnosed as having Stargardt's disease and then a disclosed compound is administered. In another embodiment, a subject is diagnosed as having symptoms of other forms of retinal disease in which the etiology involves the accumulation of A2E and/or lipofuscin, and then the compound is administered. In another embodiment, a subject may be identified as being at risk for developing other forms of retinal disease in which the etiology involves the accumulation of A2E and/or lipofuscin, and then the disclosed compound is administered. In some embodiments, a compound is administered prophylactically. In some embodiments, a subject has been diagnosed as having the disease before retinal damage is apparent. For example, a subject is found to carry a gene mutation for ABCA4 and is diagnosed as being at risk for Stargardt's disease before any ophthalmologic signs are manifest, or a subject is found to have early macular changes indicative of macular degeneration before the subject is aware of any effect on vision. In some embodiments, a human subject may know that he or she is in need of the macular generation treatment or prevention.

In some embodiments, a subject may be monitored for the extent of macular degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

In some embodiments, the disclosed methods may be combined with other methods for treating or preventing macular degeneration or other forms of retinal disease in which the etiology involves the accumulation of A2E and/or lipofuscin, such as photodynamic therapy. For example, a patient may be treated with more than one therapy for one or more diseases or disorders. For example, a patient may have one eye afflicted with dry form AMD, which is treated with a compound of the invention, and the other eye afflicted with wet form AMD, which is treated with, e.g., photodynamic therapy.

In some embodiments, a compound for treating or preventing macular degeneration or other forms of retinal disease in which the etiology involves the accumulation of A2E and/or lipofuscin may be administered chronically. The compound may be administered daily, more than once daily, twice a week, three times a week, weekly, biweekly, monthly, bimonthly, semi-annually, annually, and/or biannually.

Sphingosine 1-phosphate, a bioactive signaling molecule with diverse cellular functions, is irreversibly degraded by the endoplasmic reticulum enzyme sphingosine 1-phosphate lyase, generating trans-2-hexadecenal and phosphoethanolamine. It has been demonstrated that trans-2-hexadecenal causes cytoskeletal reorganization, detachment, and apoptosis in multiple cell types via a JNK-dependent pathway. See Biochem Biophys Res Commun. 2012 Jul. 20; 424(1): 18-21. These findings and the known chemistry of related α,β-unsaturated aldehydes raise the possibility that trans-2-hexadecenal interact with additional cellular components. It was shown that it reacts readily with deoxyguanosine and DNA to produce the diastereomeric cyclic 1,N(2)-deoxyguanosine adducts 3-(2-deoxy-β-d-erythro-pentofuranosyl)-5,6,7,8-tetrahydro-8R-hydroxy-6R-tridecylpyrimido[1,2-a]purine-10(3H)one and 3-(2-deoxy-β-d-erythro-pentofuranosyl)-5,6,7,8-tetrahydro-8 S-hydroxy-6S-tridecylpyrimido[1,2-a]purine-10(3H)one. These findings demonstrate that trans-2-hexadecenal produced endogenously by sphingosine 1-phosphate lyase react directly with DNA, forming aldehyde-derived DNA adducts with potentially mutagenic consequences.

Succinic semialdehyde dehydrogenase deficiency (SSADHD), also known as 4-hydroxybutyric aciduria or gamma-hydroxybutyric aciduria, is the most prevalent autosomal-recessively inherited disorder of GABA metabolism (Vogel et al. 2013), manifests a phenotype of developmental delay and hypotonia in early childhood, and severe expressive language impairment and obsessive-compulsive disorder in adolescence and adulthood. Epilepsy occurs in half of patients, usually as generalized tonic-clonic seizures although sometimes absence and myoclonic seizures occur (Pearl et al. 2014). Greater than two-thirds of patients manifest neuropsychiatric problems (i.e., ADHD, OCD and aggression) in adolescence and adulthood, which can be disabling. Metabolically, there is accumulation of the major inhibitory neurotransmitter, GABA, and gamma-hydroxybutyrate (GHB), a neuromodulatory monocarboxylic acid (Snead and Gibson 2005). In addition, several other intermediates specific to this disorder have been detected both in patients and the corresponding murine model. Vigabatrin (VGB; γ-vinyl-GABA), an irreversible inhibitor of GABA-transaminase, is a logical choice for treatment of SSADH deficiency because it prevent the conversion of GABA to GHB by inhibiting GABA transaminase. Outcomes have been mixed, and in selected patients treatment has led to deterioration (Good 2011; Pellock 2011; Escalera et al. 2010; Casarano et al. 2011; Matern et al. 1996; Al-Essa et al. 2000). Targeted therapy for SSADH deficiency remains elusive and interventions palliative.

As discussed above, the compounds of the disclosure are used to treat inflammatory disorders. In some embodiments, the compounds are administered in a therapeutically effective amount to a subject to treat a systemic inflammatory disorder. In some embodiments, the systemic inflammatory disorder is non-alcoholic fatty liver disease (NAFLD), non-alcoholic steatohepatitis (NASH), inflammatory bowel disease (IBD) Crohn's disease, ulcerative colitis (UC), psoriasis, IBS (irritable bowel syndrome or spastic colon), including spastic colon, ankylosing spondylitis, osteoporosis, rheumatoid arthritis (RA), psoriatic arthritis, chronic obstructive pulmonary disease (COPD), interstitial lung disease (including idiopathic pulmonary fibrosis), atherosclerosis, psoriatic arthritis, pulmonary arterial hypertension, pyridoxine-dependent epilepsy, atopic dermatitis, rosacea, multiple sclerosis (MS), systemic lupus erythematosus (SLE), lupus nephritis, sepsis, eosinophilic esophagitis, chronic kidney disease (CKD), fibrotic renal disease, chronic eosinophilic pneumonia, extrinsic allergic alveolitis, pre-clampsia, endometriosis, polycystic ovary syndrome (PCOS), reduced female fertility, reduced sperm viability and motility, or cyclophosphamide-induced hemorrhagic cystitis.

In some embodiments, the compounds of the disclosure are used to treat a systemic disease, disorder, or condition. In some embodiments, the systemic disease, disorder, or condition is light chain deposition disease, IgA nephropathy, end stage renal disease, gout, pseudogout, diabetic nephropathy, diabetic neuropathy, traumatic brain injury, noise-induced hearing loss, Alzheimer's Disease, Parkinson's Disease, Huntington Disease, amyotrophic lateral sclerosis, primary biliary cirrhosis, primary sclerosing cholangitis, uterine leiomyoma, sarcoidosis, or chronic kidney disease. In some embodiments, the compounds of the disclosure are administered in an effective amount to treat non-alcoholic fatty liver disease (NAFLD).

In some embodiments, the compounds of the disclosure are administered in an effective amount to treat non-alcoholic steatohepatitis (NASH).

In some embodiments, the compounds of the disclosure are administered in an effective amount to treat inflammatory bowel disease (IBD).

In some embodiments, the compounds of the disclosure are administered in an effective amount to treat Crohn's disease.

In some embodiments, the compounds of the disclosure are administered in an effective amount to treat ulcerative colitis (UC).

In some embodiments, the compounds of the disclosure are administered in an effective amount to treat psoriasis.

In some embodiments, the compounds of the disclosure are administered in an effective amount to treat IBS (irritable bowel syndrome) or spastic colon.

In some embodiments, the compounds of the disclosure are administered in an effective amount to treat ankylosing spondylitis.

In some embodiments, the compounds of the disclosure are administered in an effective amount to treat osteoporosis.

In some embodiments, the compounds of the disclosure are administered in an effective amount to treat rheumatoid arthritis (RA).

In some embodiments, the compounds of the disclosure are administered in an effective amount to treat psoriatic arthritis.

In some embodiments, the compounds of the disclosure are administered in an effective amount to treat chronic obstructive pulmonary disease (COPD).

In some embodiments, the compounds of the disclosure are administered in an effective amount to treat interstitial lung disease (including idiopathic pulmonary fibrosis).

In some embodiments, the compounds of the disclosure are administered in an effective amount to treat atherosclerosis.

In some embodiments, the compounds of the disclosure are administered in an effective amount to treat psoriatic arthritis.

In some embodiments, the compounds of the disclosure are administered in an effective amount to treat pulmonary arterial hypertension.

In some embodiments, the compounds of the disclosure are administered in an effective amount to treat pyridoxine-dependent epilepsy.

In some embodiments, the compounds of the disclosure are administered in an effective amount to treat atopic dermatitis.

In some embodiments, the compounds of the disclosure are administered in an effective amount to treat rosacea.

In some embodiments, the compounds of the disclosure are administered in an effective amount to treat multiple sclerosis (MS).

In some embodiments, the compounds of the disclosure are administered in an effective amount to treat systemic lupus erythematosus (SLE).

In some embodiments, the compounds of the disclosure are administered in an effective amount to treat lupus nephritis.

In some embodiments, the compounds of the disclosure are administered in an effective amount to treat sepsis.

In some embodiments, the compounds of the disclosure are administered in an effective amount to treat eosinophilic esophagitis.

In some embodiments, the compounds of the disclosure are administered in an effective amount to treat chronic kidney disease (CKD).

In some embodiments, the compounds of the disclosure are administered in an effective amount to treat fibrotic renal disease.

In some embodiments, the compounds of the disclosure are administered in an effective amount to treat chronic eosinophilic pneumonia.

In some embodiments, the compounds of the disclosure are administered in an effective amount to treat extrinsic allergic alveolitis.

In some embodiments, the compounds of the disclosure are administered in an effective amount to treat pre-clampsia.

In some embodiments, the compounds of the disclosure are administered in an effective amount to treat endometriosis.

In some embodiments, the compounds of the disclosure are administered in an effective amount to treat polycystic ovary syndrome (PCOS).

In some embodiments, the compounds of the disclosure are administered in an effective amount to treat reduced female fertility.

In some embodiments, the compounds of the disclosure are administered in an effective amount to treat reduced sperm viability and motility.

In some embodiments, the compounds of the disclosure are administered in an effective amount to treat cyclophosphamide-induced hemorrhagic cystitis.

In some embodiments, the inflammatory disorder is an ocular inflammatory disorder. In some embodiments, the ocular inflammatory disorder is diabetic macular edema (DME), atopic keratoconjunctivitis (AKC), vernal keratoconjunctivitis (VKC), age-related macular degeneration (AMD), dry eye disease (DED), allergic conjunctivitis (AC), dry eye disease with allergic conjunctivitis, noninfectious anterior uveitis, posterior uveitis, pan-uveitis, post-surgical ocular pain and inflammation.

In some embodiments, the compound of the disclosure is administered in an effective amount for the prevention of corneal fibrosis after radial keratotomy, prevention of corneal fibrosis after trauma or exposure to vesicants, or prevention of corneal fibrosis after infection.

In some embodiments, the compounds of the disclosure are administered in an effective amount to treat diabetic macular edema (DME). In some embodiments, the diabetic macular edema for treatment is non-clinically significant macular edema (Non-CSME). In some embodiments, the diabetic macular edema for treatment is clinically significant macular edema (CSME).

In some embodiments, the compounds of the disclosure are administered in an effective amount to treat uveitis, including pan-uveitis, anterior uveitis, posterior uveitis, and non-infectious uveitis, which are ocular disorders that can be secondary to a primary underlying disorder. Some of the disorders with which uveitis is sometimes associated are Behçet's syndrome, ankylosing spondylitis, Lyme disease, sarcoidosis, and psoriasis. Uveitis is an inflammation of the iris, ciliary body, and choroid. It is associated with blurred vision; seeing dark, floating spots ("floaters"); eye pain; redness of the eye; and sensitivity to light (photophobia). A standard course of therapy for uveitis is a topical corticosteroid, and in some instances, a dilator such cyclopentolate, or an immunomodulatory agent.

In some embodiments, the compounds of the disclosure are administered in an effective amount to treat atopic keratoconjunctivitis (AKC) or vernal keratoconjunctivitis (VKC).

In some embodiments, the compounds of the disclosure are administered in an effective amount to treat age-related macular degeneration (AMD).

In some embodiments, the compounds of the disclosure are administered in an effective amount to treat dry eye disease (DED).

In some embodiments, the compounds of the disclosure are administered in an effective amount to treat allergic conjunctivitis (AC).

In some embodiments, the compounds of the disclosure are administered in an effective amount to treat dry eye disease with allergic conjunctivitis.

In some embodiments, the compounds of the disclosure are administered in an effective amount to treat post-surgical ocular pain and inflammation.

In some embodiments, the compounds of the disclosure are administered in an effective amount for prevention of corneal fibrosis after radial keratotomy.

In some embodiments, the compounds of the disclosure are administered in an effective amount for prevention of corneal fibrosis after trauma.

In some embodiments, the compounds of the disclosure are administered in an effective amount for prevention of corneal fibrosis after infection.

In some embodiments, the compounds of the disclosure are administered in an effective amount to treat non-alcoholic fatty liver disease (NAFLD).

In some embodiments, the compounds of the disclosure are administered in an effective amount for treatment and/or prevention of light chain deposition disease.

In some embodiments, the compounds of the disclosure are administered in an effective amount for treatment and/or prevention of IgA nephropathy.

In some embodiments, the compounds of the disclosure are administered in an effective amount for treatment and/or prevention of end stage renal disease.

In some embodiments, the compounds of the disclosure are administered in an effective amount for treatment and/or prevention of gout.

In some embodiments, the compounds of the disclosure are administered in an effective amount for treatment and/or prevention of pseudogout.

In some embodiments, the compounds of the disclosure are administered in an effective amount for treatment and/or prevention of diabetic nephrophathy.

In some embodiments, the compounds of the disclosure are administered in an effective amount for treatment and/or prevention of diabetic neuropathy.

In some embodiments, the compounds of the disclosure are administered in an effective amount for treatment and/or prevention of traumatic brain injury.

In some embodiments, the compounds of the disclosure are administered in an effective amount for treatment and/or prevention of noise-induced hearing loss.

In some embodiments, the compounds of the disclosure are administered in an effective amount for treatment and/or prevention of Alzheimer's Disease, In some embodiments, the compounds of the disclosure are administered in an effective amount for treatment and/or prevention of Parkinson's disease.

In some embodiments, the compounds of the disclosure are administered in an effective amount for treatment and/or prevention of Huntington Disease.

In some embodiments, the compounds of the disclosure are administered in an effective amount for treatment and/or prevention of amyotrophic lateral sclerosis.

In some embodiments, the compounds of the disclosure are administered in an effective amount for treatment and/or prevention of primary biliary cirrhosis.

In some embodiments, the compounds of the disclosure are administered in an effective amount for treatment and/or prevention of primary sclerosing cholangitis.

In some embodiments, the compounds of the disclosure are administered in an effective amount for treatment and/or prevention of uterine leiomyoma.

In some embodiments, the compounds of the disclosure are administered in an effective amount for treatment and/or prevention of sarcoidosis.

In some embodiments, the compounds of the disclosure are administered in an effective amount for treatment and/or prevention of chronic kidney disease.

Pharmaceutically Acceptable Compositions

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention are administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues. Subcutaneous depot formulations are also prepared with hyaluronidase.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention can also be administered topically, such as directly to the eye, e.g., as an eye-drop or ophthalmic ointment. Eye drops typically comprise an effective amount of at least one compound of the invention and a carrier capable of being safely applied to an eye. For example, the eye drops are in the form of an isotonic solution, and the pH of the solution is adjusted so that there is no irritation of the eye. In many instances, the epithelial barrier interferes with penetration of molecules into the eye. Thus, most currently used ophthalmic drugs are supplemented with some form of penetration enhancer. These penetration enhancers work by loosening the tight junctions of the most superior epithelial cells (Burstein, 1985, Trans Ophthalmol Soc U K 104(Pt 4): 402-9; Ashton et al., 1991, J Pharmacol Exp Ther 259(2): 719-24; Green et al., 1971, Am J Ophthalmol 72(5): 897-905). The most commonly used penetration enhancer is benzalkonium chloride (Tang et al., 1994, J Pharm Sci 83(1): 85-90; Burstein et al., 1980, Invest Ophthalmol Vis Sci 19(3): 308-13), which also works as preservative against microbial contamination. It is typically added to a final concentration of 0.01-0.05%.

The term "biological sample", as used herein, includes, without limitation, cell cultures or extracts thereof biopsied material obtained from a mammal or extracts thereof; and blood, saliva, urine, feces, semen, tears, or other body fluids or extracts thereof.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided compound, or composition thereof, is administered in combination with another therapeutic agent.

An additional therapeutic agent may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In some embodiments, the present invention provides a method of treating a disorder as described herein, comprising administering a provided compound or composition thereof, in combination with an additional therapeutic agent. In some embodiments, the additional therapeutic is standard of care for the disorder being treated.

As used herein the term "standard of care" refers to treatment that is accepted by medical experts as a proper treatment for a certain type of disease and that is widely used by healthcare professionals. Also known as best practice, standard medical care, and standard therapy. One of ordinary skill in the art would recognize the standard of care treatment protocol for treatment of the disorders described herein.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, anti-inflammatory agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like methotrexate (Rheumatrex®), "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), or "anti-IL-6" agents such as tocilizumab (Actemra®), diclofenac, cortisone, hyaluronic acid (Synvisc® or Hyalgan®).

In some embodiments, the present invention provides a method of treating allergic conjunctivitis in a patient in need thereof comprising administering to the patient a provided compound or composition thereof in combination with an additional therapeutic agent useful for treating allergy or at least one allergy-related symptom. In some embodiments, the additional therapeutic agent is an anti-histamine. In some embodiments, the anti-histamine is selected from fexofenadine (Allegra), terfenadine (Seldane), triprolidine (Zymine), brompheniramine (Lodrane), chlorpheniramine (Chlor-Trimeton), cetirizine, diphenhydramine, carbinoxamine, promethazine, loratedine (Claritin), desloratadine (Clarinex), cetirizine (Zyrtec), clemastine (Allerhist), levocetirizine (Xyzal), or hydroxyzine (Atarax).

In some embodiments, the additional therapeutic agent is an anti-allergy agent. Such anti-allergy agents are well known in the art and include anti-inflammatory nasal sprays, eye drops, nasal decongestants (e.g., oxymetazoline, phenylephrine, or pseudoephedrine), and immunotherapy (e.g., allergy shots). Such agents include mast cell inhibitors (e.g., cromolyn sodium) and leukotriene inhibitors (e.g., Singulair). In some embodiments, the additional therapeutic is cetirizine (e.g., Zerviate, a cetirizine ophthalmic solution).

In some embodiments, the second therapeutic agent is a leukotriene inhibitor, non-steroidal anti-inflammatory drug (NSAID), steroid, tyrosine kinase inhibitor, receptor kinase inhibitor, modulator of nuclear receptor family of transcription factor, HSP90 inhibitor, adenosine receptor (A2A) agonist, disease modifying antirheumatic drugs (DMARDS), phosphodiesterase (PDE) inhibitor, neutrophil elastase inhibitor, modulator of Axl kinase, or combinations thereof.

In some embodiments, the second therapeutic agent is a leukotriene inhibitor. In some embodiments, the leukotriene inhibitor is montelukast, zafirlukast, pranlukast, zileuton, or combinations thereof.

In some embodiments, the second therapeutic agent is an NSAID. In some embodiments, the NSAID is acetylsalicylic acid, diflunisal, salsalate, ibuprofen, dexibuprofen, naioxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, phenylbutazone, mefenamic acid, meclofenamic acid, flufenamic acid, tolfenamic acid, celecoxib or combinations thereof.

In some embodiments, the second therapeutic agent is a steroid. In some embodiments, the steroid is prednisone, prednisolone, methylprednisone, triacmcinolone, betamethasone, dexamethasone, and prodrugs thereof.

In some embodiments, the second therapeutic agent is a tyrosine kinase inhibitor. In some embodiments, the tyrosine kinase inhibitor is an inhibitor of the following kinases, including, among others, JAK, Syk, JNK/SAPK, MAPK, PI-3K, or Ripk2. In some embodiments, the tyrosine kinase inhibitor is ruxolitinib, tofacitinib, oclactinib, filgotinib, ganotinib, lestaurtinib, momelotinib, pacritinib, upadacitinib, peficitinib, fedratinib, bentamapimod, D-JNKI-1 (XG-102, AM-111), ponatinib, WEHI-345, OD36, GSK583, idelalisib, copanlisib, taselisib, duvelisib, alpelisib, umbralisib, dactolisib, CUDC-907, entospletinib, fostamatinib, or combinations thereof.

In some embodiments, the second therapeutic agent is a receptor kinase inhibitor, including among others, an inhibitor of EGFR or HER2. In some embodiments, the receptor kinase inhibitor is gefitinib, erlotinib, neratinib, lapatinib, cetuximab, panitumumab, vandetanib, necitumumab, osimertinib, trastuzumab, neratinib, lapatinib, pertuzumab, or combinations thereof.

In some embodiments, the second therapeutic agent is a modulator of nuclear receptor family of transcription factors, including, among others, and inhibitor of PPAR, RXR, FXR, or LXR. In some embodiments, the inhibitor is pioglitazone, bexarotene, obeticholic acid, ursodeoxycholic acid, fexaramine, hypocholamide, or combinations thereof.

In some embodiments, the second therapeutic agent is an Hsp90 inhibitor. In some embodiments, the Hsp90 inhibitor is ganetespib, 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010, or combinations thereof.

In some embodiments, the second therapeutic agent is an adenosine receptor (A2A) agonist. In some embodiments, the adenosine receptor agonist is, among others, disclosed in U.S. Pat. No. 9,067,963, which is incorporated herein by reference. In some embodiments, the adenosine receptor agonist is LNC-3050, LNC-3015, LNC-3047, LNC-3052, or combinations thereof.

In some embodiments, the second therapeutic agent is a disease modifying antirheumatic drugs (DMARDS). In some embodiments, the DMARDS is, among others, tocilizumab, certolizumab, etanercept, adalimumab, anakinra, abatacept, infliximab, rituximab, golimumab, uteskinumab, or combinations thereof.

In some embodiments, the second therapeutic agent is a phosphodiesterase (PDE) inhibitor. In some embodiments, the phosphodiesterase inhibitor is apremilast, crisaborole, piclimilast, drotaverine, ibudulast, roflumilast, sildenafil, tadalafil, vardenafil, or combinations thereof.

In some embodiments, the second therapeutic agent is a neutrophil elastase inhibitor. In some embodiments, the neutrophil elastase inhibitor is, among others, sivelestat.

In some embodiments, the second therapeutic agent is a modulator of Axl kinase. In some embodiments, the modulator of Axl kinase is bemcentinib (BGB324 or R428), TP-0903, LY2801653, amuvatinib (MP-470), bosutinib (SKI-606), MGCD 265, ASP2215, cabozantinib (XL184), foretinib (GSK1363089/XL880), or SGI-7079. In some embodiments, the modulator of Axl kinase is a monoclonal antibody targeting AXL (e.g., YW327.6S2) or an AXL decoy receptor (e.g., GL2I.T), or glesatinib, merestinib, or a dual Flt3-Axl inhibitor such as gilteritinib.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Procedures

X-ray powder diffraction patterns were collected on one of two instruments, either a Bruker AXS C2 GADDS diffractometer or a Bruker AXS D8 Advance diffractometer.

For X-ray powder diffraction patterns collected on a Bruker AXS C2 GADDS diffractometer, the following parameters were used. The X-ray powder diffraction patterns were collected with use of Cu Kα radiation (40 kV, 40 mA), automated XYZ stage, laser video microscope for auto-sample positioning and a HiStar 2-dimensional area detector. X-ray optics included a single Gobel multilayer mirror coupled with a pinhole collimator of 0.3 mm. The instrument is performance checked using a certified Corundum standard (NIST 1976). The beam divergence (e.g., the effective size of the X-ray beam on the sample) was approximately 4 mm. A θ-θ continuous scan mode was employed with a sample—detector distance of 20 cm which gives an effective 2θ range of 3.2°-29.7°. Typically, the sample would be exposed to the X-ray beam for 120 seconds. The software used for data collection was GADDS for XP/2000 4.1.43 and the data were analysed and presented using Diffrac Plus EVA v15.0.0.0.

Ambient Conditions: Samples run under ambient conditions were prepared as flat plate specimens using powder as received without grinding. Approximately 1-2 mg of the sample was lightly pressed on a glass slide to obtain a flat surface. Non-Ambient Conditions: Samples run under non-ambient conditions were mounted on a silicon wafer with heat-conducting compound. The sample was then heated to the appropriate temperature at 20° C./min and subsequently held isothermally for 1 minute before data collection was initiated.

For X-ray powder diffraction patterns collected on a Bruker AXS D8 Advance diffractometer, the following parameters were used. X-Ray Powder Diffraction patterns were collected using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v15.0.0.0. Samples were run under ambient conditions as flat plate specimens using powder as received. The sample was gently packed into a cavity cut into polished, zero-background (510) silicon wafer. The sample was rotated in its own plane during analysis. The details of the data collection are: A) an angular range: 2 to 42° 2θ; B) a step size: 0.05° 2θ; and C) a collection time: 0.5 s/step.

Proton Nuclear Magnetic Resonance (1H NMR) spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone. Samples were prepared in DMSO-$d_6$, unless otherwise stated. Off-line analysis was carried out using ACD Spectrus Processor 2014.

Differential scanning calorimetry (DSC) data were collected on a TA Instruments Q2000 equipped with a 50-position auto-sampler. The calibration for thermal capacity was carried out using sapphire and the calibration for energy and temperature was carried out using certified indium. Typically, 0.5-3 mg of each sample, in a pin-holed aluminium pan, was heated at 10° C./min from 25° C. to 300° C. A purge of dry nitrogen at 50 ml/min was maintained over the sample. Modulated temperature DSC was carried out using an underlying heating rate of 2° C./min and temperature modulation parameters of ±0.318° C. (amplitude) every 60 seconds (period). The instrument control software was Advantage for Q Series v2.8.0.394 and Thermal Advantage v5.5.3 and the data were analysed using Universal Analysis v4.5A.

Thermo-gravimetric analysis (TGA) data were collected on a TA Instruments Q500 TGA, equipped with a 16-position auto-sampler. The instrument was temperature calibrated using certified Alumel and Nickel. Typically, 5-10 mg of each sample was loaded onto a pre-tared aluminium DSC pan and heated at 10° C./min from ambient temperature to 350° C. A nitrogen purge at 60 ml/min was maintained over the sample. The instrument control software was Advantage for Q Series v2.5.0.256 and Thermal Advantage v5.5.3 and the data were analysed using Universal Analysis v4.5A.

Example A

General Preparation of Compound A

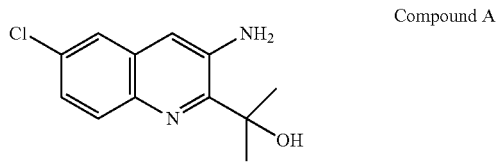 [SMILES: CC(C)(O)c1nc2ccc(Cl)cc2cc1N]

Compound A

The title compound was prepared according to the steps and intermediates (e.g., Scheme 1) described below and in the '500 publication, the entirety of which is incorporated herein by reference.

Scheme 1. Synthesis of Compound A

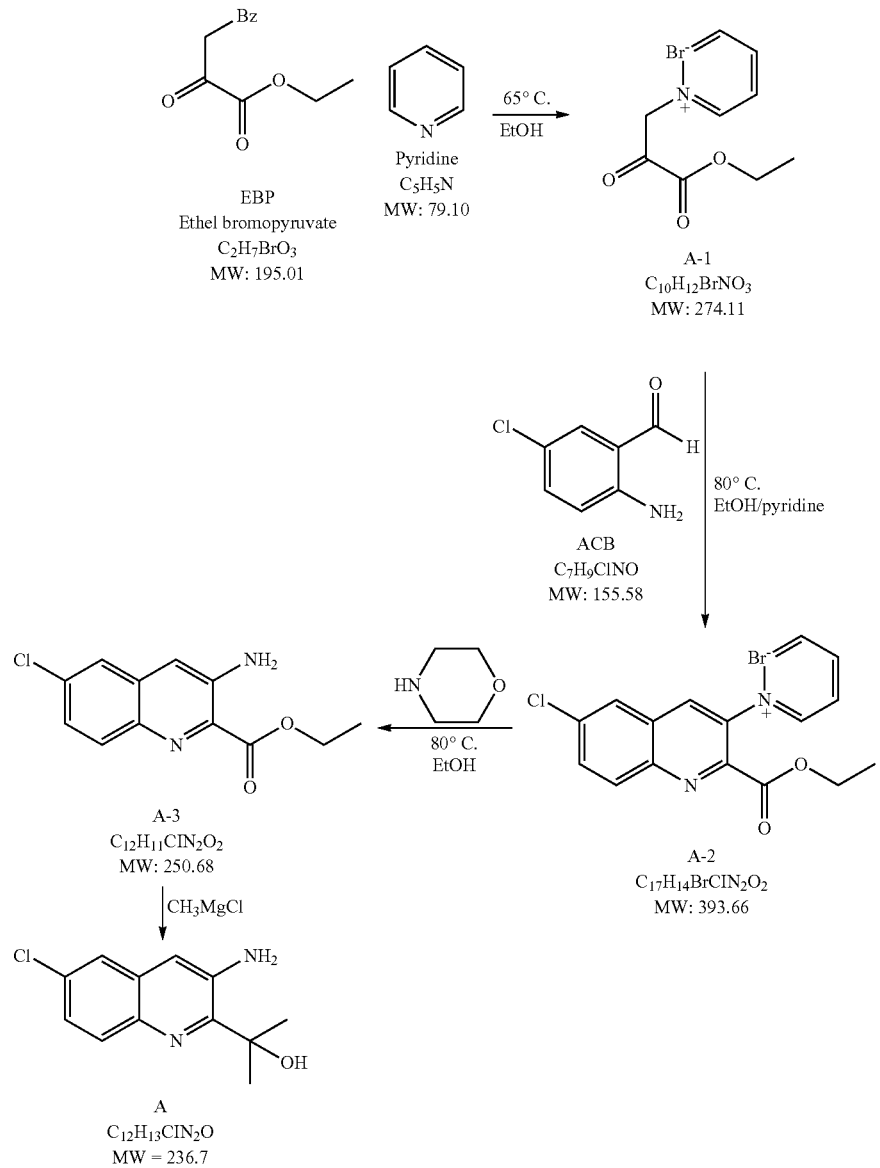

Step 1: Synthesis of Intermediate A-1

To a 2 L round bottom flask was charged ethanol (220 mL), and pyridine (31 g, 392 mmol) and the resulting solution stirred at a moderate rate of agitation under nitrogen. To this solution was added ethyl bromopyruvate (76.6 g, 354 mmol) in a slow, steady stream. The reaction mixture was allowed to stir at 65±5° C. for 2 hours.

Step 2: Synthesis of Intermediate A-2

Upon completion of the 2-hour stir time in example 1, the reaction mixture was slowly cooled to 18-22° C. The flask was vacuum-purged three times at which time 2-amino-5-chlorobenzaldehyde (ACB) (50.0 g, 321 mmol) was added directly to the reaction flask as a solid using a long plastic funnel. Pyridine (64.0 g, 809 mmol) was added followed by an EtOH rinse (10 mL) and the reaction mixture was heated at 80±3° C. under nitrogen for about 16 hours (overnight) at which time HPLC analysis indicated that the reaction was effectively complete.

Step 3: Synthesis of Intermediate A-3

The reaction mixture from example 2 was cooled to about 70° C. and morpholine (76.0 g, 873 mmol)) was added to the 2 L reaction flask using an addition funnel. The reaction mixture was heated at 80±2° C. for about 2.5 hours at which time the reaction was considered complete by HPLC analysis (area % of A-3 stops increasing). The reaction mixture was cooled to 10-15° C. for the quench, work up, and isolation.

Step 4: Isolation of Intermediate A-3

To the 2 L reaction flask was charged water (600 g) using the addition funnel over 30-60 minutes, keeping the temperature below 15° C. by adjusting the rate of addition and using a cooling bath. The reaction mixture was stirred for an additional 45 minutes at 10-15° C. then the crude A-3 isolated by filtration using a Buchner funnel. The cake was washed with water (100 mL×4) each time allowing the water to percolate through the cake before applying a vacuum. The cake was air dried to provide crude A-3 as a nearly dry brown solid. The cake was returned to the 2 L reaction flask and heptane (350 mL) and EtOH (170 mL) were added and the mixture heated to 70±3° C. for 30-60 minutes. The slurry was cooled to 0-5° C. and isolated by filtration under vacuum. The A-3 was dried in a vacuum drying oven under vacuum and 35±3° C. overnight (16-18 hours) to provide A-3 as a dark green solid.

Step 5: Synthesis of Compound A

To a 2 L round bottom flask was charged methylmagnesium chloride (200 mL of 3.0 M solution in THF, 600 mmol). The solution was cooled to 0-5° C. using an ice bath.

A 500 mL flask (magnetic stirring) was charged with 22.8 grams A-3 from example 4 and THF (365 mL), stirred to dissolve then transferred to an addition funnel on the 2 L Reaction Flask. The A-3 solution was added drop-wise to the reaction flask over 5.75 hours, keeping the temperature of the reaction flask between 0-5° C. throughout the addition. At the end of the addition the contents of the flask were stirred for an additional 15 minutes at 0-5° C. then the cooling bath was removed and the reaction was allowed to stir overnight at ambient temperature.

The flask was cooled in an ice bath and the reaction mixture was carefully quenched by adding EtOH (39.5 g, 857 mmol) drop-wise to the reaction mixture, keeping the temperature of the reaction mixture below 15° C. during the course of the addition. An aqueous solution of NH4Cl (84.7 g NH4Cl in 415 mL water) was then carefully added and the mixture stirred under moderate agitation for about 30 minutes then transferred to a separatory funnel to allow the layers to separate. Solids were present in the aqueous phase so HOAc (12.5 g) was added and the contents swirled gently to obtain a nearly homogeneous lower aqueous phase. The lower aqueous layer was transferred back to the 2 L reaction flask and stirred under moderate agitation with 2-methyl-THF (50 mL) for about 15 minutes. The original upper organic layer was reduced in volume to approximately 40 mL using a rotary evaporator at ≤40° C. and vacuum as needed. The phases in the separatory funnel were separated and the upper 2-MeTHF phase combined with the product residue, transferred to a 500 mL flask and vacuum distilled to an approximate volume of 25 mL. To this residue was added 2-MeTHF (50 mL) and distilled to an approximate volume of 50 mL. The crude compound A solution was diluted with 2-MeTHF (125 mL), cooled to 5-10° C. and 2M H2SO4 (aq) (250 mL) was slowly added and the mixture stirred for 30 minutes as the temperature was allowed to return to ambient. Heptane (40 mL) was charged and the reaction mixture stirred for an additional 15 minutes then transferred to a separatory funnel and the layers were allowed to separate. The lower aqueous product layer was extracted with additional heptane (35 mL) then the lower aqueous phase was transferred to a 1 L reaction flask equipped with a mechanical stirrer and the mixture was cooled to 5-10° C. The combined organic layers were discarded. A solution of 25% NaOH(aq) was prepared (NaOH, 47 g, water, 200 mL) and slowly added to the 1 L reaction flask to bring the pH to a range of 6.5-8.5.

EtOAc (250 mL) was added and the mixture was stirred overnight. The mixture was transferred to a separatory funnel and the lower phase discarded. The upper organic layer was washed with brine (25 mL) then the upper organic product layer was reduced in volume on a rotary evaporator to obtain the crude compound A as a dark oil that solidified within a few minutes. The crude compound A was dissolved in EtOAc (20 mL) and filtered through a plug of silica gel (23 g) eluting with 3/1 heptane/EtOAc until all compound A was eluted (approximately 420 mL required) to remove most of the dark color of compound A. The solvent was removed in vacuo to provide 14.7 g of compound A as a tan solid. Compound A was taken up in EtOAc (25 mL) and eluted through a column of silica gel (72 g) using a mobile phase gradient of 7/1 heptane/EtOAc to 3/1heptane/EtOAc (1400 mL total). The solvent fractions containing compound A were stripped, compound A diluted with EtOAc (120 mL) and stirred in a flask with Darco G-60 decolorizing carbon (4.0 g) for about 1 hour. The mixture was filtered through celite using a fitted funnel, rinsing the cake with EtOAc (3×15 mL). The combined filtrates were stripped on a rotary evaporator and compound A dissolved in heptane (160 mL)/EtOAc(16 mL) at 76° C. The homogeneous solution was slowly cooled to 0-5° C., held for 2 hours then compound A was isolated by filtration. After drying in a vacuum oven for 5 hours at 35° C. under best vacuum, compound A was obtained as a white solid. HPLC purity: 100% (AUC).

Example 1

Preparation of Free Base Forms A and B of Compound A

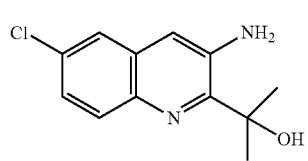

Compound A

Compound A is prepared according to the method described in detail in Examples 1-5 of the '500 publication, the entirety of which is hereby incorporated herein by reference.

Form A of Compound A

Form A of compound A was prepared as follows.

Compound A was dissolved in dichloromethane (DCM, 15 ml). The clear solution was treated with heptane (130 ml) at ambient conditions. The solid obtained was filtered and air dried.

Characterization of the resulting material demonstrated a non-solvated, non-hygroscopic crystalline Form A.

Table 1, supra, is reproduced below and sets forth the X-ray diffraction peaks observed for Form A of compound A.

TABLE 1

XRPD Peak Positions for Form A of Compound A

| Position (°2θ) | Intensity % |
|---|---|
| 5.4 | 17.0 |
| 10.8 | 29.0 |
| 13.3 | 6.9 |
| 14.0 | 11.7 |
| 14.7 | 1.7 |
| 16.6 | 100.0 |
| 17.8 | 2.2 |
| 20.1 | 2.0 |
| 20.3 | 5.0 |
| 21.5 | 2.5 |
| 24.6 | 4.7 |
| 26.2 | 9.6 |
| 26.9 | 6.6 |
| 29.5 | 10.4 |

[1] In this and all subsequent tables, the position 2θ is within ±0.2.

FIG. 1 depicts an XRPD pattern of Form A of compound A.

Figure 2:
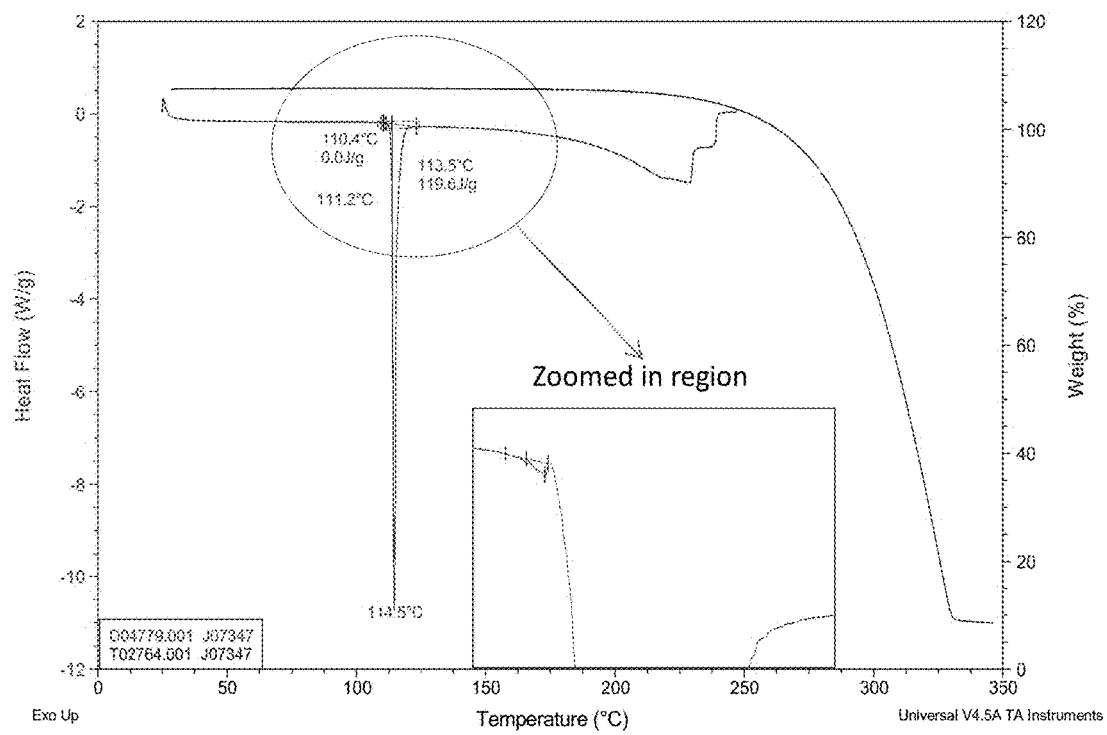
FIG. 2 depicts a DSC thermogram and TGA trace of Compound A, Form A.

FIG. 2 depicts a DSC thermogram and TGA trace of Form A of compound A.

Form B of Compound A

Form B of compound A was prepared as follows.

Form A (obtained as described immediately above) was treated with a premixed solution of isopropyl alcohol:cyclohexane (700 µl:7 ml) at ambient conditions. The sample was heated to and stirred at 75° C. for 5 minutes. The solution was then cooled to 5° C. at a rate of 0.3° C. per minute. After stirring at 5° C. for ca. 12 hours, an aliquot was analysed by XRPD. Form A was obtained. Seeds of Form B (AB-1324-09-29) were added to the sample. The sample was stirred at 5° C. for 4 days and analysed by XRPD after filtration.

Characterization of the resulting material demonstrated a non-solvated, slightly hygroscopic crystalline Form B.

Table 2, supra, is reproduced below and sets forth the X-ray diffraction peaks observed for Form B of compound A.

TABLE 2

XRPD Peak Positions for Form B of Compound A

| Position (°2θ) | Intensity % |
|---|---|
| 11.6 | 100.0 |
| 14.5 | 11.2 |
| 16.1 | 7.2 |
| 19.0 | 20.2 |
| 23.0 | 2.0 |
| 23.3 | 42.8 |
| 24.5 | 6.3 |
| 24.7 | 2.5 |
| 24.9 | 2.4 |
| 27.2 | 2.2 |
| 28.6 | 2.8 |
| 31.6 | 3.8 |
| 31.8 | 2.2 |
| 35.3 | 34.3 |

[1] In this and all subsequent tables, the position 2θ is within ±0.2.

FIG. 3 depicts an XRPD pattern of Form B of compound A.

Figure 4:
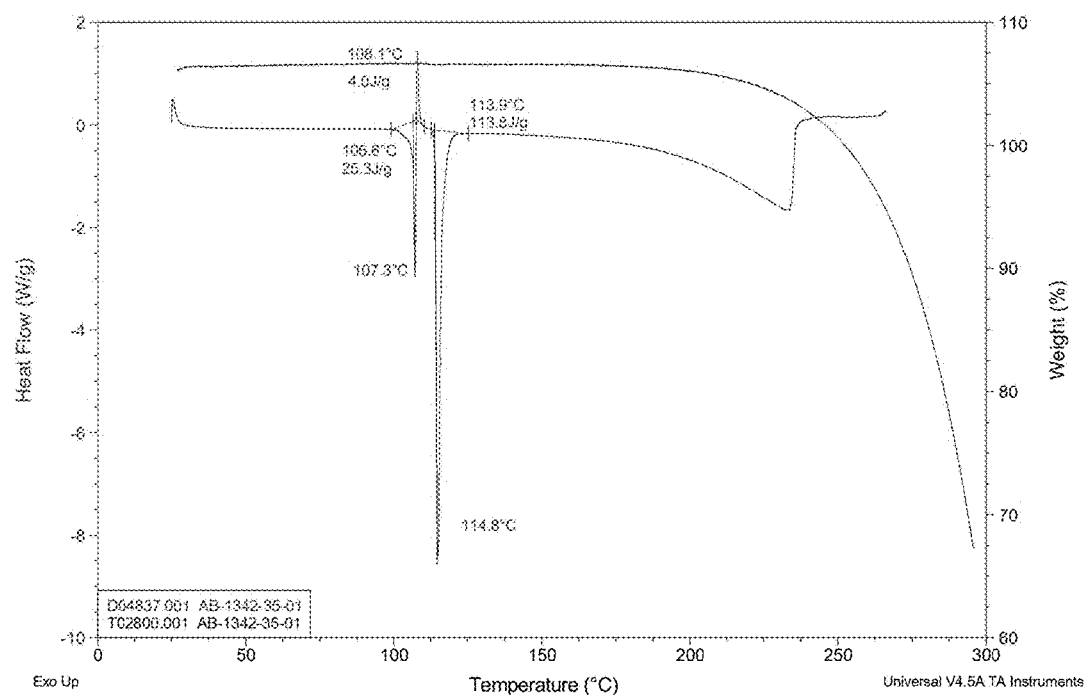
FIG. 4 depicts a DSC thermogram and TGA trace of Compound A, Form B.

FIG. 4 depicts a DSC thermogram and TGA trace of Form B of compound A.

Free Base Competitive Slurries:

This set of experiments was performed using various solvents and solvent combinations. Cross-seeding experiments were performed over a range of temperatures to help define the relationship between Forms A and B.

Procedure: Twenty-one cross-seeding experiments were performed by adding equal amounts of Forms A and B (weight/weight, total of 25 mg). The mixture was slurried in the given solvent/system (ca. 5 vol. 125 µl) at room temperature, then matured at a specific temperature (5° C., 25° C. or 50° C.) for 72 h. The solids were filtered, air dried and analysed by XRPD. After two days, samples 3 and 15 were completely dry and additional portions of their corresponding solvents were added, (250 µl was added to sample 3 and 248.6 µl was added to sample 15). Solids obtained were characterised by XRPD. The results are shown below in Table 14.

TABLE 14

Summary of results obtained from competitive slurries for Forms A and B of Compound A

| Sample | Solvent | Vol (µl) | Temperature | XRPD |
|---|---|---|---|---|
| 1 | Heptane | 125 | 5 | Form B |
| 2 | Heptane | 125 | 25 | Form B |
| 3 | Heptane | 125* | 50 | Form B |
| 4 | EtOAc:Heptane | 124.3 | 5 | Form B |
| 5 | EtOAc:Heptane | 124.3 | 25 | Form B |
| 6 | EtOAc:Heptane | 124.3 | 50 | Form B |
| 7 | Acetone:H₂O (10%) | 124.3 | 5 | Form B |
| 8 | Acetone:H₂O (10%) | 124.3 | 25 | Form B |
| 9 | Acetone:H₂O (10%) | 124.3 | 50 | Forms A & B |
| 10 | Toluene | 125 | 5 | Form B |
| 11 | Toluene | 125 | 25 | Form B |
| 12 | Toluene | 125 | 50 | Form A |
| 13 | Toluene:Heptane | 124.3 | 5 | Form B |
| 14 | Toluene:Heptane | 124.3 | 25 | Form B |
| 15 | Toluene:Heptane | 124.3* | 50 | Form B |
| 16 | Cyclohexane | 125 | 5 | Forms A & B |
| 17 | Cyclohexane | 125 | 25 | Form B |
| 18 | Cyclohexane | 125 | 50 | Form B |
| 19 | Toluene:Cyclohexane | 124.3 | 5 | Form B |
| 20 | Toluene:Cyclohexane | 124.3 | 25 | Form B |
| 21 | Toluene:Cyclohexane | 124.3 | 50 | Form B |

*Samples were dry. Additional solvent was added

The competitive slurries of the two anhydrous forms (Form A & Form B) showed Form B was the most stable form under the investigated conditions. Nonetheless, Form A is stable once isolated. The predominance of a particular form is solvent and temperature dependent. The transition temperature between Form A and Form B is below 50° C., which means in order to isolate a particular form a specific method has to be developed and followed.

At 5° C., the majority of the samples had converted to Form B. The sample from cyclohexane remained a mixture of Form A and Form B. At 25° C., all of the samples had converted to Form B. At 50° C., the majority of the samples had converted to Form B. The sample from acetone: water 10% experiment remained a mixture of Form A and Form B. The sample from toluene had converted to Form A. One aspect to consider is that the samples were analysed after 3 days incubation at specific temperatures. Prolonged incubation seemed to favour the formation of Form B, suggesting that the formation of Form B is driven by a kinetic factor, which in turn means hold time is an important parameter to consider during the crystallisation development. A monotropic or enantiotropic relationship between the two forms could not be established. If either pure Form A or pure Form B is isolated from the experiment, the form will remain stable and will not convert to the other. However, if Form A is left in solvent media for a long incubation period, it will convert to Form B.

Example 2

Preparation of Forms A and B of Compound 1

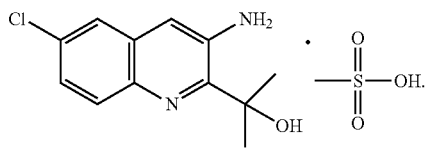

Form A of Compound 1

Form A of compound 1 was prepared as follows.

Compound A was dissolved in EtOH (10 vol, 500 µl) at ambient conditions. The solution was heated to 50° C., then treated with methanesulfonic acid (1.0 mol eq. added as a stock solution in THF, 1M). A cooling ramp was applied from 50° C. to 5° C. at 0.1° C./min. After 20 hours, the solution was treated with antisolvent (TBME, 4 ml) at ambient conditions. If no solid was obtained post cooling, then antisolvent solutions were filtered, air dried and the attained solid was further analyzed by the appropriate techniques.

Characterization of the resulting material demonstrated a non-hydrated, crystalline Form A.

Table 3, supra, is reproduced below and sets forth the X-ray diffraction peaks observed for Form A of compound 1.

TABLE 3

| XRPD Peak Positions for Form A of Compound 1 | |
| --- | --- |
| Position (°2θ) | Intensity % |
| 9.3 | 100.0 |
| 10.1 | 2.7 |
| 12.9 | 4.9 |
| 14.0 | 2.6 |
| 15.6 | 6.4 |
| 16.5 | 10.1 |
| 16.9 | 10.9 |
| 17.4 | 3.2 |
| 18.5 | 2.9 |

TABLE 3-continued

| XRPD Peak Positions for Form A of Compound 1 | |
| --- | --- |
| Position (°2θ) | Intensity % |
| 18.7 | 6.2 |
| 19.1 | 6.9 |
| 20.5 | 7.9 |
| 21.0 | 6.4 |
| 21.6 | 8.2 |
| 22.4 | 2.6 |
| 22.7 | 1.7 |
| 23.1 | 7.4 |
| 23.4 | 2.6 |
| 24.0 | 3.9 |
| 24.9 | 6.9 |
| 25.8 | 2.3 |
| 26.4 | 14.6 |
| 26.7 | 1.8 |
| 27.2 | 4.6 |
| 27.8 | 4.1 |
| 28.4 | 2.2 |
| 29.5 | 3.8 |
| 29.8 | 6.7 |

[1] In this and all subsequent tables, the position 2θ is within ±0.2.

FIG. 5 depicts an XRPD pattern of Form A of compound 1.

Figure 6:
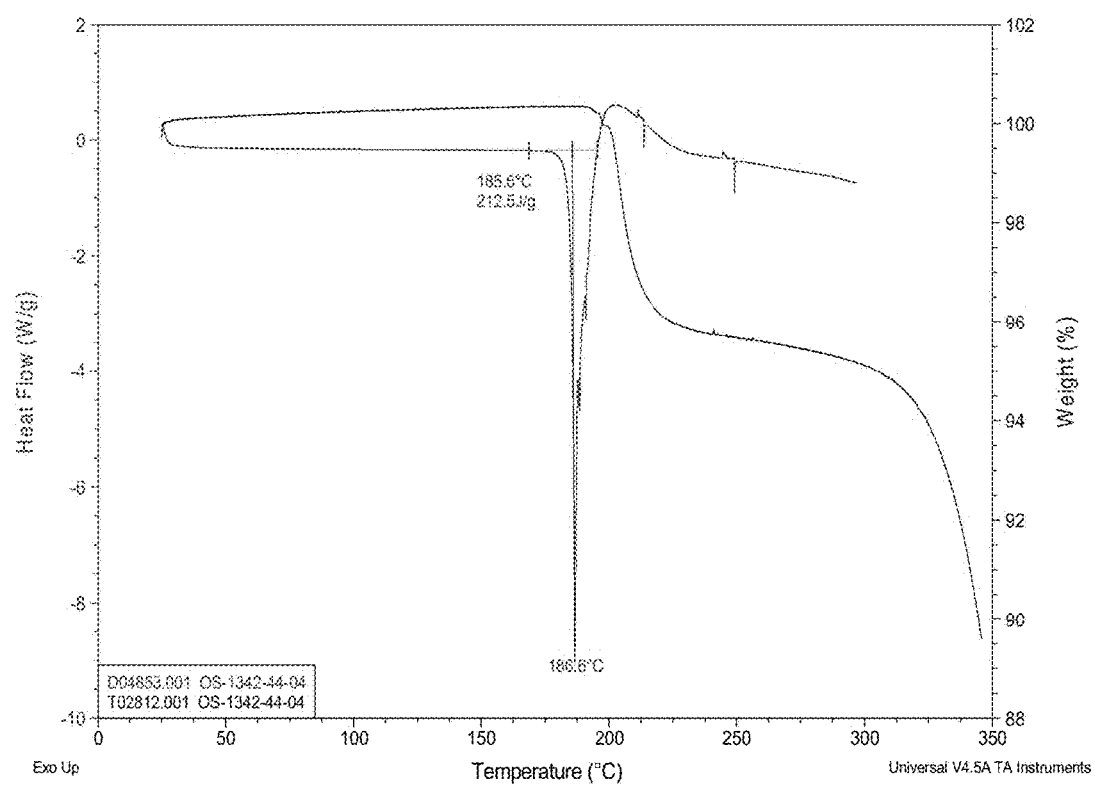
FIG. 6 depicts a DSC thermogram and TGA trace of Compound 1, Form A.

FIG. 6 depicts a DSC thermogram and TGA trace of Form A of compound 1.

Form B of Compound 1

Form B of compound 1 was prepared as follows.

Compound A was dissolved in EtOH (10 vol, 500 µl) at ambient conditions. The solution was treated with methanesulfonic acid (1.0 mol eq. added as a stock solution in THF, 1M) at ambient conditions. A cooling ramp was applied from 50° C. to 5° C. at 0.1° C./min. After 20 hours, solids obtained were filtered, air dried and analysed by XRPD. The solutions were treated with antisolvent (TBME, 4 ml) at ambient conditions. After 48 h stirring at ambient conditions the obtained solid was filtered, air dried and analysed by the appropriate techniques.

Characterization of the resulting material demonstrated a possible hydrated form, slightly hygroscopic crystalline Form B.

Table 4, supra, is reproduced below and sets forth the X-ray diffraction peaks observed for Form B of compound 1.

TABLE 4

| XRPD Peak Positions for Form B of Compound 1 | |
| --- | --- |
| Position (°2θ) | Intensity % |
| 6.9 | 1.3 |
| 9.6 | 100.0 |
| 11.8 | 9.9 |
| 13.5 | 3.5 |
| 16.4 | 3.9 |
| 16.9 | 4.3 |
| 19.1 | 18.2 |
| 19.4 | 14.8 |
| 20.3 | 6.2 |
| 20.9 | 5.1 |
| 21.8 | 3.2 |
| 23.7 | 10.3 |
| 26.2 | 11.7 |
| 28.8 | 18.2 |

[1] In this and all subsequent tables, the position 2θ is within ±0.2.

FIG. 7 depicts an XRPD pattern of Form B of compound 1.

Figure 8:
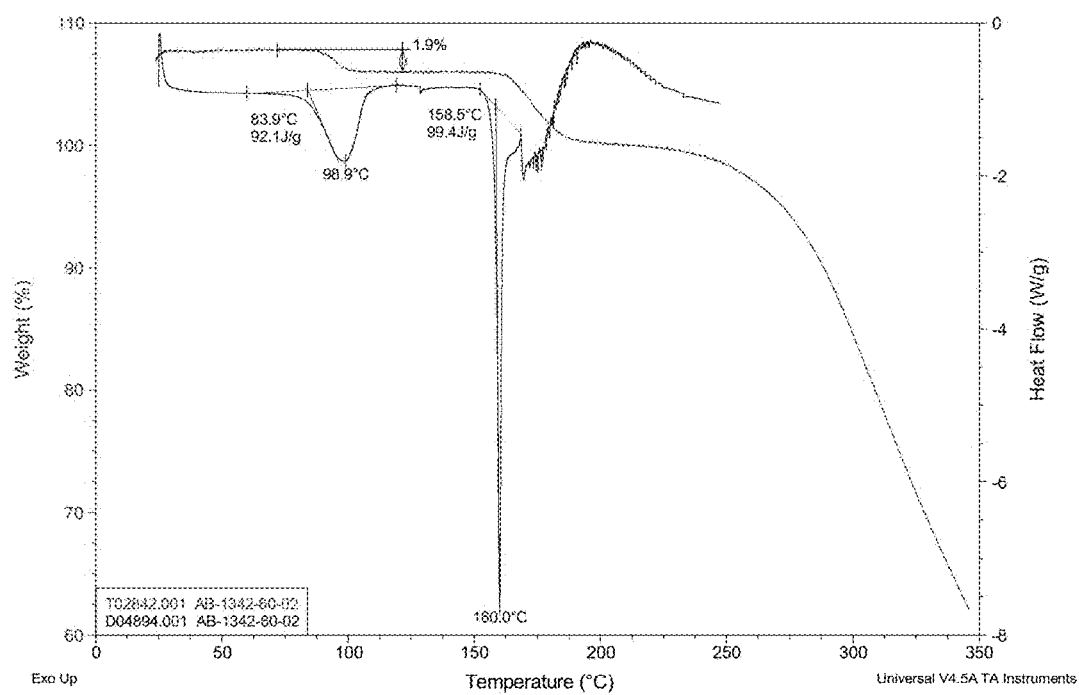
FIG. 8 depicts a DSC thermogram and TGA trace of Compound 1, Form B.

FIG. 8 depicts a DSC thermogram and TGA trace of Form B of compound 1.

Example 3

Preparation of Forms A and B of Compound 2

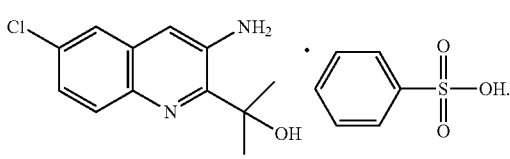

2

Form A of Compound 2

Form A of compound 2 was prepared as follows.

Compound A was dissolved in EtOH (10 vol, 500 μl) at ambient conditions. The solution was heated to 50° C., then treated with benzenesulfonic acid (1.0 mol eq. added as a stock solution in THF, 1M). A cooling ramp was applied from 50° C. to 5° C. at 0.1° C./min. After 20 hours, the solution was treated with antisolvent (TBME, 4 ml) at ambient conditions. If no solid was obtained post cooling, then antisolvent solutions were filtered, air dried and the attained solid was further analyzed by the appropriate techniques.

Characterization of the resulting material demonstrated a non-hydrated, slightly hygroscopic Form A.

Table 5, supra, is reproduced below and sets forth the X-ray diffraction peaks observed for Form A of compound 2.

TABLE 5

XRPD Peak Positions for Form A of Compound 2

| Position (°2θ) | Intensity % |
|---|---|
| 6.3 | 4.4 |
| 6.8 | 7.4 |
| 8.4 | 100.0 |
| 10.1 | 5.0 |
| 11.0 | 3.3 |
| 13.3 | 13.5 |
| 14.0 | 14.3 |
| 16.3 | 7.4 |
| 16.9 | 8.6 |
| 17.5 | 4.1 |
| 18.7 | 7.4 |
| 20.1 | 10.2 |
| 20.5 | 5.2 |
| 21.1 | 5.2 |
| 21.3 | 8.0 |
| 24.8 | 6.9 |
| 25.4 | 18.6 |
| 26.0 | 11.9 |

[1] In this and all subsequent tables, the position 2θ is within ±0.2.

FIG. 9 depicts an XRPD pattern of Form A of compound 2.

Figure 10:
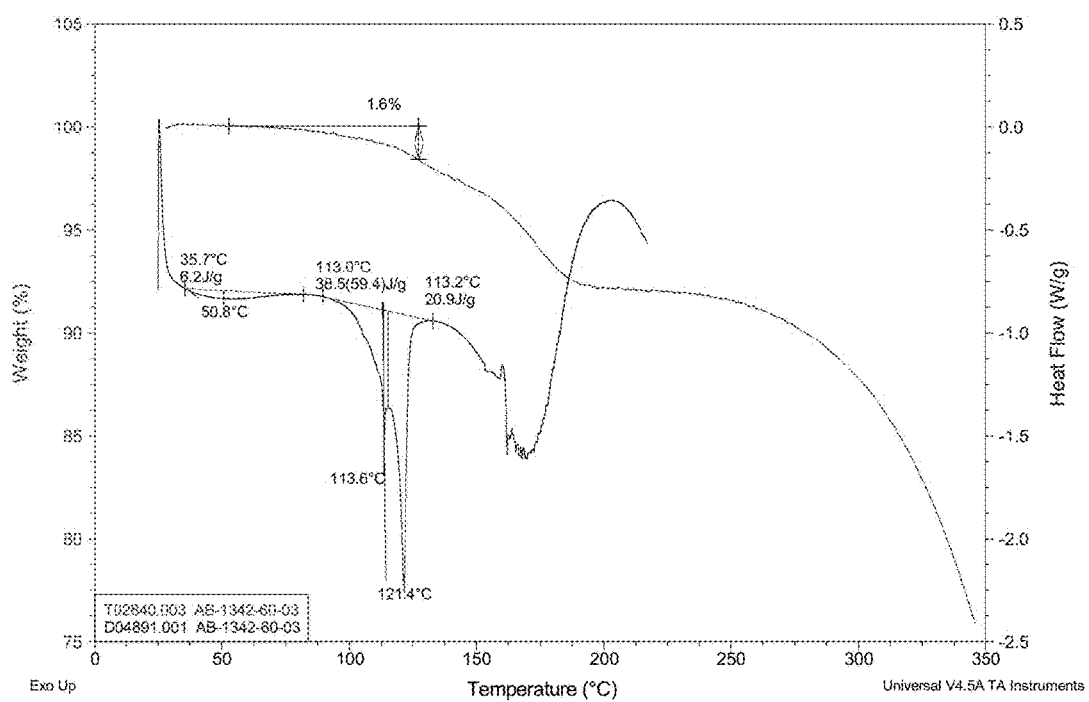
FIG. 10 depicts a DSC thermogram and TGA trace of Compound 2, Form A.

FIG. 10 depicts a DSC thermogram and TGA trace of Form A of compound 2.

Form B of Compound 2

Form B of compound 2 was prepared as follows.

Compound A was dissolved in EtOH (10 vol, 500 μl) at ambient conditions. The solutions were heated to 50° C., then treated with benzenesulfonic acid (1.0 mol eq. added as a stock solution in THF, 1M). A cooling ramp was applied from 50° C. to 5° C. at 0.1° C./min. After 20 hours, the solution was treated with antisolvent (TBME, 4 ml) at ambient conditions. If no solid was obtained post cooling, then antisolvent solutions were filtered, air dried and the attained solid was further analyzed by the appropriate techniques. Then an aliquot of the recovered solid was stored at 40° C./75% RH for one week and analysed XRPD.

Only XRPD analysis was performed on this material.

Table 6, supra, is reproduced below and sets forth the X-ray diffraction peaks observed for Form B of compound 2.

TABLE 6

XRPD Peak Positions for Form B of Compound 2

| Position (°2θ) | Intensity % |
|---|---|
| 5.8 | 19.3 |
| 6.0 | 12.3 |
| 7.1 | 17.3 |
| 8.4 | 51.2 |
| 13.1 | 16.3 |
| 13.9 | 20.6 |
| 14.5 | 46.8 |
| 16.9 | 21.9 |
| 18.2 | 29.0 |
| 20.1 | 46.2 |
| 24.1 | 42.2 |
| 24.9 | 49.0 |
| 25.8 | 34.7 |
| 26.8 | 100.0 |
| 29.3 | 54.7 |

[1] In this and all subsequent tables, the position 2θ is within ±0.2.

FIG. 11 depicts an XRPD pattern of Form B of compound 2.

Example 4

Preparation of Form A of Compound 3

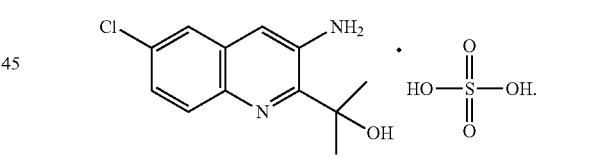

3

Form A of Compound 3

Form A of compound 3 was prepared as follows.

Compound A was dissolved in EtOH (10 vol, 500 μl) at ambient conditions. The solution was heated to 50° C., then treated with sulfuric acid (1.0 mol eq. added as a stock solution in THF, 1M). A cooling ramp was applied from 50° C. to 5° C. at 0.1° C./min. After 20 hours, the solution was treated with antisolvent (TBME, 4 ml) at ambient conditions. If no solid was obtained post cooling, then antisolvent solutions were filtered, air dried and the attained solid was further analyzed by the appropriate techniques.

Characterization of the resulting material demonstrated a non-hydrated, slightly hygroscopic Form A.

Table 7, supra, is reproduced below and sets forth the X-ray diffraction peaks observed for Form A of compound 3.

TABLE 7

XRPD Peak Positions for Form A of Compound 3

| Position (°2θ) | Intensity % |
|---|---|
| 10.0 | 23.9 |
| 12.5 | 7.6 |
| 12.7 | 17.9 |
| 14.8 | 5.2 |
| 17.2 | 46.5 |
| 18.5 | 9.3 |
| 19.1 | 23.5 |
| 20.0 | 5.8 |
| 20.4 | 4.2 |
| 20.8 | 9.0 |
| 22.0 | 11.5 |
| 22.8 | 25.8 |
| 23.4 | 7.0 |
| 23.8 | 37.9 |
| 24.9 | 9.0 |
| 25.5 | 100.0 |
| 25.7 | 14.9 |
| 27.3 | 10.4 |
| 27.7 | 12.2 |

[1] In this and all subsequent tables, the position 2θ is within ±0.2.

FIG. 12 depicts an XRPD pattern of Form A of compound 3.

Figure 13:
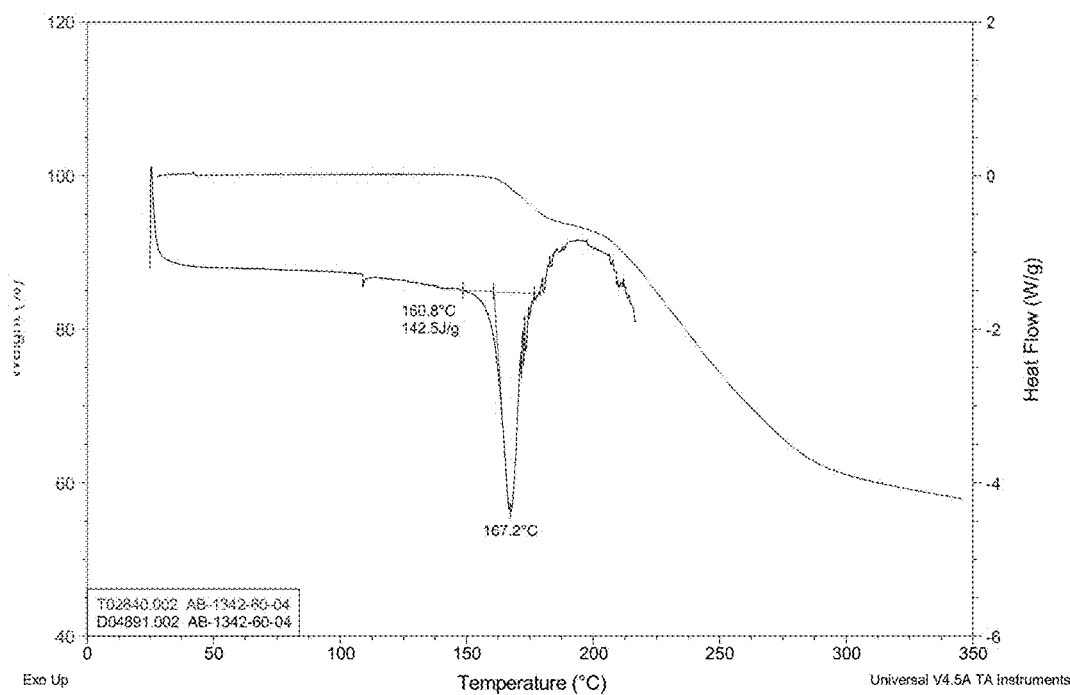
FIG. 13 depicts a DSC thermogram and TGA trace of Compound 3, Form A.

FIG. 13 depicts a DSC thermogram and TGA trace of Form A of compound 3.

TABLE 8

XRPD Peak Positions for Form A of Compound 4

| Position (°2θ) | Intensity % |
|---|---|
| 8.2 | 8.3 |
| 11.1 | 6.0 |
| 13.4 | 60.5 |
| 14.2 | 9.9 |
| 15.3 | 16.1 |
| 16.5 | 18.2 |
| 17.0 | 73.8 |
| 17.7 | 18.6 |
| 18.0 | 20.7 |
| 18.6 | 6.7 |
| 20.7 | 51.7 |
| 21.5 | 9.9 |
| 22.0 | 29.9 |
| 22.1 | 6.9 |
| 22.4 | 42.5 |
| 23.2 | 22.1 |
| 24.5 | 6.7 |
| 25.3 | 12.6 |
| 25.9 | 100.0 |
| 26.5 | 33.3 |
| 27.0 | 9.9 |
| 27.3 | 29.0 |
| 29.3 | 32.4 |

[1] In this and all subsequent tables, the position 2θ is within ±0.2.

FIG. 14 depicts an XRPD pattern of Form A of compound 4.

Figure 15:
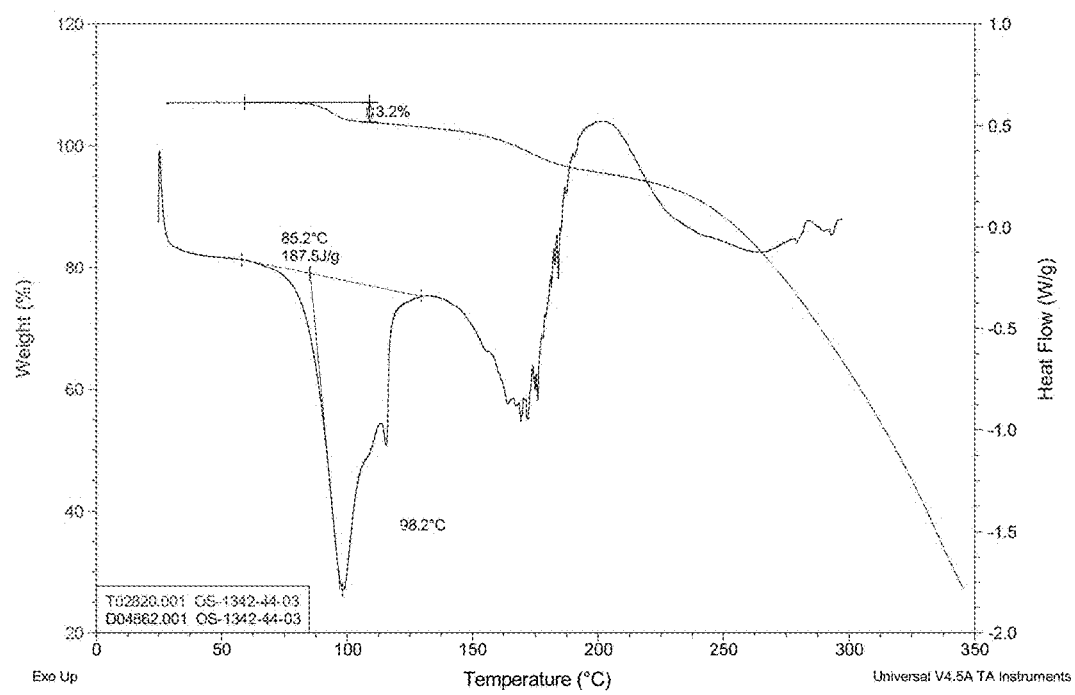
FIG. 15 depicts a DSC thermogram and TGA trace of Compound 4, Form A.

FIG. 15 depicts a DSC thermogram and TGA trace of Form A of compound 4.

Example 5

Preparation of Form A of Compound 4

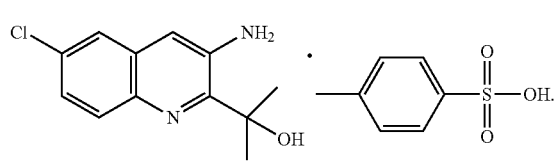

4

Form A of Compound 4

Form A of compound 4 was prepared as follows.

Compound A was dissolved in EtOH (10 vol, 500 µl) at ambient conditions. The solution was heated to 50° C., then treated with toluenesulfonic acid (1.0 mol eq. added as a stock solution in THF, 1M). A cooling ramp was applied from 50° C. to 5° C. at 0.1° C./min. After 20 hours, no solid was obtained and then the solution was further cooled at −20° C. for 48 h. No solid was obtained and the solution was allowed to evaporate at ambient condition and as a result a gum was obtained. The gum was treated with 500 µl of heptane and placed for maturation (50° C./RT) for 24 h. A solid was obtained from the experiment, and then it was filtered, air dried and analysed by the appropriate techniques.

Characterization of the resulting material demonstrated a crystalline, and a possible hydrated form.

Table 8, supra, is reproduced below and sets forth the X-ray diffraction peaks observed for Form A of compound 4.

Example 6

Preparation of Form A of Compound 5

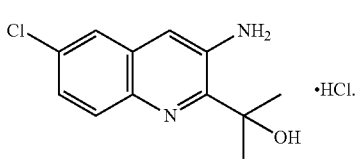

5

Form A of Compound 5

Form A of compound 5 was prepared as follows.

Compound A was dissolved in EtOH (10 vol, 500 µl) at ambient conditions. The solution was heated to 50° C., then treated with hydrochloric acid (1.0 mol eq. added as a stock solution in THF, 1M). A cooling ramp was applied from 50° C. to 5° C. at 0.1° C./min. After 20 hours, solid obtained was filtered, air dried and analysed by the appropriate techniques.

Characterization of the resulting material demonstrated a hydrated, slightly hygroscopic crystalline Form A.

Table 9, supra, is reproduced below and sets forth the X-ray diffraction peaks observed for Form A of compound 5.

TABLE 9

XRPD Peak Positions for Form A of Compound 5

| Position (°2θ) | Intensity % |
|---|---|
| 8.7 | 17.6 |
| 9.7 | 11.3 |

TABLE 9-continued

XRPD Peak Positions for Form A of Compound 5

| Position (°2θ) | Intensity % |
|---|---|
| 10.7 | 21.6 |
| 16.2 | 9.9 |
| 17.0 | 100.0 |
| 17.3 | 9.6 |
| 19.9 | 5.6 |
| 22.6 | 25.7 |
| 24.7 | 8.2 |
| 25.2 | 11.9 |
| 26.1 | 25.7 |
| 29.3 | 17.6 |
| 29.9 | 10.5 |
| 32.0 | 10.6 |

1 In this and all subsequent tables, the position 2θ is within ±0.2.

FIG. 16 depicts an XRPD pattern of Form A of compound 5.

Figure 17:
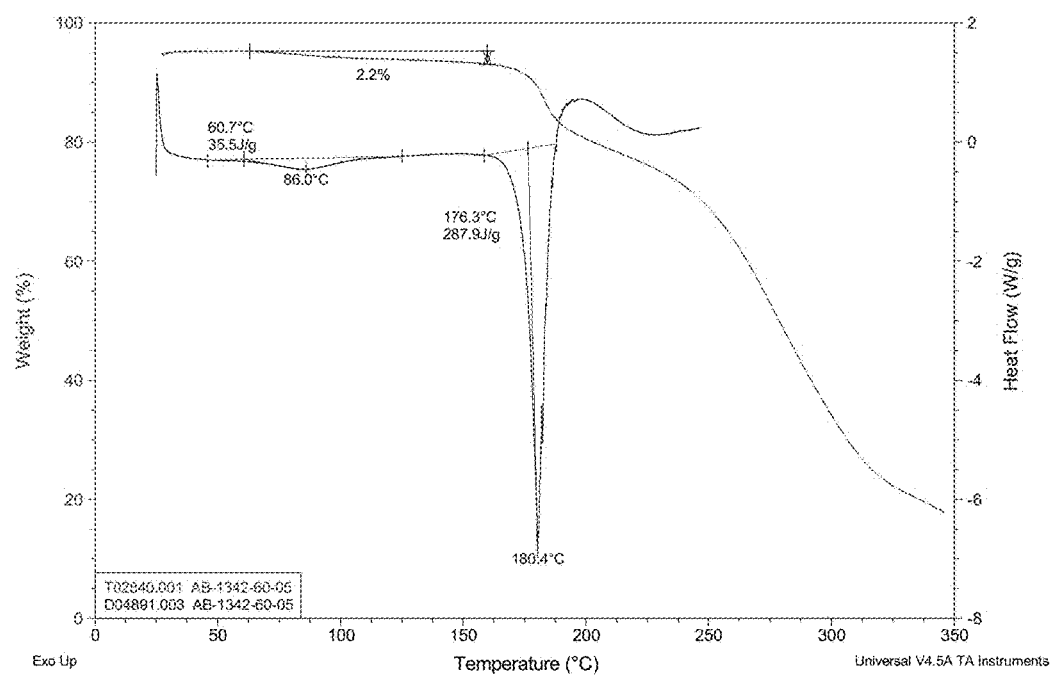
FIG. 17 depicts a DSC thermogram and TGA trace of Compound 5, Form A.

FIG. 17 depicts a DSC thermogram and TGA trace of Form A of compound 5.

Example 7

Preparation of Form A of Compound 6

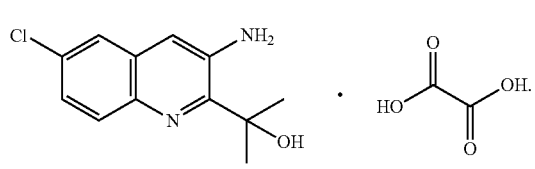

Form A of Compound 6

Form A of compound 6 was prepared as follows.

Compound A was dissolved in EtOH (10 vol, 500 μl) at ambient conditions. The solution was heated to 50° C., then treated with oxalic acid (1.0 mol eq. added as a stock solution in THF, 1M). A cooling ramp was applied from 50° C. to 5° C. at 0.1° C./min. After 20 hours, no solid obtained wand the solution was cooled at −20° C. for 48 h. If no solid was obtained post cooling, the solution was treated with antisolvent (TBME, 500 μl). If no solid was obtained after 24 h, the solution was allowed to evaporate at ambient conditions. A solid was obtained after 24 h and was analysed by the appropriate techniques.

Characterization of the resulting material demonstrated a crystalline, hydrated Form A.

Table 10, supra, is reproduced below and sets forth the X-ray diffraction peaks observed for Form A of compound 6.

TABLE 10

XRPD Peak Positions for Form A of Compound 6

| Position (°2θ) | Intensity % |
|---|---|
| 8.4 | 16.1 |
| 11.1 | 48.0 |
| 12.5 | 50.0 |
| 13.3 | 13.9 |
| 13.9 | 11.8 |
| 14.6 | 10.2 |
| 15.5 | 11.0 |
| 16.0 | 10.8 |
| 16.9 | 100.0 |
| 17.3 | 23.3 |
| 19.1 | 22.3 |
| 19.8 | 60.4 |
| 22.4 | 28.5 |
| 23.6 | 27.7 |
| 24.0 | 28.7 |
| 24.3 | 25.3 |
| 24.4 | 23.3 |
| 25.3 | 64.9 |
| 25.6 | 27.5 |
| 26.1 | 14.9 |
| 26.3 | 15.7 |
| 27.3 | 16.5 |
| 27.8 | 23.7 |

1 In this and all subsequent tables, the position 2θ is within ±0.2.

FIG. 18 depicts an XRPD pattern of Form A of compound 6.

Figure 19:
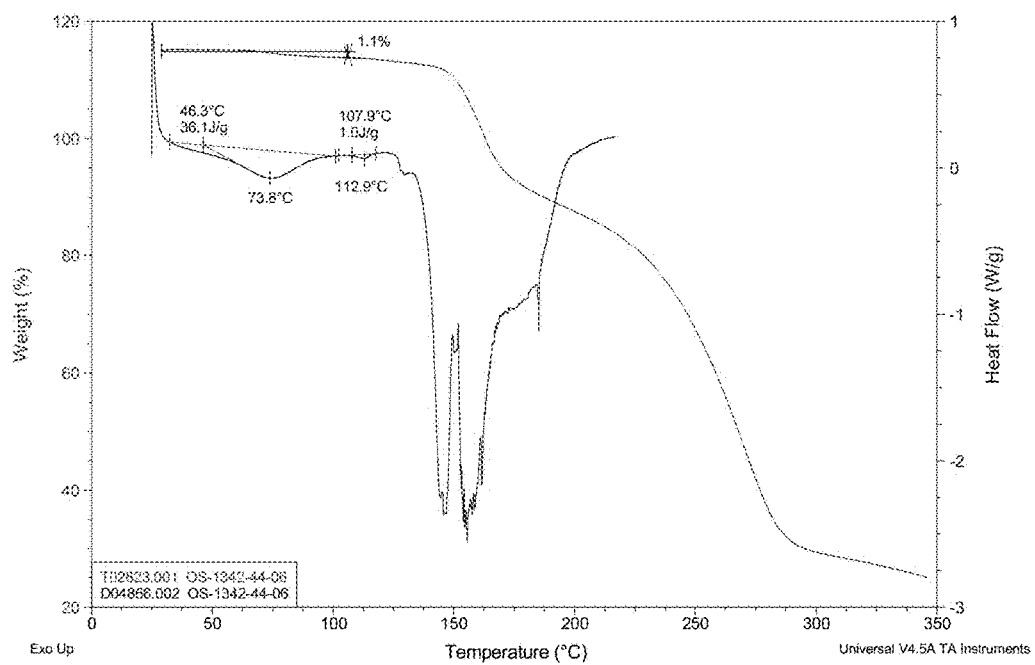
FIG. 19 depicts a DSC thermogram and TGA trace of Compound 6, Form A.

FIG. 19 depicts a DSC thermogram and TGA trace of Form A of compound 6.

Example 8

Preparation of Form A of Compound 7

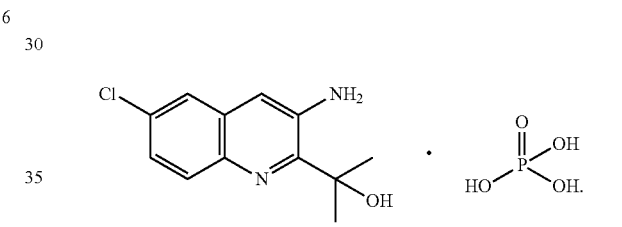

Form A of Compound 7

Form A of compound 7 was prepared as follows.

Compound A was dissolved in EtOH (10 vol, 1 ml) at ambient conditions. The clear solution was treated with phosphoric acid (1.0 mol eq., added as a stock solution in THF, 1M). After addition of the acid, a clear solution was obtained and was treated with 8 ml of the given antisolvent (heptane). The sample was stirred overnight. The sample was filtered, air dried at ambient conditions and analysed by the appropriate techniques.

Characterization of the resulting material demonstrated a non-hydrated, slightly hygroscopic crystalline Form A.

Table 11, supra, is reproduced below and sets forth the X-ray diffraction peaks observed for Form A of compound 7.

TABLE 11

XRPD Peak Positions for Form A of Compound 7

| Position (°2θ) | Intensity % |
|---|---|
| 8.1 | 10.6 |
| 8.9 | 7.1 |
| 9.7 | 9.4 |
| 15.9 | 6.6 |
| 16.1 | 33.2 |
| 16.8 | 48.7 |
| 17.7 | 42.1 |
| 18.1 | 12.8 |
| 18.2 | 12.6 |

TABLE 11-continued

XRPD Peak Positions for Form A of Compound 7

| Position (°2θ) | Intensity % |
|---|---|
| 18.7 | 5.0 |
| 19.3 | 22.5 |
| 19.5 | 16.5 |
| 20.3 | 6.1 |
| 20.9 | 34.6 |
| 21.2 | 10.0 |
| 24.0 | 25.6 |
| 24.3 | 72.5 |
| 24.7 | 6.7 |
| 26.1 | 10.3 |
| 26.3 | 22.0 |
| 27.8 | 100.0 |
| 30.5 | 12.5 |
| 31.5 | 31.2 |
| 31.8 | 11.4 |
| 32.3 | 11.0 |
| 33.7 | 17.5 |

[1] In this and all subsequent tables, the position 2θ is within ±0.2.

FIG. 20 depicts an XRPD pattern of Form A of compound 7.

Figure 21:
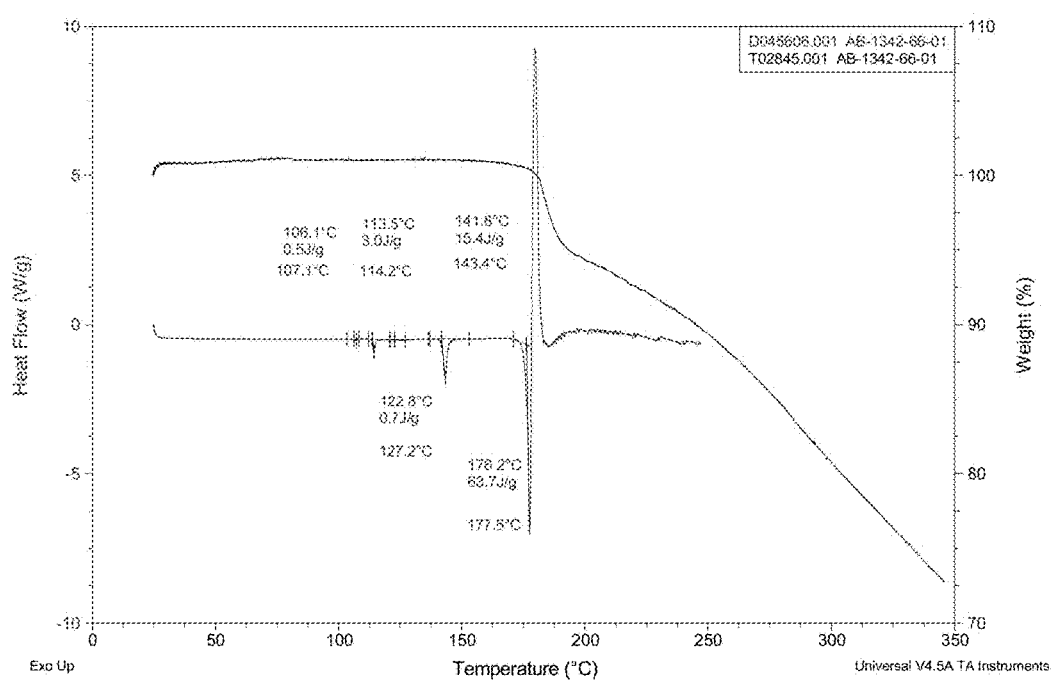
FIG. 21 depicts a DSC thermogram and TGA trace of Compound 7, Form A.

FIG. 21 depicts a DSC thermogram and TGA trace of Form A of compound 7.

Example 9

Preparation of Forms A and B of Compound 8

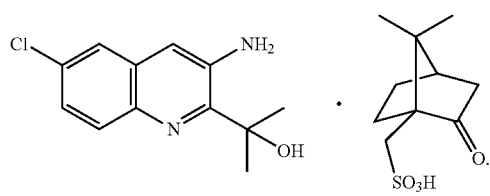

Form A of Compound 8

Form A of compound 8 was prepared as follows.

Compound A was dissolved in EtOH (10 vol, 500 μl) at ambient conditions. The solution was heated to 50° C., then treated with camphorsulfonic acid (1.0 mol eq. added as a stock solution, 1M). A cooling ramp was applied from 50° C. to 5° C. at 0.1° C./min. After 20 hours, the solution was treated with antisolvent (TBME, 4 ml) at ambient conditions. If no solid was obtained post cooling, then antisolvent solutions were filtered, air dried and the attained solid was further analyzed by the appropriate techniques.

Characterization of the resulting material demonstrated a crystalline, anhydrous Form A.

Table 12, supra, is reproduced below and sets forth the X-ray diffraction peaks observed for Form A of compound 8.

TABLE 12

XRPD Peak Positions for Form A of Compound 8

| Position (°2θ) | Intensity % |
|---|---|
| 5.6 | 8.8 |
| 7.1 | 100.0 |
| 8.8 | 5.2 |

TABLE 12-continued

XRPD Peak Positions for Form A of Compound 8

| Position (°2θ) | Intensity % |
|---|---|
| 10.3 | 14.3 |
| 11.9 | 5.4 |
| 14.1 | 14.4 |
| 14.3 | 5.2 |
| 15.2 | 4.9 |
| 15.3 | 6.9 |
| 15.5 | 4.1 |
| 17.2 | 25.7 |
| 17.6 | 5.1 |
| 18.1 | 6.9 |
| 18.2 | 6.3 |
| 18.4 | 20.6 |
| 18.7 | 6.9 |
| 18.8 | 8.0 |
| 19.2 | 3.2 |
| 20.2 | 7.7 |
| 22.2 | 9.7 |
| 24.2 | 11.1 |
| 24.7 | 8.9 |

[1] In this and all subsequent tables, the position 2θ is within ±0.2.

FIG. 22 depicts an XRPD pattern of Form A of compound 8.

Figure 23:
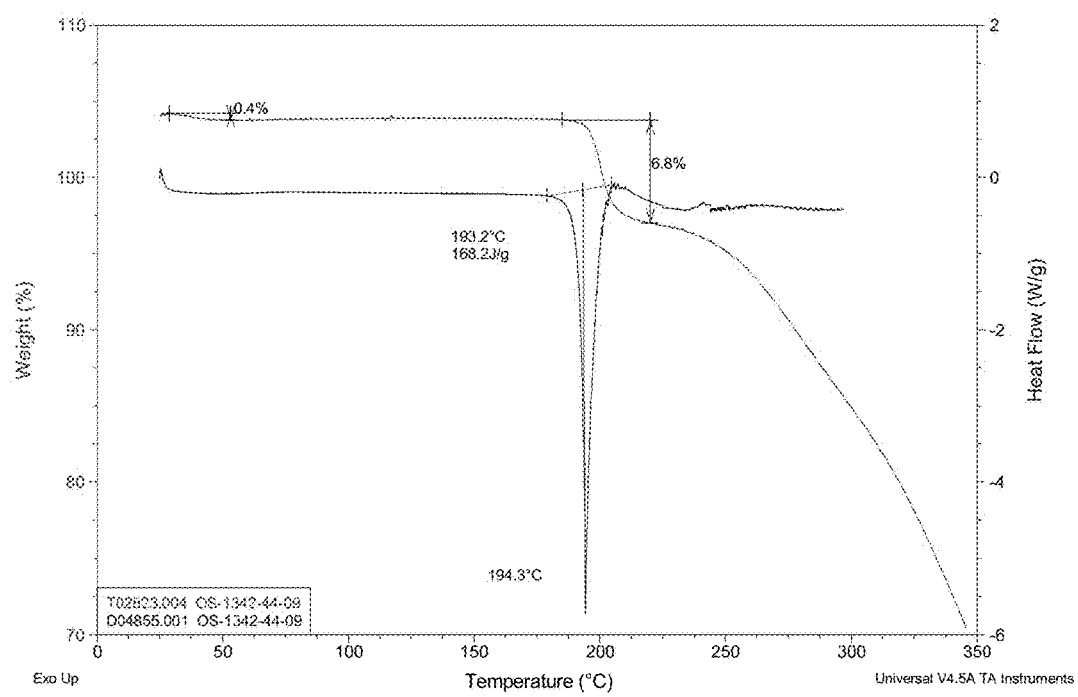
FIG. 23 depicts a DSC thermogram and TGA trace of Compound 8, Form A.

FIG. 23 depicts a DSC thermogram and TGA trace of Form A of compound 8.

Example 10

Preparation of Form A of Compound 9

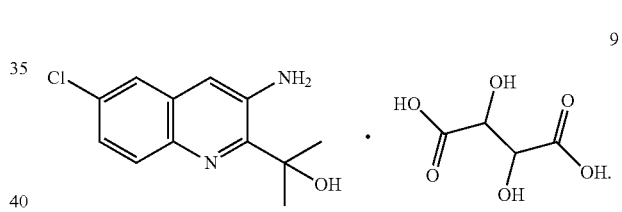

Form A of Compound 9

Form A of compound 9 was prepared as follows.

Compound A was dissolved in EtOH (10 vol, 500 μl) at ambient conditions. The solution was heated to 50° C., then treated with tartaric acid (1.0 mol eq. added as a stock solution, 1M). A cooling ramp was applied from 50° C. to 5° C. at 0.1° C./min. After 20 hours, no solid obtained wand the solution was cooled at −20° C. for 48 h. If no solid was obtained post cooling, the solution was treated with antisolvent (TBME, 500 μl). If no solid was obtained after 24 h, the solution was allowed to evaporate at ambient conditions. A solid was obtained after 24 h and was analysed by the appropriate techniques.

Characterization of the resulting material demonstrated a crystalline, hydrated Form A.

Table 13, supra, is reproduced below and sets forth the X-ray diffraction peaks observed for Form A of compound 9.

TABLE 13

XRPD Peak Positions for Form A of Compound 9

| Position (°2θ) | Intensity % |
|---|---|
| 7.2 | 69.6 |
| 8.1 | 83.8 |

TABLE 13-continued

XRPD Peak Positions for Form A of Compound 9

| Position (°2θ) | Intensity % |
|---|---|
| 13.8 | 23.6 |
| 14.6 | 37.8 |
| 15.4 | 66.2 |
| 15.6 | 34.5 |
| 16.1 | 84.5 |
| 16.6 | 36.5 |
| 17.1 | 31.1 |
| 17.3 | 52.0 |
| 18.4 | 45.3 |
| 19.0 | 62.2 |
| 19.2 | 31.1 |
| 19.6 | 51.4 |
| 19.9 | 45.3 |

[1] In this and all subsequent tables, the position 2θ is within ±0.2.

FIG. 24 depicts an XRPD pattern of Form A of compound 9.

Figure 25:
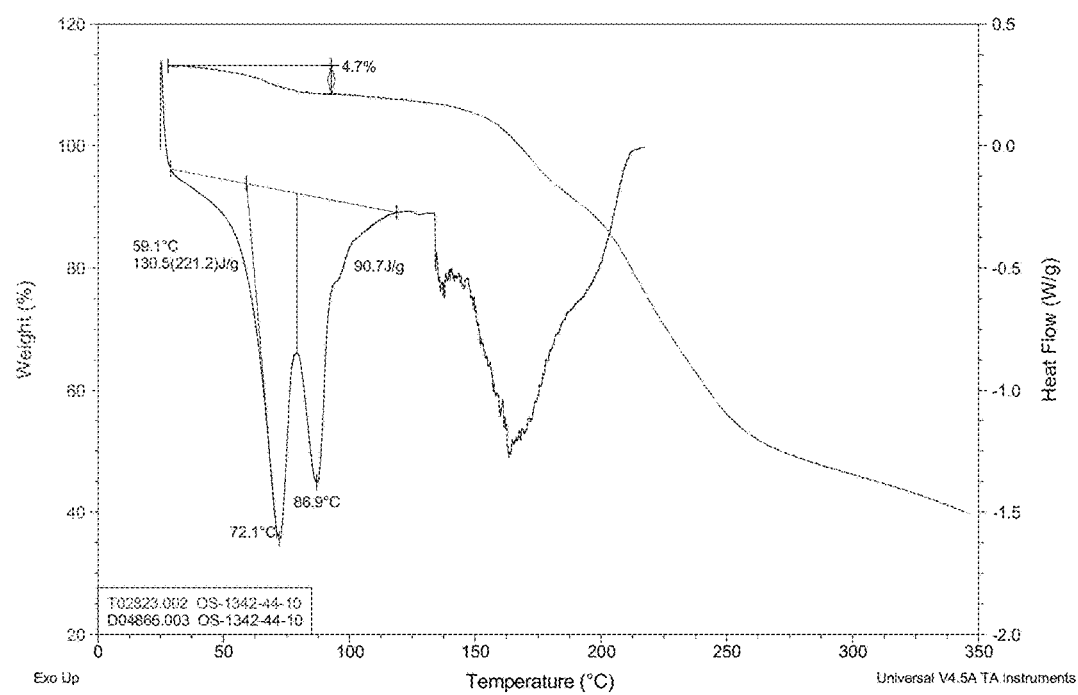
FIG. 25 depicts a DSC thermogram and TGA trace of Compound 9, Form A.

FIG. 25 depicts a DSC thermogram and TGA trace of Form A of compound 9.

Example 11

Aqueous Solubility Studies for Compounds 1 and 3-8

Aqueous solubility studies for salt Compounds 1 and 3-8 were determined via calibration curve. Each of Compounds 1 and 3-8 were prepared at five different levels of concentration (e.g., 0.25 mM, 0.5 mM, 0.75 mM, 1.0 mM and 2.0 mM) and the calibration curve for each salt was derived upon plotting HPLC response measurements against salt solution concentrations.

The solubility determination was made as follows. Each salt suspension was made by adding 50-100 mg of material into a minimum amount of water (0.1-0.2 mL to start). Based on solubility, additional material was added to obtain a salt suspension. The suspension was then filtered through a 0.25 μm filter and the filtrate was further diluted with water and the salt solution was analysed by HPLC. The concentration of the salt solution injected was calculated with the linear equation y=mx+c derived from the calibration curves, with Y referring to the HPLC response obtained for the salt solution injected. The results are shown below in Table 15.

TABLE 15

Solubility Determinations of Compounds 1 and 3-8

| Compound | Concentration | Dilution Factor | Accuracy Level (R$^2$)* | Solubility |
|---|---|---|---|---|
| A | — | — | — | <0.1 mg/mL |
| 1 | 175 mg/0.1 mL | — | 99.56 | >1.5 g/mL |
| 3 | 100 mg/0.3 mL | 1000x | 98.27 | 421 mg/mL |
| 4 | 50 mg/mL | 40x | 99.31 | 11 mg/mL |
| 5 | 50 mg/0.5 mL | 500x | 95.06 | 73 mg/mL |
| 6 | 50 mg/0.5 mL | 100x | 99.10 | 15.6 mg/mL |
| 7 | 50 mg/0.1 mL | — | 94.08 | >500 mg/mL |
| 8 | 50 mg/0.4 mL | 100x | 98.84 | 35 mg/mL |

*R$^2$ value was obtained from calibration curves

As can be seen, Compounds 1 and 3-8 are far more soluble than the freebase compound A, with Compound 1 showing the highest solubility.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A solid form of compound 1:

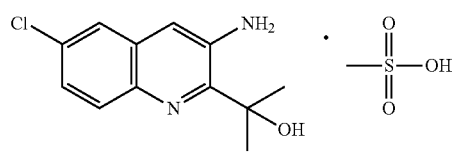

having one or more peaks in its XRPD selected from those at about 9.3, about 16.9, and about 26.4 degrees 2-theta; or having one or more peaks in its XRPD selected from those at about 9.6, about 19.1, and about 28.8 degrees 2-theta.

2. The solid form according to claim 1, wherein said compound is crystalline.

3. The solid form according to claim 1, wherein said compound is a crystalline solid substantially free of amorphous compound 1.

4. The solid form according to claim 1, wherein said compound is substantially free of impurities.

5. The solid form according to claim 1, having at least two peaks in its XRPD selected from those at about 9.3, about 16.9, and about 26.4 degrees 2-theta.

6. The solid form according to claim 5, wherein said compound is of Form A.

7. The solid form according to claim 1, having an XRPD substantially similar to that depicted in FIG. 5.

8. The solid form according to claim 1, having at least two peaks in its XRPD selected from those at about 9.6, about 19.1, and about 28.8 degrees 2-theta.

9. The solid form according to claim 8, wherein said compound is of Form B.

10. The solid form according to claim 1, having an XRPD substantially similar to that depicted in FIG. 7.

11. A pharmaceutically acceptable composition comprising the solid form according to claim 1 and a pharmaceutically acceptable carrier, excipient, or vehicle.

12. A compound selected from:

Compound A:

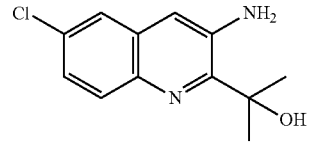

of Form A or B, wherein Form A has one or more peaks in its XRPD selected from those at about 5.4, about 10.8, and about 16.6 degrees 2-theta and Form B has one or more peaks in its XRPD selected from those at about 11.6, about 23.3, and about 35.3 degrees 2-theta;

Compound 2:

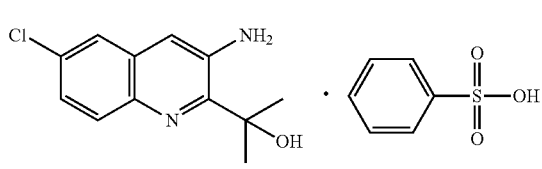

of Form A or B, wherein Form A has one or more peaks in its XRPD selected from those at about 8.4, about 14.0, and about 25.4 degrees 2-theta and Form B has one or more peaks in its XRPD selected from those at about 8.4, about 26.8, and about 29.3 degrees 2-theta;

Compound 3:

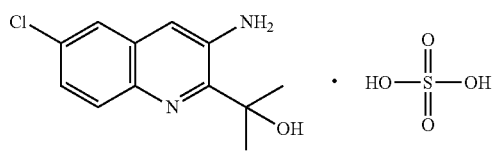

of Form A, wherein Form A has one or more peaks in its XRPD selected from those at about 17.2, about 23.8, and about 25.5 degrees 2-theta;

Compound 4:

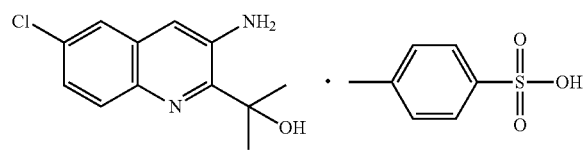

of Form A, wherein Form A has one or more peaks in its XRPD selected from those at about 13.4, about 17.0, and about 25.9 degrees 2-theta;

Compound 5:

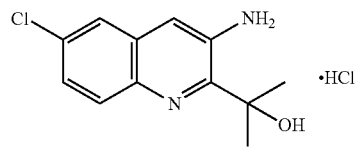

of Form A, wherein Form A has one or more peaks in its XRPD selected from those at about 17.0, about 22.6, and about 26.1 degrees 2-theta;

Compound 6:

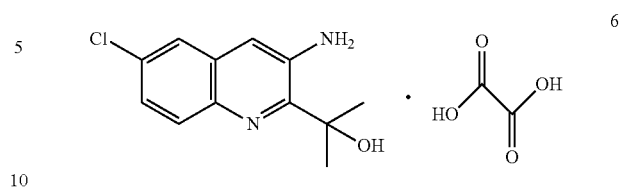

of Form A, wherein Form A has one or more peaks in its XRPD selected from those at about 16.9, about 19.8, and about 25.3 degrees 2-theta;

Compound 7:

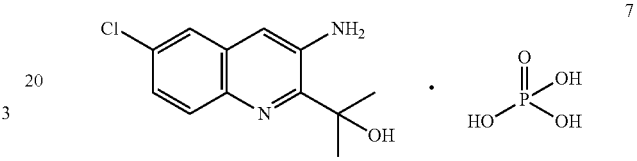

of Form A, wherein Form A has one or more peaks in its XRPD selected from those at about 16.8, about 24.3, and about 27.8 degrees 2-theta;

Compound 8:

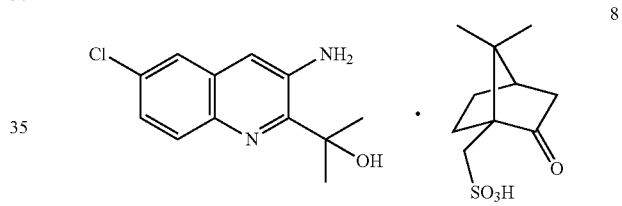

of Form A, wherein Form A has one or more peaks in its XRPD selected from those at about 7.1, about 17.2, and about 18.4 degrees 2-theta;
or
Compound 9:

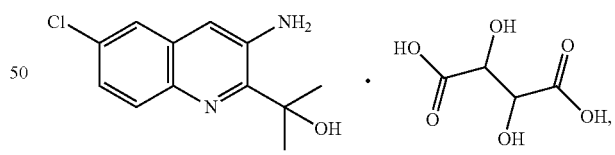

of Form A, wherein Form A has one or more peaks in its XRPD selected from those at about 7.2, about 8.1, and about 16.1 degrees 2-theta.

13. A pharmaceutically acceptable composition comprising a compound according to claim 12, and a pharmaceutically acceptable carrier, excipient, or vehicle.

14. The compound according to claim 12, wherein said compound is crystalline.

15. The compound according to claim 12, wherein said compound is substantially free of impurities.

* * * * *